United States Patent
Lau et al.

(10) Patent No.: US 10,463,616 B2
(45) Date of Patent: *Nov. 5, 2019

(54) LIPID CONSTRUCT FOR DELIVERY OF INSULIN TO A MAMMAL

(71) Applicant: SDG, INC., Cleveland, OH (US)

(72) Inventors: John R. Lau, Howard, OH (US); W. Blair Geho, Wooster, OH (US)

(73) Assignee: SDG, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/978,820

(22) Filed: May 14, 2018

(65) Prior Publication Data
US 2019/0054021 A1    Feb. 21, 2019

Related U.S. Application Data

(63) Continuation of application No. 13/916,115, filed on Jun. 12, 2013, now Pat. No. 10,004,686, which is a
(Continued)

(51) Int. Cl.
*A61K 38/28* (2006.01)
*A61K 47/14* (2017.01)
(Continued)

(52) U.S. Cl.
CPC .......... *A61K 9/1271* (2013.01); *A61K 9/1272* (2013.01); *A61K 38/28* (2013.01);
(Continued)

(58) Field of Classification Search
CPC .................................................. A61K 9/127
See application file for complete search history.

(56) References Cited

U.S. PATENT DOCUMENTS

| | | |
|---|---|---|
| 4,603,044 A | 7/1986 | Geho et al. |
| 4,762,915 A | 8/1988 | Kung et al. |

(Continued)

FOREIGN PATENT DOCUMENTS

| | | |
|---|---|---|
| CA | 2431212 A1 | 7/2002 |
| WO | 8800474 A1 | 1/1988 |
| WO | 9959545 A1 | 11/1999 |

OTHER PUBLICATIONS

Vesely,D.L. et al., Isolation of a Biotin Receptor From Hepatic Plasma Membranes, Biochemical and Biophysical Research Communications, vol. 143, No. 3 ,1987 ,pp. 913-916.

*Primary Examiner* — Gollamudi S Kishore
(74) *Attorney, Agent, or Firm* — Saul Ewing Arnstein & Lehr LLP; Kathryn Doyle; Domingos J. Silva

(57) ABSTRACT

The instant invention is drawn to a hepatocyte targeted composition comprising insulin associated with a lipid construct comprising an amphipathic lipid and an extended amphipathic lipid that targets the construct to a receptor displayed by an hepatocyte. The composition can comprise a mixture of free insulin and insulin associated with the complex. The composition can be modified to protect insulin and the complex from degradation. The invention also includes methods for the manufacture of the composition and loading insulin into the composition and recycling various components of the composition. Methods of treating individuals inflicted with diabetes.

11 Claims, 23 Drawing Sheets

Specification includes a Sequence Listing.

Related U.S. Application Data continuation of application No. 11/920,905, filed as application No. PCT/US2006/019119 on May 16, 2006, now abandoned, which is a continuation-in-part of application No. 11/384,728, filed on Mar. 20, 2006, now Pat. No. 7,871,641, and a continuation-in-part of application No. 11/384,659, filed on Mar. 20, 2006, now Pat. No. 7,858,116.

(60) Provisional application No. 60/683,878, filed on May 23, 2005.

(51) Int. Cl.
    *A61K 47/24*     (2006.01)
    *A61K 47/28*     (2006.01)
    *A61K 9/127*     (2006.01)

(52) U.S. Cl.
    CPC .............. *A61K 47/14* (2013.01); *A61K 47/24* (2013.01); *A61K 47/28* (2013.01)

(56) References Cited

U.S. PATENT DOCUMENTS

| | | |
|---|---|---|
| 4,863,896 A | 9/1989 | Geho et al. |
| 4,946,787 A | 8/1990 | Eppstein et al. |
| 5,059,421 A | 10/1991 | Loughrey et al. |
| 5,104,661 A | 4/1992 | Lau |
| 5,376,380 A | 12/1994 | Kikuchi et al. |
| 5,399,331 A * | 3/1995 | Loughrey ............ A61K 9/1271 424/417 |
| 5,690,907 A * | 11/1997 | Lanza .................... A61K 49/18 424/450 |
| 6,004,583 A | 12/1999 | Plate et al. |
| 6,077,834 A | 6/2000 | Cheng |
| 6,207,185 B1 | 3/2001 | See et al. |
| 6,573,101 B1 | 6/2003 | Goomer |
| 6,692,766 B1 | 2/2004 | Rubinstein et al. |
| 7,169,410 B1 | 1/2007 | Lau et al. |
| 7,192,605 B2 | 3/2007 | Herweijer et al. |
| 7,858,116 B2 | 12/2010 | Lau et al. |
| 7,871,641 B2 | 1/2011 | Lau et al. |
| 9,034,372 B2 | 5/2015 | Lau et al. |
| 2002/0061331 A1 | 5/2002 | Zasadzinski et al. |
| 2003/0133972 A1 | 7/2003 | Danthi et al. |
| 2004/0033256 A1 | 2/2004 | Margalit et al. |
| 2005/0008688 A1 | 1/2005 | Betageri et al. |
| 2005/0026826 A1 | 2/2005 | Hoenig |
| 2005/0123600 A1 | 6/2005 | Trubetskoy et al. |
| 2005/0175541 A1 | 8/2005 | Lanza et al. |
| 2005/0202075 A1 | 9/2005 | Pardridge et al. |
| 2009/0123530 A1 | 5/2009 | Betageri et al. |

\* cited by examiner pH 4.5
Protonated Form
of Iminobiotin pH 9.5 - pH 11.0
Non-protonated Form
of Iminobiotin A-Chain (A1)                                                                                     (A21)
GlyIleValGluGluCysCysThrSerIleCysSerLeuTyrGlnLeuGluAsnTyrCysAsn PheValAsnGlnHisLeuCysGlySerHisLeuValGluAlaLeuTyrLeuValCysGlyGluArgGly
(B1)
                                                    ThrLysProThrTyrPhePhe
B-Chain                                             (B30)
Human Insulin MetProArgArgArgArgSerSerSerArgProValArgArgArgArgArg
                                                                    /
ArgArgArgArgGlyGlyArgArgArgArgArgSerValArgPro
Protamine

FIG. 14

Prepare Mixture of Lipid Components

Combine Components
↓
Dissolve Components
↓
Heat Solution
↓
Dry Mixture under Vacuum
↓
Store Mixture of Lipid Components Form Lipid Construct from Mixture of Lipid Components Hydrate Mixture of Lipid Components
↓
Microfluidize Solution
↓
Filter Solution
↓
Store Lipid Construct Prepare Lipid Construct Containing Insulin Add Insulin to Lipid Construct

FIG. 15

Prepare Target Molecule Complex

Combine Components
↓
Dissolve Components
↓
Heat Solution
↓
Dry Mixture under Vacuum
↓
Store HDV Intermediate Incorporate Complex Into Lipid Construct Hydrate HDV Intermediate
↓
Microfluidize Solution
↓
Filter Solution
↓
Adjust pH
↓
Store Lipid Construct Prepare HDV – Glargine Adjust pH of Sterile Aqueous Media
↓
Mix HDV with Aqueous Media
↓
Adjust pH of HDV/ Aqueous Media
↓
Adjust pH of Glargine Insulin
↓
Add Glargine Insulin to HDV/ Aqueous Media

FIG. 16

Prepare Target Molecule Complex

Combine Components
↓
Dissolve Components in Organic Solvent
↓
Heat Solution
↓
Dry Mixture under Vacuum
↓
Store HDV Intermediate Incorporate Complex Into Lipid Construct Hydrate HDV Intermediate
↓
Heat Solution
↓
Microfluidize Solution
↓
Filter Solution
↓
Store Lipid Construct Prepare HDV–Humulin R insulin in combination with Humulin NPH insulin
↓
Add Humulin NPH Insulin to HDV Humulin R insulin in buffer

LIPID CONSTRUCT FOR DELIVERY OF INSULIN TO A MAMMAL

CROSS-REFERENCE TO RELATED APPLICATIONS

This application is a continuation of, and claims priority to, U.S. patent application Ser. No. 13/916,115, filed Jun. 12, 2013, now issued as U.S. Pat. No. 10,004,686, which is a continuation of, and claims priority to, U.S. patent application Ser. No. 11/920,905, filed Nov. 18, 2009, which is a U.S. national phase application filed under 35 U.S.C. § 371 claiming priority to International Patent Application No. PCT/US2006/019119, filed May 16, 2006, which is a continuation-in-part of, and claims priority to, U.S. patent application Ser. No. 11/384,728, filed Mar. 20, 2006, now issued as U.S. Pat. No. 7,871,641, is a continuation-in-part of, and claims priority to, U.S. patent application Ser. No. 11/384,659, filed Mar. 20, 2006, now issued as U.S. Pat. No. 7,858,116; and claims priority under 35 U.S.C. § 119(e) to U.S. Provisional Application No. 60/683,878, filed May 23, 2005, all of which applications are hereby incorporated herein by reference in their entireties.

BACKGROUND OF THE INVENTION

Diabetes is a disorder affecting large numbers of people worldwide. Management approaches to control Type I and Type II diabetes aim primarily at normalizing blood glucose levels to prevent short- and long-term complications. Many patients require multiple daily injections of an insulin to control their diabetes. Several insulin products have been produced that control blood sugar levels over differing time intervals. Several products combine various forms of insulin in an attempt to provide a preparation which controls glucose levels over a wider period of time.

Previous attempts to normalize blood glucose levels in Type I and Type II diabetic patients have centered on the subcutaneous administration of insulin in various time-released formulations, such as ultralente and humulin NPH insulin pharmaceutical products. These formulations have attempted to delay and subsequently control the bio-distribution of insulin by regulating release of insulin to peripheral tissues with the expectation that sustained management of insulin bio-availability will lead to better glucose control. Glargine insulin is a long-acting form of insulin in which insulin is released from the subcutaneous tissue around the site of injection into the bloodstream at a relatively constant rate throughout the day. Although glargine insulin is released at a constant rate throughout the day, the released insulin reaches a wide range of systems within the body rather than being delivered to targeted areas of the body. What is needed is a composition of insulin where a portion of the dosed insulin is released at a relatively constant rate throughout the day and another portion of insulin that is time released from the site of administration and targeted for delivery to the liver to better control glucose production.

There is, therefore, an unmet need in the art for compositions and methods of managing blood glucose levels in Type I and Type II diabetic patients. The present invention meets these needs by providing a long-acting composition comprising insulin that is free and insulin that is associated with a lipid construct targeted for delivery to hepatocytes. A lipid construct is a lipid/phospholipid particle in which individual lipid molecules cooperatively interact to create a bipolar lipid membrane which encloses and isolates a portion of the medium in which it was formed. The lipid construct releases free insulin over time as well as targets a portion of the remaining insulin to the hepatocytes in the liver to better control glucose storage and production.

BRIEF SUMMARY OF THE INVENTION

In one aspect, the present invention includes a lipid construct comprising an amphipathic lipid and an extended amphipathic lipid, wherein the extended amphipathic lipid comprises proximal, medial and distal moieties, wherein the proximal moiety connects the extended amphipathic lipid to the construct, the distal moiety targets the construct to a receptor displayed by a hepatocyte, and the medial moiety connects the proximal and distal moieties.

In another aspect, the lipid construct further comprises at least one insulin.

In still another aspect, the at least one insulin is selected from the group consisting of insulin lispro, insulin aspart, regular insulin, insulin glargine, insulin zinc, human insulin zinc extended, isophane insulin, human buffered regular insulin, insulin glulisine, recombinant human regular insulin, recombinant human insulin isophane, premixed combinations of any of the aforementioned insulins, a derivative thereof, and a combination of any of the aforementioned insulins.

In another aspect, the lipid construct further comprises an insoluble form of at least one insulin associated with the lipid construct.

In yet another aspect, the amphipathic lipid comprises at least one lipids selected from the group consisting of 1,2-distearoyl-sn-glycero-3-phosphocholine, cholesterol, dicetyl phosphate, 1,2-dipalmitoyl-sn-glycerol-[3-phospho-rac-(1-glycero)], 1,2-distearoyl-sn-glycero-3-phosphoethanolamine, 1,2-dipalmitoyl-sn-glycero-3-phosphoethanolamine-N-(succinyl), derivatives thereof, and mixtures of any of the foregoing compounds.

In one aspect, the proximal moiety of the extended amphipathic lipid comprises at least one, but not more than two, long acyl hydrocarbon chains bound to a backbone, wherein each hydrocarbon chain is independently selected from the group consisting of a saturated hydrocarbon chain and an unsaturated hydrocarbon chain.

In another aspect, the backbone comprises glycerol.

In still another aspect, the distal moiety of the extended amphipathic lipid comprises at least one member selected from the group consisting of biotin, a biotin derivative, iminobiotin, an iminobiotin derivative, biocytin, a biocytin derivative, iminobiocytin, an iminobiocytin derivative and a hepatocyte specific molecule that binds to a receptor in a hepatocyte.

In yet another aspect, the extended amphipathic lipid is selected from the group consisting of N-hydroxysuccinimide (NHS) biotin; sulfo-NHS-biotin; N-hydroxysuccinimide long chain biotin; sulfo-N-hydroxysuccinimide long chain biotin; D-biotin; biocytin; sulfo-N-hydroxysuccinimide-S—S-biotin; biotin-BMCC; biotin-HPDP; iodoacetyl-LC-biotin; biotin-hydrazide; biotin-LC-hydrazide; biocytin hydrazide; biotin cadaverine; carboxybiotin; photobiotin; p-aminobenzoyl biocytin trifluoroacetate; p-diazobenzoyl biocytin; biotin DHPE; biotin-X-DHPE; 12-((biotinyl)amino)dodecanoic acid; 12-((biotinyl)amino)dodecanoic acid succinimidyl ester; S-biotinyl homocysteine; biocytin-X; biocytin x-hydrazide; biotinethylenediamine; biotin-XL; biotin-X-ethylenediamine; biotin-XX hydrazide; biotin-XX-SE; biotin-XX, SSE; biotin-X-cadaverine; α-(t-BOC)biocytin; N-(biotinyl)-N'-(iodoacetyl) ethylenediamine; DNP-X-biocytin-X-SE; biotin-X-hydrazide; norbiotinamine hydrochloride; 3-(N-maleimidylpropionyl)biocytin; ARP; biotin-1-sulfoxide; biotin methyl ester; biotin-maleimide; biotin-poly(ethyleneglycol)amine; (+) biotin 4-amidobenzoic acid sodium salt; Biotin 2-N-acetylamino-2-deoxy-β-D-glucopyranoside; Biotin-α-D-N-acetylneuraminide; Biotin-α-L-fucoside; Biotin lacto-N-bioside; Biotin-Lewis-A trisaccharide; Biotin-Lewis-Y tetrasaccharide; Biotin-α-D-mannopyranoside; biotin 6-O-phospho-α-D-mannopyranoside; and polychromium-poly(bis)-N-[2,6-(diisopropylphenyl) carbamoyl methylimino] diacetic acid.

In one aspect, the medial moiety of the extended amphipathic lipid comprises a thio-acetyl triglycine polymer or a derivative thereof, wherein the extended amphipathic lipid molecule extends outward from the surface of the lipid construct.

In another aspect, the lipid construct further comprises at least one insulin associated with a water insoluble target molecule complex, wherein the complex comprises a plurality of linked individual units, the individual units comprise: a bridging component selected from the group consisting of a transition element, an inner transition element, a neighbor element of the transition element and a mixture of any of the foregoing elements, and a complexing component, provided that when the transition element is chromium, a chromium target molecule complex is formed.

In yet another aspect, the lipid construct further comprises at least one insulin that is not associated with the target molecule complex.

In a further aspect, the bridging component is chromium.

In one aspect, the complexing component comprises poly(bis)-[(N-(2,6-diisopropylphenyl)carbamoyl methyl) iminodiacetic acid].

In another aspect, the distal component of the extended amphipathic lipid comprises a non-polar derivatized benzene ring or a heterobicyclic ring structure.

In still another aspect, the construct comprises a positive charge, a negative charge or combinations thereof.

In one aspect, the extended amphipathic lipid comprises at least one carbonyl moiety positioned at a distance about 13.5 angstroms or less from the terminal end of the distal moiety.

In another aspect, the extended amphipathic lipid comprises at least one carbamoyl moiety comprising a secondary amine.

In yet another aspect, the extended amphipathic lipid comprises charged chromium in the medial position.

In a further aspect, the lipid construct further comprises cellulose acetate hydrogen phthalate.

In yet another aspect, the lipid construct further comprises at least one charged organic molecule bound to the insulin.

In one aspect, the charged organic molecule is selected from the group consisting of protamines, derivatives of polylysine, highly basic amino acid polymers, poly (arg-pro-thr)n in a mole ratio of 1:1:1, poly (DL-Ala-poly-L-lys)n in a mole ratio of 6:1, histones, sugar polymers that contain a positive charge contributed by a primary amino group, polynucleotides with primary amino groups, carboxylated polymers and polymeric amino acids, fragments of proteins that contain large amounts of amino acid residues with carboxyl (COO—) or sulfhydral (S—) functional groups, derivative of proteins with negatively charged terminal acidic carboxyl groups, acidic polymers, sugar polymers containing negatively charged carboxyl groups, derivative thereof and combinations of the aforemention compounds.

In another aspect, a method of manufacturing a lipid construct comprising an amphipathic lipid and an extended amphipathic lipid, wherein the extended amphipathic lipid comprises proximal, medial and distal moieties, wherein the proximal moiety connects the extended amphipathic lipid to the construct, the distal moiety targets the construct to a receptor displayed by a hepatocyte, and the medial moiety connects the proximal and distal moieties, comprises: creating a mixture comprising the amphipathic lipid and an extended amphipathic lipid; and forming a suspension of the lipid construct in water.

In still another aspect, the method of manufacturing the lipid construct comprising an insulin, an amphipathic lipid and an extended amphipathic lipid, wherein the extended amphipathic lipid comprises proximal, medial and distal moieties, wherein the proximal moiety connects the extended amphipathic lipid to the construct, the distal moiety targets the construct to a receptor displayed by a hepatocyte, and the medial moiety connects the proximal and distal moieties, comprises: creating a mixture comprising the amphipathic lipid and an extended amphipathic lipid; forming a suspension of the lipid construct in water; and loading the insulin into the lipid construct.

In another aspect, the step of loading the insulin into the lipid construct comprises equilibrium loading and non-equilibrium loading.

The still another aspect, the step of loading the insulin into the lipid construct comprises adding a solution containing free insulin to a mixture of the lipid construct in water and allowing the insulin to remain in contact with the mixture until equilibrium is reached.

In yet another aspect, the method further comprises the step of terminally loading the insulin into the lipid construct after the mixture reaches equilibrium, wherein the solution containing free insulin is removed from the construct, further wherein the construct contains insulin associated with the construct.

In one aspect, the method further comprises the step of removing the solution containing free insulin from the lipid construct containing insulin associated with the construct by a process selected from the group consisting of a rapid filtration procedure, centrifugation, filter centrifugation, and chromatography using an ion-exchange resin or streptavidin agarose affinity-resin gel having affinity for biotin, iminobiotin or derivates thereof.

In another aspect, the method further comprises the step of adding a chromium complex comprising a plurality of linked individual units to the lipid construct.

In still another aspect, the method further comprises the step of adding cellulose acetate hydrogen phthalate to the lipid construct.

In yet another aspect, the method further comprises the step of reclaiming from the process at least one material selected from the group consisting of insulin, ion-exchange resin and streptavidin agarose affinity-gel.

In another aspect, the step of loading the insulin into the lipid construct comprises the step of adding at least one charged organic molecule to the insulin before the insulin is loaded into the lipid construct.

In still another aspect, a method of increasing the bioavailability of at least one insulin in a patient comprises: combining at least one insulin with a lipid construct, wherein the lipid construct comprises a plurality of non-covalent multi-dentate binding sites; and administering the construct containing insulin to the patient.

In another aspect, increasing the bioavailability further comprising the step of modulating the isoelectric point of at least one active ingredient.

In yet another aspect, the insulin is selected from the group consisting of insulin lispro, insulin aspart, regular insulin, insulin glargine, insulin zinc, human insulin zinc extended, isophane insulin, human buffered regular insulin, insulin glulisine, recombinant human regular insulin, recombinant human insulin isophane, premixed combinations of any of the aforementioned insulins, a derivative thereof, and a combination of any of the aforementioned insulins.

In yet another aspect, the lipid construct comprises insulin, 1,2-distearoyl-sn-glycero-3-phophocholine, cholesterol, dicetyl phosphate, 1,2-dipalmitoyl-sn-glycero-[3-phospho-rac-(1-glycerol)], 1,2-distearoyl-sn-glycero-3-phosphoethanolamine, and 1,2-dipalmitoyl-sn-glycero-3-phosphoethanolamine-N-(succinyl) or derivatives, and a hepatocyte receptor binding molecule.

In one aspect, the method further comprises the step of adding at least one charged organic molecule to the insulin before the insulin is combined with the lipid construct.

In another aspect, a method of forming a time-release composition that provides increased bio-distribution of insulin in a host comprises: removing a lipid construct from a bulk phase media by binding the construct through lipids comprising iminobiotin or an iminobiotin derivative to streptavidin agarose affinity-gel at pH 9.5 or greater; separating the construct from the bulk phase media; and releasing the construct from the affinity-gel by adjusting the pH of an aqueous mixture of the affinity gel to pH 4.5, wherein, the released construct contains insoluble insulin; wherein upon administration of the construct to a warm-blooded host the insulin is resolubilized under the physiological pH conditions in the host.

In still another aspect, a method of treating a patient afflicted with diabetes comprises administering to the patient an effective amount of a lipid construct comprising insulin associated with the construct.

In yet another aspect, the insulin is selected from the group consisting of insulin lispro, insulin aspart, regular insulin, insulin glargine, insulin zinc, human insulin zinc extended, isophane insulin, human buffered regular insulin, insulin glulisine, recombinant human regular insulin, recombinant human insulin isophane, premixed combinations of any of the aforementioned insulins, a derivative thereof, and a combination of any of the aforementioned insulins.

In one aspect, the lipid construct further comprises a target molecule complex, wherein the complex comprises a plurality of linked individual units, further wherein the linked individual units comprises: a bridging component selected from the group comprising a transition element, an inner transition element, a neighbor element of the transition element and a mixture of any of the foregoing elements; and a complexing component; provided that when the transition element is chromium, a chromium target molecule complex is formed.

In another aspect, the lipid construct further comprises insulin not associated with the target molecule complex.

In still another aspect, the administration is oral or subcutaneous.

In yet another aspect, the insulin associated with the construct comprises at least one charged organic molecule bound to the insulin.

In one aspect, the invention includes a method for increasing the delivery of insulin to hepatocytes in the liver of a patient afflicted with diabetes by administering to the patient a lipid construct comprising insulin, an amphipathic lipid, and an extended lipid, wherein the extended lipid comprises a moiety that binds to hepatocyte receptors, wherein the lipid construct is present in a plurality of sizes.

In another aspect the at least one insulin is selected from the group consisting of insulin lispro, insulin aspart, regular insulin, insulin glargine, insulin zinc, human insulin zinc extended, isophane insulin, human buffered regular insulin, insulin glulisine, recombinant human regular insulin, recombinant human insulin isophane, premixed combinations of any of the aforementioned insulins, a derivative thereof, and a combination of any of the aforementioned insulins.

In still another aspect, the method further comprises protecting the insulin within the lipid construct from hydrolytic degradation by providing a three-dimensional structural array of lipid molecules so as to prevent access to the insulin by hydrolytic enzymes.

In yet another aspect, the method further comprises adding cellulose acetate hydrogen phthalate to the lipid construct to react with individual lipid molecules.

In still another aspect, the method further comprises producing an insolubilized dosage form of insulin within the lipid construct.

In one aspect, the invention includes a kit for use in treating a mammal inflicted with diabetes, the kit comprising a lipid construct, a physiological buffer solution, an applicator, and an instructional material for the use thereof, wherein the lipid construct comprises an amphipathic lipid and an extended amphipathic lipid, wherein the extended amphipathic lipid comprises proximal, medial and distal moieties, wherein the proximal moiety connects the extended amphipathic lipid to the construct, the distal moiety targets the construct to a receptor displayed by a hepatocyte, and the medial moiety connects the proximal and distal moieties.

In another aspect, the kit further comprises at least one insulin.

In one aspect the invention includes a hepatocyte-targeting composition comprises: at least one free insulin; at least one insulin associated with a water-insoluble target molecule complex and a lipid construct matrix comprising at least one lipid component; wherein the target molecule complex is comprised of a combination of: multiple linked individual units, the individual units comprising: at least one bridging component selected from the group consisting of a transition element, an inner transition element, and a neighbor element of the transition element; and a complexing component; provided that when the transition element is chromium, a chromium target molecule complex is created; further wherein the target molecule complex comprises a negative charge.

In another aspect, the at least one insulin is selected from the group consisting of insulin lispro, insulin aspart, regular insulin, insulin glargine, insulin zinc, human insulin zinc extended, isophane insulin, human buffered regular insulin, insulin glulisine, recombinant human regular insulin, recombinant human insulin isophane, premixed combinations of any of the aforementioned insulins, a derivative thereof, and a combination of any of the aforementioned insulins.

In still another aspect, the insulin comprises insulin-like moieties, including fragments of insulin molecules, that have the biological activity of insulins.

In yet another aspect, the lipid component comprises at least one lipid selected from the group consisting of 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dicetylphosphate, 1,2-distearoyl-sn-glycero-3-phosphate, 1,2-dipalmitoyl-sn-glycero-3-phosphate, and 1,2-dimyristoyl-sn-glycero-3-phosphate.

In one aspect, the lipid component comprises at least one lipid selected from the group consisting of 1,2-distearoyl-sn-glycero-3-phosphocholine, cholesterol, and dicetyl phosphate.

In another aspect, the lipid component comprises a mixture of 1,2-distearoyl-sn-glycero-3-phosphocholine, cholesterol and dicetyl phosphate.

In still another aspect, the bridging component is chromium.

In yet another aspect, the complexing component comprises at least one member selected from the group consisting of:

N-(2,6-diisopropylphenylcarbamoylmethyl) iminodiacetic acid;
N-(2,6-diethylphenylcarbamoylmethyl) iminodiacetic acid;
N-(2,6-dimethylphenylcarbamoylmethyl) iminodiacetic acid;
N-(4-isopropylphenylcarbamoylmethyl) iminodiacetic acid;
N-(4-butylphenylcarbamoylmethyl) iminodiacetic acid;
N-(2,3-dimethylphenylcarbamoylmethyl) iminodiacetic acid;
N-(2,4-dimethylphenylcarbamoylmethyl) iminodiacetic acid;
N-(2,5-dimethylphenylcarbamoylmethyl) iminodiacetic acid;
N-(3,4-dimethylphenylcarbamoylmethyl) iminodiacetic acid;
N-(3,5-dimethylphenylcarbamoylmethyl) iminodiacetic acid;
N-(3-butylphenylcarbamoylmethyl) iminodiacetic acid;
N-(2-butylphenylcarbamoylmethyl) iminodiacetic acid;
N-(4-tertiary butylphenylcarbamoylmethyl) iminodiacetic acid;
N-(3-butoxyphenylcarbamoylmethyl) iminodiacetic acid;
N-(2-hexyloxyphenylcarbamoylmethyl) iminodiacetic acid;
N-(4-hexyloxyphenylcarbamoylmethyl) iminodiacetic acid;
aminopyrrol iminodiacetic acid;
N-(3-bromo-2,4,6-trimethylphenylcarbamoylmethyl) iminodiacetic acid;
benzimidazole methyl iminodiacetic acid;
N-(3-cyano-4,5-dimethyl-2-pyrrylcarbamoylmethyl) iminodiacetic acid;
N-(3-cyano-4-methyl-5-benzyl-2-pyrrylcarbamoylmethyl) iminodiacetic acid; and
N-(3-cyano-4-methyl-2-pyrrylcarbamoylmethyl) iminodiacetic acid.

In still another aspect, the complexing component comprises poly(bis)[N-(2,6-diisopropylphenylcarbamoylmethyl) iminodiacetic acid].

In one aspect, the present invention includes a method of manufacturing a hepatocyte-targeting composition comprises: creating a target molecule complex, wherein the complex comprises multiple linked individual units and a lipid construct matrix; forming a suspension of the target molecule complex in buffer; and combining the insulin and the target molecule complex.

In another aspect, a method of manufacturing a hepatocyte-targeting composition comprises: creating a target molecule complex, wherein the complex comprises multiple linked individual units and a lipid construct matrix; forming a suspension of the target molecule complex in water; adjusting the pH of the water suspension to approximately pH 5.3; adjusting the pH of the glargine insulin to approximately 4.8; and combining the glargine insulin and the target molecule complex, wherein the insulin is glargine insulin.

In still another aspect, a method of manufacturing a hepatocyte-targeting composition comprises: creating a target molecule complex, wherein the complex comprises multiple linked individual units and a lipid construct matrix; forming a suspension of the target molecule complex in water; adjusting the pH of the water suspension to approximately pH 5.3; adjusting the pH of the glargine insulin to approximately 4.8; and combining the glargine insulin, the non-glargine insulin and the target molecule complex, wherein the insulin comprises glargine insulin and at least one non-glargine insulin.

In one aspect the present invention includes a method of treating a patient for Type I or Type II diabetes comprising administering to the patient an effective amount of a hepatocyte-targeting composition.

In another aspect, the route of administration is selected from the group consisting of oral, parenteral, subcutaneous, pulmonary and buccal.

In still another aspect, the route of administration is oral or subcutaneous.

In one aspect the present invention includes a method of treating a patient for Type I or Type II diabetes comprising administering to the patient an effective amount of a hepatocyte targeted composition, wherein insulin comprises glargine insulin and at least one non-glargine insulin, further wherein the non-glargine insulin is selected from the group consisting of insulin lispro, insulin aspart, regular insulin, insulin glargine, insulin zinc, human insulin zinc extended, isophane insulin, human buffered regular insulin, insulin glulisine, recombinant human regular insulin, recombinant human insulin isophane, premixed combinations of any of the aforementioned insulins, a derivative thereof, and a combination of any of the aforementioned insulins.

In another aspect, the non-glargine insulin comprises insulin-like moieties, including fragments of insulin molecules, that have biological activity of insulins.

In still another aspect, the present invention includes a method of treating a patient for Type I or Type II diabetes comprising administering to the patient an effective amount of a hepatocyte-targeting composition.

In another aspect, the route of administration is selected from the group consisting of oral, parenteral, subcutaneous, pulmonary and buccal.

In still another aspect, the route of administration is oral or subcutaneous.

In yet another aspect, the present invention includes a method of treating a patient for Type I or Type II diabetes comprising administering to the patient an effective amount of a hepatocyte targeted composition, wherein insulin comprises recombinant human insulin isophane and at least one insulin that is not recombinant human insulin isophane.

In another aspect, the at least one insulin that is not recombinant human insulin isophane comprises insulin-like moieties, including fragments of insulin molecules, that have biological activity of insulins.

In one aspect, the present invention includes a kit for use in treating Type I or Type II diabetes in a mammal, the kit comprising a physiological buffered solution, an applicator, instructional material for the use thereof, and a water insoluble target molecule complex, wherein the complex comprises multiple linked individual units and a lipid construct matrix containing a negative charge, the multiple linked individual units comprising: a bridging component selected from the group consisting of a transition element, an inner transition element, a neighbor element of the transition element and a mixture of any of the foregoing elements, and a complexing component, provided that when the transition element is chromium, a chromium target molecule complex is created, wherein the multiple linked individual units are combined with the lipid construct matrix.

In another aspect, the kit further comprising at least one insulin, wherein the insulin is associated with the target molecule complex-, wherein the complex comprises a charge.

BRIEF DESCRIPTION OF THE DRAWINGS

For the purposes of illustrating the invention, there are depicted in the drawings certain embodiments of the invention. However, the invention is not limited to the precise arrangements and instrumentalities of the embodiments depicted in the drawings.

FIG. 14 is an outline of a method of manufacturing an insulin binding lipid construct comprising amphipathic lipid molecules and an extended amphipathic lipid.

FIG. 15 is an outline of the method of manufacturing a hepatocyte targeted pharmaceutical composition that combines free glargine insulin and glargine insulin associated with a water insoluble target molecule complex.

FIG. 16 is an outline of the method of manufacturing a hepatocyte targeted pharmaceutical composition that combines free recombinant human insulin isophane and recombinant human insulin isophane associated with a water insoluble target molecule complex that contains a portion of recombinant human regular insulin that is both free and associated with a lipid construct.

DETAILED DESCRIPTION OF THE INVENTION

Figure 1:
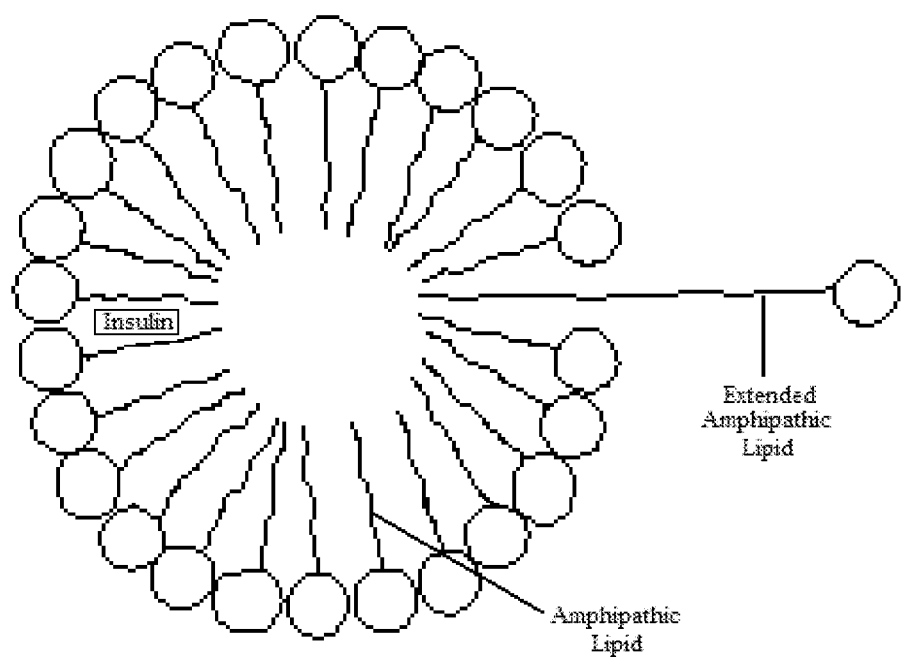
FIG. 1 is a depiction of an insulin binding lipid construct comprising insulin, amphipathic lipid molecules and an extended amphipathic lipid.

The invention includes a hepatocyte targeted pharmaceutical composition where insulin is associated with a water insoluble target molecule complex within the construct and the composition is targeted to hepatocytes in the liver of a patient to provide an effective means of managing diabetes.

The invention includes a lipid construct comprising insulin, an amphipathic lipid and an extended amphipathic lipid (a receptor binding molecule). The extended amphipathic lipid comprises proximal, medial and distal moieties. The proximal moiety connects the extended lipid molecule to the construct, the distal moiety targets the construct to a receptor displayed by a hepatocyte, and the medial moiety connects the proximal and distal moieties.

A lipid construct is a spherical lipid and phospholipid particle in which individual lipid molecules cooperatively interact to create a bipolar lipid membrane which encloses and isolates a portion of the medium in which it was formed. The lipid construct can target the delivery of insulin to the hepatocytes in the liver and provide for a sustained release of insulin to better control diabetes.

The invention also includes a hepatocyte targeted pharmaceutical composition that combines free insulin and insulin associated with a water insoluble target molecule complex targeted to hepatocytes in the liver of a patient to provide an effective means of managing blood glucose levels. When a mixture of different forms of insulin are associated with a target molecule complex to create a unique mixture of insulin molecules, an added therapeutic benefit is achieved once these insulins are combined in a hepatocyte targeted lipid construct. The composition of the invention can be administered by various routes, including subcutaneously or orally, for the purpose of treating mammals afflicted with diabetes.

The invention further provides a method of manufacturing a lipid construct comprising insulin, an amphipathic lipid and an extended amphipathic lipid. The extended amphipathic lipid molecule comprises proximal, medial and distal moieties. The proximal moiety connects the extended lipid to the construct. The distal moiety targets the construct to a receptor displayed by a hepatocyte, and the medial moiety connects the proximal and distal moieties.

The invention also provides a method of manufacturing a composition comprising free insulin and insulin associated with a water insoluble target molecule complex within the lipid construct that targets delivery of the complex to hepatocytes. The target molecule complex comprises a lipid construct matrix containing multiple linked individual units of a structure formed by a metal complex.

Additionally, the invention provides methods of treating individuals afflicted with diabetes by administering an effective dose of a lipid construct comprising insulin, an amphipathic lipid and an extended amphipathic lipid, targeted for delivery to hepatocytes.

The invention also provides methods of treating individuals afflicted with diabetes by administering an effective dose of a lipid construct comprising insulin, an amphipathic lipid, an extended amphipathic lipid and a water insoluble target molecule complex, targeted for delivery to hepatocytes.

The invention also provides methods of treating a patient with insulin to which a polar organic compound, or mixture of compounds, is bound, thereby changing the isoelectric point of insulin. This change in the isoelectric point will change the release of insulin into the body of patient treated with the composition.

Additionally, the invention provides methods of managing blood glucose levels in individuals with Type I and Type II diabetes by administering an effective dose of a hepatocyte targeted pharmaceutical composition that combines free insulin and insulin associated with a water insoluble target molecule complex targeted for delivery to hepatocytes. The combination of free insulin and insulin associated with a water insoluble target molecule complex creates a dynamic equilibrium process between the two forms of insulin that occurs in vivo to help control the movement of free insulin to the receptor sites of hormonal action, such as the muscle and adipose tissue of a diabetic patient over a designated time period. Hepatocyte targeted insulin is also delivered to the liver of a diabetic patient over a different designated time period than free insulin thereby introducing new pharmacodynamic profiles of insulin when free insulin is released from the lipid construct. In addition, a portion of insulin that is associated with the lipid construct is targeted to the liver. This new pharmacodynamic profile of the product provides not only long-acting basal insulin for peripheral tissues, but also meal-time hepatic insulin stimulation for the management of hepatic glucose storage during a meal. Free insulin is released from the site of administration and is distributed throughout the body. Insulin associated with a water insoluble target molecule complex is delivered to the liver, where it is released over time from the complex. The rate of release of insulin associated with the target molecule complex is different than the rate of release of free insulin from the site of administration. These different release rates of insulin delivery, combined with the targeted delivery of insulin associated with a lipid construct to the liver, provide for the normalization of glucose concentrations in patients with Type I and Type II diabetes. The hepatocyte targeted composition can also comprise other types of insulin, or a combination of other types of insulin.

Definitions

Unless defined otherwise, all technical and scientific terms used herein generally have the same meaning as commonly understood by one of ordinary skill in the art to which the invention belongs. Generally, the nomenclature used herein and the laboratory procedures in organic chemistry and protein chemistry are those well known and commonly employed in the art.

The articles "a" and "an" are used herein to refer to one or to more than one (i.e., to at least one) of the grammatical object of the article. By way of example, "an element" means one element or more than one element.

The term "active ingredient" refers to recombinant human insulin isophane, recombinant human regular insulin and other insulins.

As used herein, amino acids are represented by the full name thereof, by the three-letter code as well as the one-letter code corresponding thereto, as indicated in the following table:

| Full Name | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "lower" means the group it is describing contains from 1 to 6 carbon atoms.

The term "alkyl", by itself or as part of another substituent means, unless otherwise stated, a straight, branched or cyclic chain hydrocarbon having the number of carbon atoms designated (i.e. $C_1$-$C_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$) alkyl, particularly ethyl, methyl and isopropyl.

The term "alkylene", by itself or as part of another substituent means, unless otherwise stated, a straight, branched or cyclic chain hydrocarbon having two substitution sites, e. g., methylene (—$CH_2$—), ethylene (—$CH_2CH_2$—), isopropylene (—$CH(CH_3)$=$CH_2$), etc.

The term "aryl", employed alone or in combination with other terms, means, unless otherwise stated, a cyclic carbon ring structure, with or without saturation, containing one or more rings (typically one, two or three rings) wherein such rings may be attached together in a pendant manner, such as a biphenyl, or may be fused, such as naphthalene. Examples include phenyl; anthracyl; and naphthyl. The structure can have one or more substitution sites where functional groups, such as alcohol, alkoxy, amides, amino, cyanides, halogen, and nitro, are bound.

The term "arylloweralkyl" means a functional group wherein an aryl group is attached to a lower alkylene group, e.g., —$CH_2CH_2$-phenyl.

The term "alkoxy" employed alone or in combination with other terms means, unless otherwise stated, an alkyl group or an alkyl group containing a substituent such as a hydroxyl group, having the designated number of carbon atoms connected to the rest of the molecule via an oxygen atom, such as, for example, —OCHOH—, —OCH$_2$OH, methoxy (—OCH$_3$), ethoxy (—OCH$_2$CH$_3$), 1-propoxy (—OCH$_2$CH$_2$CH$_3$), 2-propoxy (isopropoxy), butoxy (—OCH$_2$CH$_2$CH$_2$CH$_3$), pentoxy (—OCH$_2$CH$_2$CH$_2$CH$_2$CH$_3$), and the higher homologs and isomers.

The term "acyl" means a functional group of the general formula —C(═O)—R, wherein —R is hydrogen, hydrocarbyl, amino or alkoxy. Examples include acetyl (—C(═O)CH$_3$), propionyl (—C(═O)CH$_2$CH$_3$), benzoyl (—C(═O)C$_6$H$_5$), phenylacetyl (—C(═O)CH$_2$C$_6$H$_5$), carboethoxy (—CO$_2$CH$_2$CH$_3$), and dimethylcarbamoyl (—C(═O)N(CH$_3$)$_2$).

The terms "halo" or "halogen" by themselves or as part of another substituent mean, unless otherwise stated, a fluorine, chlorine, bromine, or iodine atom.

The term "heterocycle" or "heterocyclyl" or "heterocyclic" by itself or as part of another substituent means, unless otherwise stated, an unsubstituted or substituted, stable, mono- or multicyclic heterocyclic ring system comprising carbon atoms and at least one heteroatom selected from the group comprising N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure. Examples include pyrrole, imidazole, benzimidazole, phthalein, pyridenyl, pyranyl, furanyl, thiazole, thiophene, oxazole, pyrazole, 3-pyrroline, pyrrolidene, pyrimidine, purine, quinoline, isoquinoline, carbazole, etc.

The term "chromium target molecule complex" refers to a complex comprising a number of individual units, where each unit comprises chromium (Cr) atoms capable of accepting up to six ligands contributed by multivalent molecules, such as ligands from numerous molecules of N-(2,6-diisopropylphenylcarbamoyl methyl) iminodiacetic acid. The individual units are linked to each other forming a complicated polymeric structure linked in a three-dimensional array. The polymeric complex is insoluble in water but soluble in organic solvents.

The term "lipid construct" refers to a lipid and/or phospholipid particle in which individual lipid molecules cooperatively interact to create a bipolar lipid membrane which encloses and isolates a portion of the medium in which the construct resides.

The term "amphipathic lipid" means a lipid molecule having a polar and non-polar end.

The term "extended amphipathic lipid" means an amphipathic molecule with a structure that, when part of a lipid construct, extends from the lipid construct into media around the construct, and can bind or interact with a receptor.

A "complexing agent" is a compound that will form a polymeric complex with a selected metal bridging agent, e.g. a salt of chromium, zirconium, etc., that exhibits polymeric properties where the polymeric complex is substantially insoluble in water and soluble in organic solvents.

By "aqueous media" is meant water or water containing buffer or salt.

By "substantially soluble" is meant that the material, such as the resultant polymeric chromium target molecule complex or other metal targeting complexes which may be crystalline or amorphous in composition that are formed from complexing agents, exhibit the property of being insoluble in water at room temperature. Such a polymeric complex or a dissociated form thereof when associated with a lipid construct matrix forms a transport agent which functions to carry and deliver insulin to hepatocytes in the liver of a warm-blooded host.

By "substantially insoluble" is meant that a polymeric complex, such as a polymeric chromium target molecule complex or other metal targeting complexes, exhibits the property of being insoluble in water at room temperature. Such a polymeric complex, which may be crystalline, amorphous in composition, or a dissociated form thereof, when associated with a lipid construct forms a transport agent that carries and delivers insulin to hepatocytes in the liver.

By use of the term "associated with" is meant that the referenced material is incorporated into or on the surface of, or within, the lipid construct matrix.

The term "insulin" refers to natural or recombinant forms of insulin, and derivatives of the aforementioned insulins. Examples of insulin include, but are not limited to insulin lispro, insulin aspart, regular insulin, insulin glargine, insulin zinc, human insulin zinc extended, isophane insulin, human buffered regular insulin, insulin glulisine, recombinant human regular insulin, and recombinant human insulin isophane. Also included are animal insulins, such as bovine or porcine insulin.

The term "free insulin" refers to an insulin that is not associated with a target molecule complex.

Figure 11:
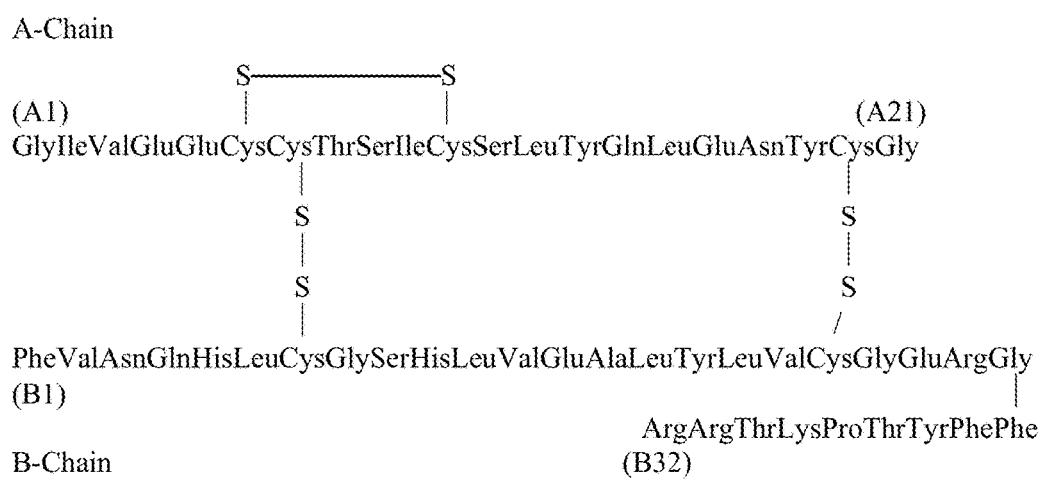
FIG. 11 is a depiction of the chemical structure of glargine insulin.

The terms "glargine" and "glargine insulin" both refer to a recombinant human insulin analog which differs from human insulin in that the amino acid asparagine at position A21 is replaced by glycine and two arginines are added to the C-terminus of the B-chain. Chemically, it is 21$^A$-Gly-30$^B$a-L-Arg-30$^B$b-L-Arg-human insulin and has the empirical formula C$_{267}$H$_{404}$N$_{72}$O$_{78}$S$_6$ and a molecular weight of 6063. The structural formula of glargine insulin is provided in FIG. 11.

The term "non-glargine insulin" refers at all insulins, either natural or recombinant that are not glargine insulin. The term includes insulin-like moieties, including fragments of insulin molecules, that have biological activity of insulins.

The term "recombinant human insulin isophane" refers to a human insulin that has been treated with protamine. The structural formulas for recombinant human insulin isophane and protamine are provided in FIG. 12.

The term "at least one insulin that is not recombinant human insulin isophane insulin" refers at all insulins, either natural or recombinant, that are not recombinant human insulin isophane. The term includes insulin-like moieties, including fragments of insulin molecules that have biological activity of insulins.

"HDV", or "Hepatocyte Delivery Vehicle", is a water insoluble target molecule complex comprising a lipid construct matrix containing multiple linked individual units of a structure formed by the combination of a metal bridging agent and a complexing agent. "HDV" is described in WO 99/59545, Targeted Liposomal Drug Delivery System.

"HDV-glargine" is a designation for a hepatocyte targeted composition comprising a mixture of free glargine insulin and glargine insulin associated with a water insoluble target molecule complex, wherein the complex comprises multiple linked individual units of chromium and N-(2,6-diisopropylphenylcarbamoylmethyl) iminodiacetic acid, formed by the combination of a metal bridging agent and a complexing agent, and a lipid construct matrix.

"HDV-NPH" is a designation for a hepatocyte targeted composition comprising a mixture of free recombinant human insulin isophane, free non-humulin insulin, and recombinant human insulin isophane and non-humulin insulin that are associated with a water insoluble target molecule complex, wherein the complex comprises multiple linked individual units of chromium and N-(2,6-diisopropylphenylcarbamoylmethyl) iminodiacetic acid, formed by the combination of a metal bridging agent and a complexing agent, and a lipid construct matrix.

The term "bioavailability" refers to a measurement of the rate and extent that insulin reaches the systemic circulation and is available at the sites of action.

The term "isoelectric point" refers to the pH at which the concentrations of positive and negative charges on the protein are equal and, as a result, the protein will express a net zero charge. At the isoelectric point, a protein will exist almost entirely in the form of a zwitterion, or hybrid between forms of the protein. Proteins are least stable at their isoelectric points, and are more easily coagulated or precipitated at this pH. However, proteins are not denatured upon isoelectric precipitation since this process is essentially reversible.

As the term is used herein, "to modulate" or "modulation of" a biological or chemical process or state refers to the alteration of the normal course of the biological or chemical process, or changing the state of the biological or chemical process to a new state that is different than the present state. For example, modulation of the isoelectric point of a polypeptide may involve a change that increases the isoelectric point of the polypeptide. Alternatively, modulation of the isoelectric point of a polypeptide may involve a change that decreases the isoelectric point of a polypeptide.

"Statistical structure" denotes a structure formed from molecules that can migrate from one lipid construct to another and the structure is present in a plurality of particle sizes that can be represented by a Gaussian distribution.

"Multi-dentate binding" is a chemical binding process that utilizes multiple binding sites within the lipid construct, such as cellulose acetate hydrogen phthalate, phospholipids and insulin. These binding sites promote hydrogen bonding, ion-dipole and dipole-dipole interactions where the individual molecules work in tandem to form non-covalent associations that serve to bind or connect two or more molecules.

As used herein, to "treat" means reducing the frequency with which symptoms of a disease, disorder, or adverse condition, and the like, are experienced by a patient.

As used herein, the term "pharmaceutically acceptable carrier" means a chemical composition with which the active ingredient may be combined and which, following the combination, can be used to administer the active ingredient to a subject.

As used herein, the term "physiologically acceptable" means that the ingredient is not deleterious to the subject to which the composition is to be administered.

Description of the Invention—Composition
Lipid Construct

A depiction of an insulin binding lipid construct comprising insulin, an amphipathic lipid and an extended amphipathic lipid is shown in FIG. 1. The extended amphipathic lipid, also known as a receptor binding molecule, comprises proximal, medial and distal moieties, wherein the proximal moiety connects the extended lipid molecule to the construct, the distal moiety targets the construct to a receptor displayed by a hepatocyte, and the medial moiety connects the proximal and distal moieties. Suitable amphipathic lipids generally comprise a polar head group and non-polar tail group that are attached to each other through a glycerol-backbone.

Suitable amphipathic lipids include 1,2-distearoyl-sn-glycero-3-phosphocholine, 1,2-dipalmitoyl-sn-glycero-3-phosphocholine, 1,2-dimyristoyl-sn-glycero-3-phosphocholine, cholesterol, cholesterol oleate, dicetyl phosphate, 1,2-distearoyl-sn-glycero-3-phosphate, 1,2-dipalmitoyl-sn-glycero-3-phosphate, 1,2-dimyristoyl-sn-glycero-3-phosphate, 1,2-dipalmitoyl-sn-glycero-3-phosphoethanolamine-N-(Cap Biotinyl), 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), triethylammonium 2,3-diacetoxypropyl 2-(5-((3aS,6aR)-2-oxohexahydro-1H-thieno[3,4-d]imidazol-4-yl) pentanamido)ethyl phosphate and a mixture of any of the foregoing lipids or appropriate derivative of these lipids.

In an embodiment, amphipathic lipid molecules include 1,2-distearoyl-sn-glycero-3-phosphocholine, cholesterol, dicetyl phosphate, 1,2-dipalmitoyl-sn-glycero-3-phosphoethanolamine-N-(Cap Biotinyl); 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), triethylammonium 2,3-diacetoxypropyl 2-(5-((3aS,6aR)-2-oxohexahydro-1H-thieno[3,4-d]imidazol-4-yl) pentanamido)ethyl phosphate and a mixture of any of the foregoing lipids.

The extended amphipathic lipid molecule, also know as a receptor binding molecule, comprises proximal, medial and distal moieties. The proximal moiety connects the extended lipid molecule to the construct, and the distal moiety targets the construct to a receptor displayed by a hepatocyte. The proximal and distal moieties are connected through a medial moiety. The composition of various receptor binding molecules is described below. Within a lipid construct, hepatocyte receptor binding molecules from one or more of the groups listed below can be present to bind the construct to receptors in the hepatocytes.

One group of hepatocyte receptor binding molecules comprises a terminal biotin or iminobiotin moiety, as well as derivatives thereof. The structural formulas of biotin, iminobiotin, carboxybiotin and biocytin are shown in Table 1.

TABLE 1

| 1 | 1,2-distearoyl-sn-glycero-3-phosphocholine 2,3-bis(stearoyloxy)propyl 2-(trimethylammonio)ethyl phosphate | 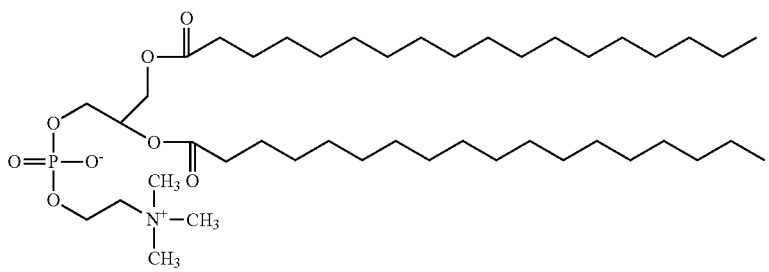 |

TABLE 1-continued

| | | |
|---|---|---|
| 2 | 1,2-dipalmitoyl-sn-glycero-3-phosphocholine 2,3-bis(palmitoyloxy)propyl 2-(trimethylammonio)ethyl phosphate | 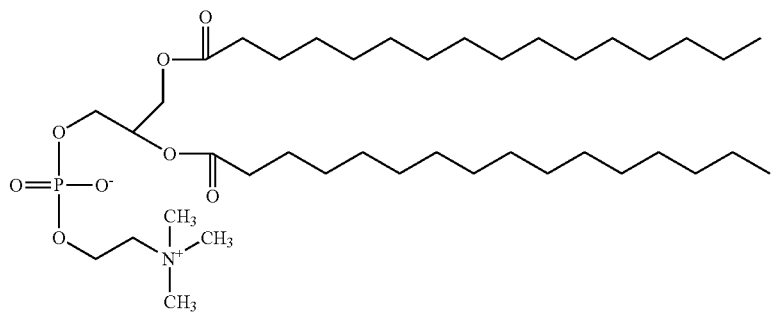 |
| 3 | 1,2-dimyristoyl-sn-glycero-3-phosphocholine 2,3-bis(tetradecanoyloxy) propyl 2-(trimethylammonio) ethyl phosphate | 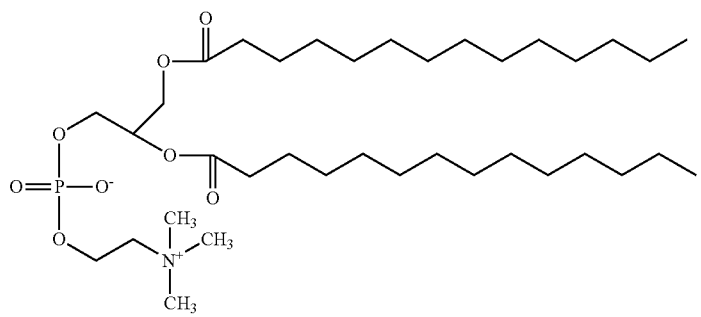 |
| 4 | Cholesterol 10,13-dimethyl-17-(6-methylheptan-2-yl)-2,3,4,7,8,9,10,11,12,13,14,15,16,17-tetradecahydro-1H-cyclopenta[a]phenanthren-3-ol | 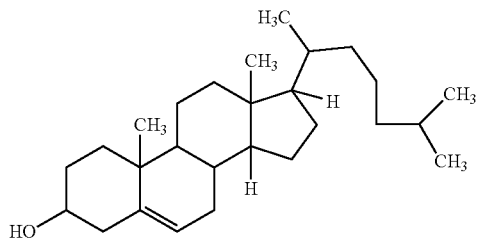 |

These molecules can be attached to a phospholipid molecule using a variety of techniques to create lipid anchoring molecules that can be intercalated into a lipid construct. These hepatocyte receptor binding molecules comprise an anchoring portion located in the proximal position to the lipid construct. The anchor portion comprises two lipophilic hydrocarbon chains that can associate and bind with other lipophilic hydrocarbon chains on phospholipid molecules within the lipid construct.

In a preferred embodiment, a second group of hepatocyte receptor binding molecules comprises a terminal biotin or iminobiotin moiety located in the distal position from the lipid construct. The structures of such compounds are given in Table 2.

TABLE 2

| | | |
|---|---|---|
| 1 | Biotin 5-((3aS,6aR)-2-oxohexahydro-1H-thieno[3,4-d]imidazol-4-yl)pentanoic acid | 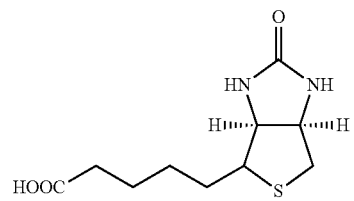 |
| 2 | Iminobiotin 5-((3aS,6aR)-2-iminohexahydro-1H-thieno[3,4-d] imidazol-4-yl) pentanoic acid |  |

TABLE 2-continued

| 3 | Carboxybiotin 5-((3aS,6aR)-1-(carboxymethyl)-2-oxohexahydro-1H-thieno[3,4-d]imidazol-4-yl)pentanoic acid | 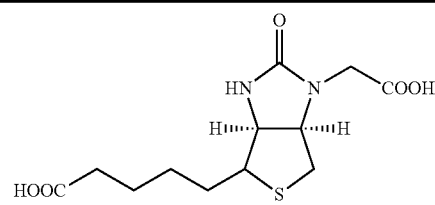 |
| --- | --- | --- |
| 4 | Biocytin 2-amino-6-(5-((3aS,6aR)-2-oxohexahydro-1H-thieno[3,4-d]imidazol-4-yl)pentanamido)hexanoic acid | 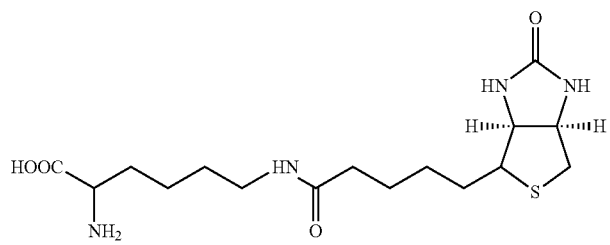 [SMILES: NC(CCCCNC(=O)CCCCC1SC[C@@H]2NC(=O)N[C@H]12)C(=O)O] |

Figure 2:
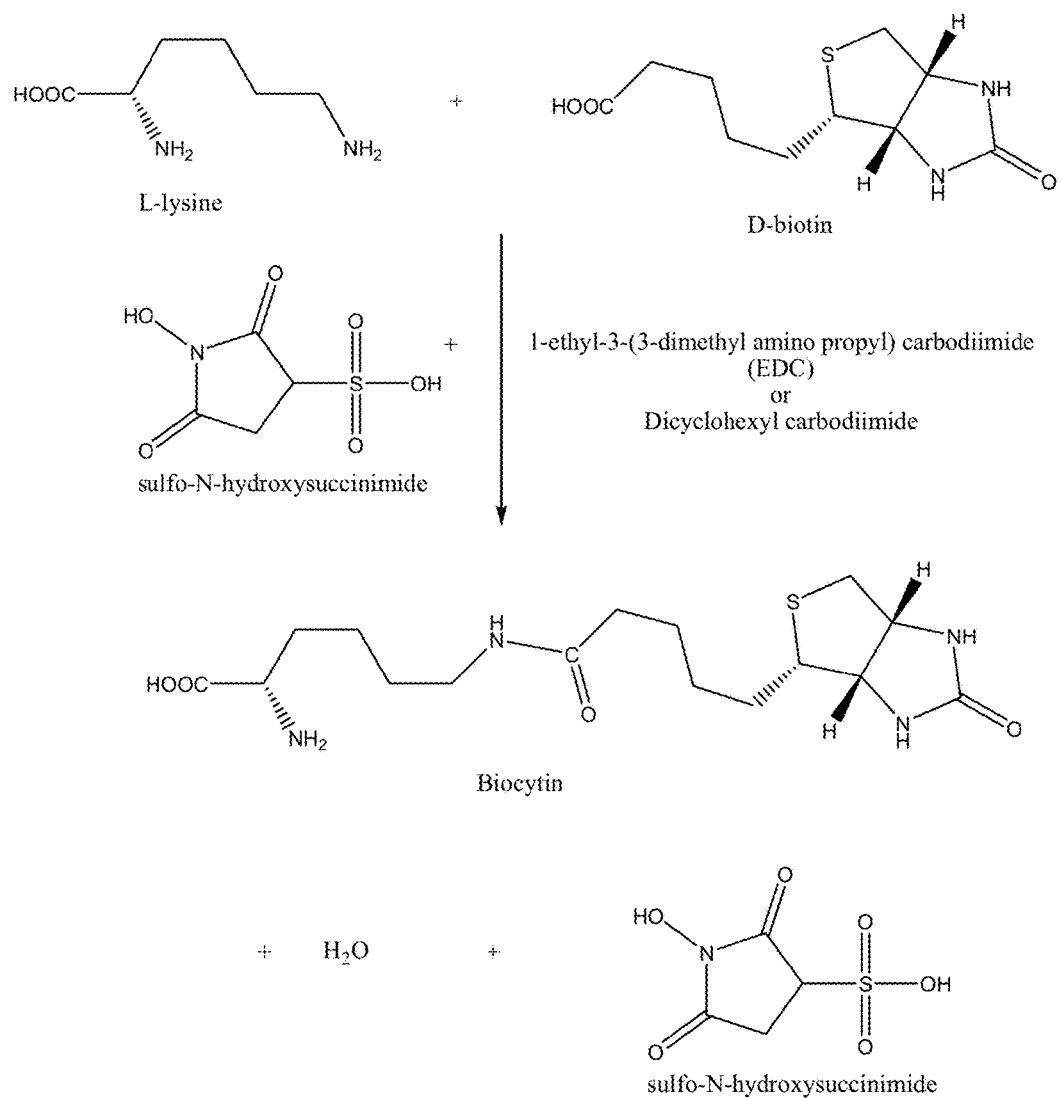
FIG. 2 is depiction of a route for manufacturing biocytin.

Both biotin and iminobiotin contain a mildly lipophilic bicyclic ring structure attached to a five-carbon valeric acid chain at the 4-carbon position on the bicyclic ring. In an embodiment, L-lysine amino acid may be covalently bound to the valeric acid C-terminal carboxyl functional group by reacting the carboxyl group on valeric acid with either the N-terminal α-amino group or the ε-amino group of L-lysine. This coupling reaction is performed using carbodiimide conjugation methods and results in the formation of an amide bond between L-lysine and biotin, as illustrated in FIG. 2.

Figure 3:
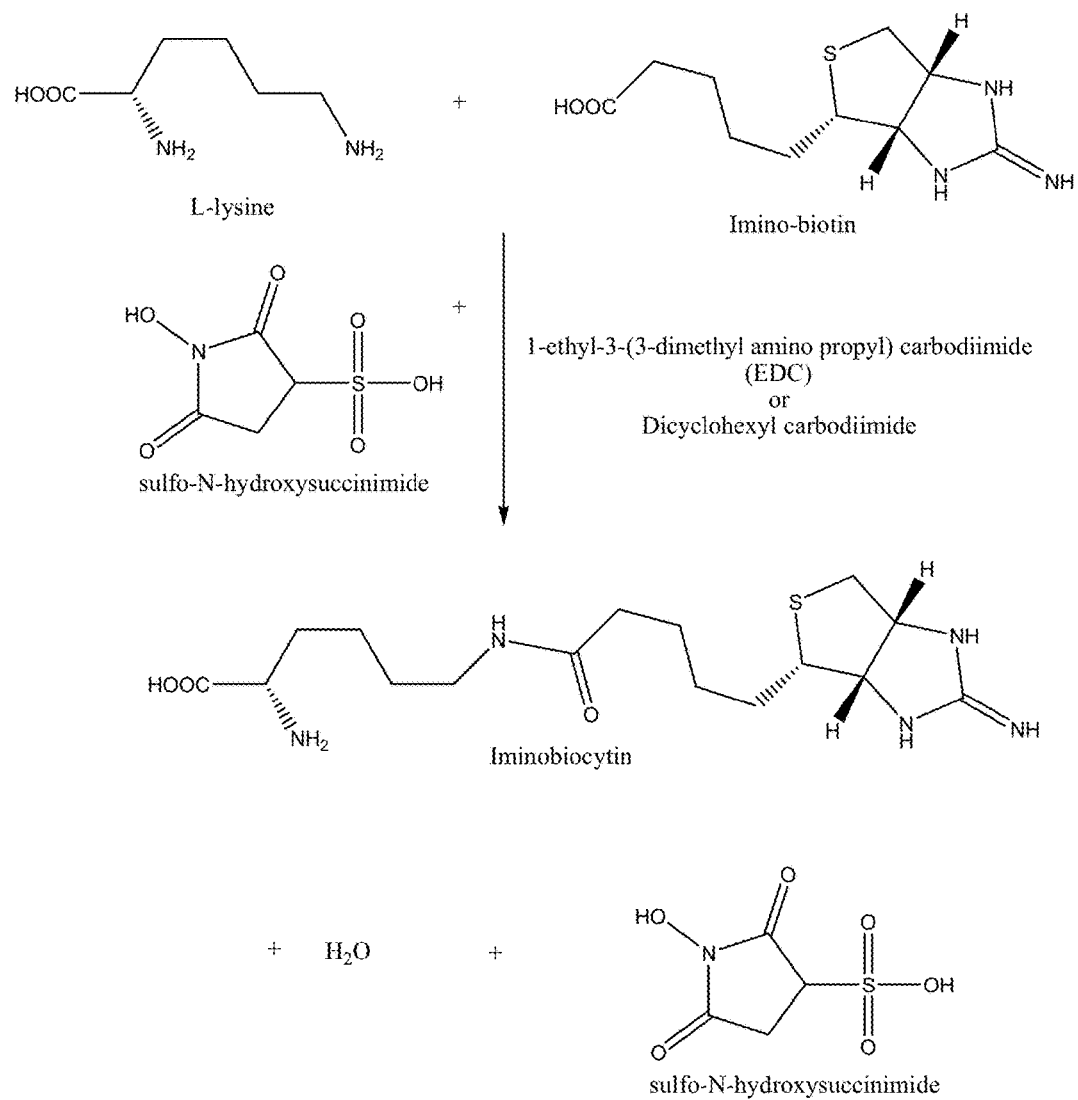
FIG. 3 is a depiction of a route for manufacturing iminobiocytin.
Figure 4:
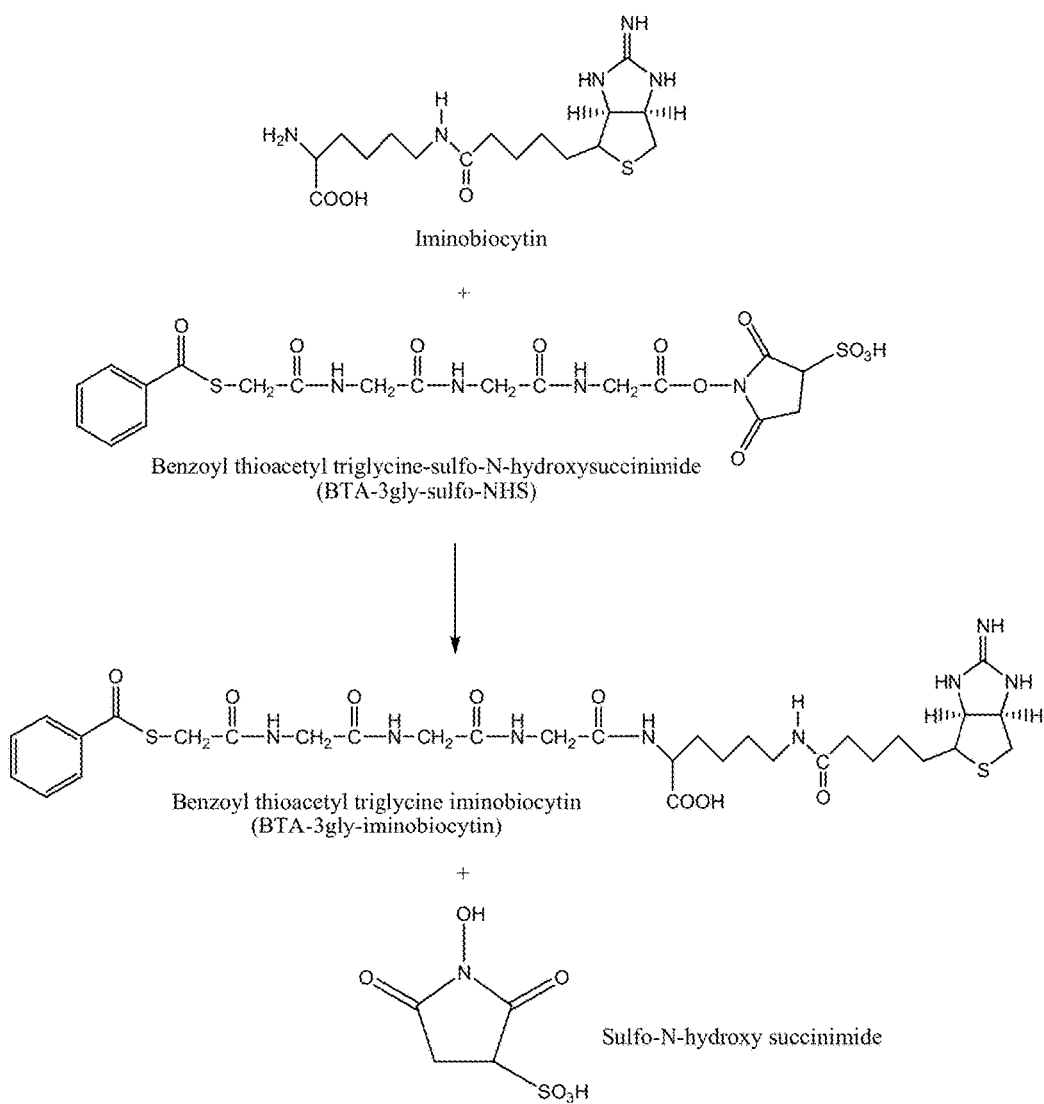
FIG. 4 is a depiction of a route for manufacturing benzoyl thioacetyl triglycine iminobiocytin (BTA-3gly-iminobiocytin).

A third group of hepatocyte receptor binding molecules comprise iminobiotin, carboxybiotin and biocytin with the valeric acid side chain attached via an amide bond to either the α-amino group or the ε-amino group of the amino acid L-lysine. A preferred embodiment uses iminobiotin in forming an iminobiocytin moiety as shown in FIG. 3. During synthesis of the hepatocyte receptor binding molecule, the α-amino group of iminobiocytin can react with the activated ester benzoyl thioacetyl triglycine-sulfo-N-hydroxysuccinimide (BTA-3gly-sulfo-NHS) to form the active hepatocyte binding molecule (BTA-3gly-iminobiocytin) as shown in FIG. 4. BTA-3gly-iminobiocytin functions as a molecular spacer that ultimately expresses an active nucleophilic sulfhydral functional group that can be used in subsequent coupling reactions. The spacer is located in the medial position in relation to the lipid construct and allows the terminal iminobiocytin moiety to extend approximately thirty angstroms from the surface of the lipid construct to develop an optimal and non-restricted orientation of iminobiocytin for binding to the hepatocyte receptor. The medial spacer can include other derivatives that provide the correct stereo-chemical orientation for the terminal biotin moiety. The main function of the medial spacer is to properly and covalently connect the proximal and distal moieties in a linear array.

Figure 5:
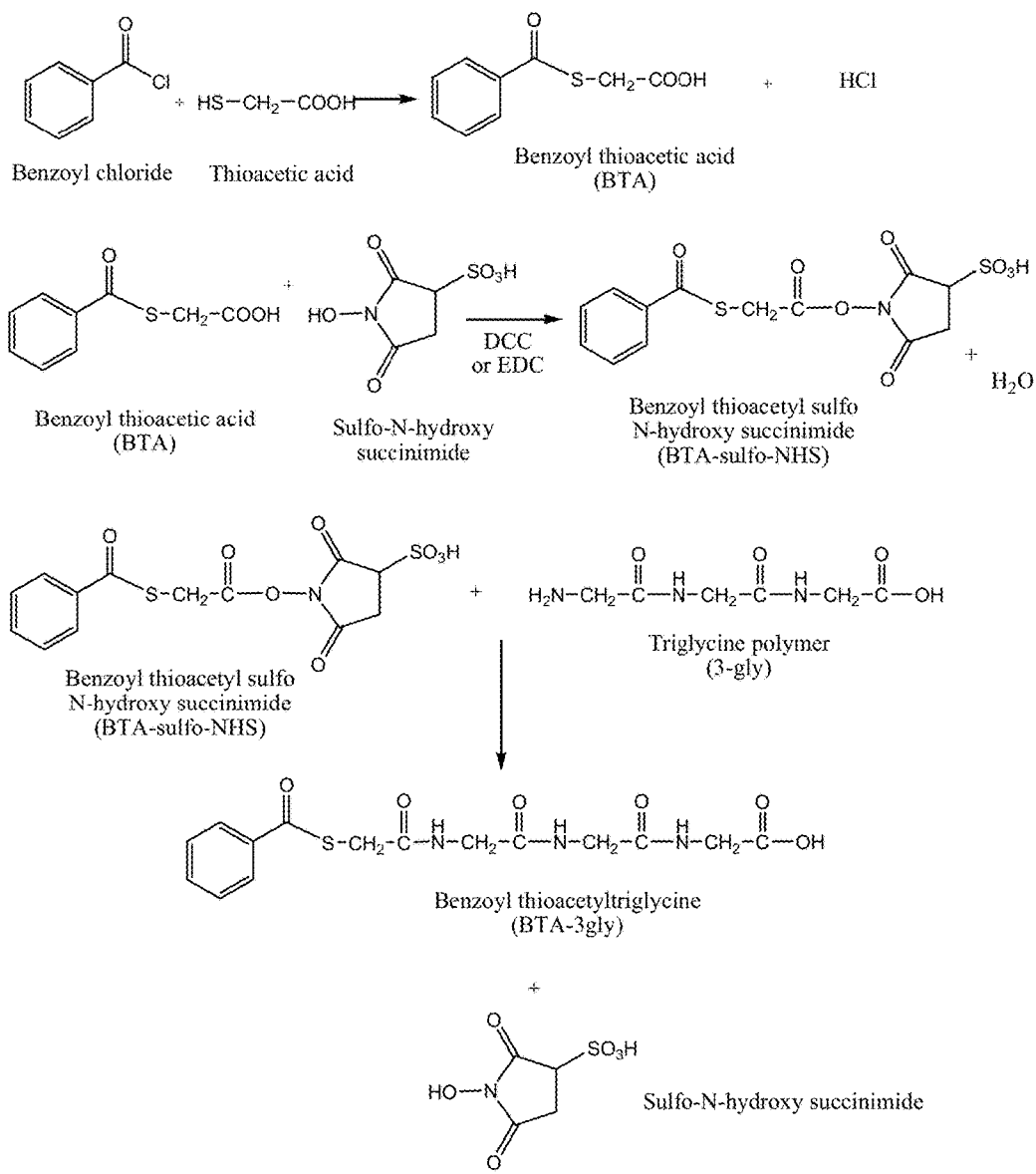
FIG. 5 is a depiction of a route for manufacturing benzoyl thioacetyl triglycine.
Figure 6:
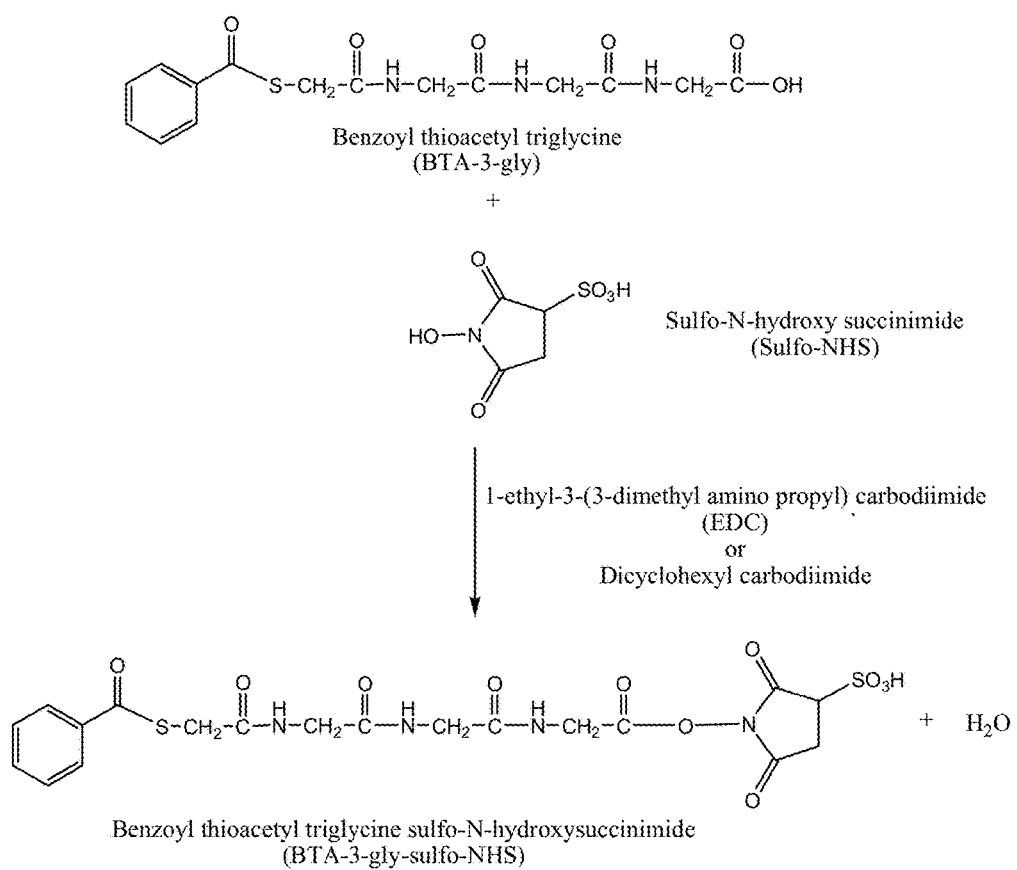
FIG. 6 is a depiction of a route for manufacturing benzoyl thioacetyl triglycine sulfo-N-hydroxysiccinimide (BTA-3-gly-sulfo-NHS).
Figure 7:
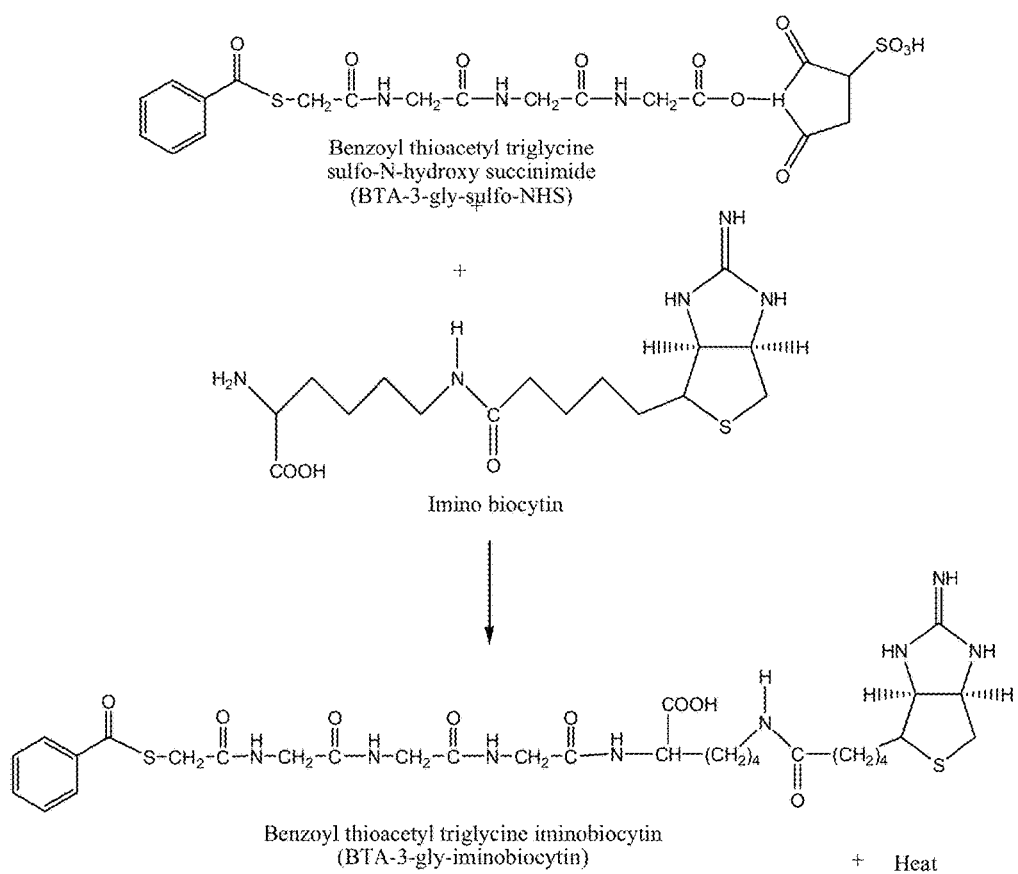
FIG. 7 is a depiction of a route for manufacturing benzoyl thioacetyl triglycine iminobiocytin (BTA-3-gly-iminobiocytin).

The BTA-3gly-sulfo-NHS portion of the hepatocyte receptor binding molecule can be synthesized by a number of means and in subsequent steps be linked to biocytin or iminobiocytin. The initial step comprises adding benzoyl chloride to thioacetic acid to form by nucleophilic addition a protective group for the active thio functionality. The products of the reaction are the benzoyl thioacetic acid complex and hydrochloric acid, as shown in FIG. 5. Additional steps in the synthesis involve reacting benzoyl thioacetic acid with sulfo-N-hydroxysuccinimide using dicyclohexylcarbodiimide or 1-ethyl-3-(3-dimethylaminopropyl) carbodiimide as a coupling agent to form benzoyl thioacetyl sulfo-N-hydroxysuccinimide (BTA-sulfo-NHS), as depicted in FIG. 5. Benzoyl thioacetyl sulfo-N-hydroxysuccinimide is then reacted with the amino acid polymer (glycine-glycine-glycine). Following nucleophilic attack by the α-amino group of triglycine, benzoyl thioacetyl triglycine (BTA-3gly) is formed while the sulfo-N-hydroxysuccinimide leaving group is solubilized by aqueous media, as shown in FIG. 5. Benzoyl thioacetyl triglycine is again reacted with dicyclohexylcarbodiimide or 1-ethyl-3-(3-dimethylamino-propyl) carbodiimide to form an ester bond with sulfo-N-hydroxysuccinimide, as shown in FIG. 6. The sulfo-N-hydroxysuccinimide ester of activated benzoyl thioacetyl triglycine (BTA-3gly-sulfo-NHS) is then reacted with the α-amino group of the L-lysine functionality of biocytin or iminobiocytin to form the hepatocyte receptor binding moiety, the extended amphipathic lipid molecule of benzoyl thioacetyl triglycine-iminobiocytin (BTA-3gly-iminobiocytin) illustrated in FIG. 7.

Figure 8:
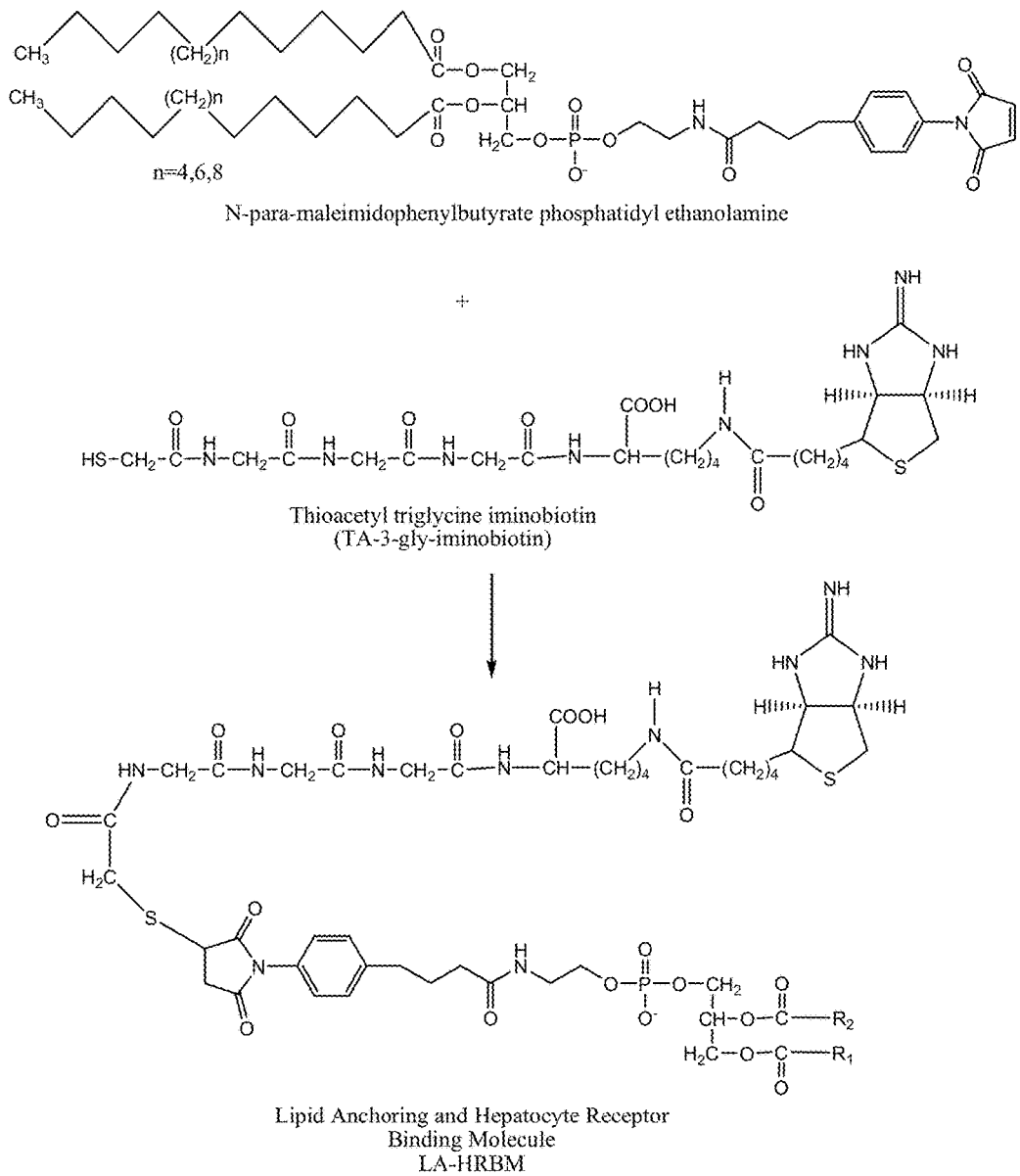
FIG. 8 is a depiction of a route for manufacturing a lipid anchoring and hepatocyte receptor binding molecule (LA-HRBM).

A second major coupling reaction for the synthesis of an hepatocyte receptor binding molecule is illustrated where benzoyl thioacetyl triglycine iminobiocytin is covalently attached through a thioether bond to a N-para-maleimidophenylbutyrate phosphatidylethanolamine, a preferred phospholipid anchoring molecule. This reaction results in a molecule that provides the correct molecular spacing between the terminal iminobiocytin ring and the lipid construct. An entire reaction scheme for forming a hepatocyte receptor binding molecule that functions as an extended amphipathic lipid molecule is depicted in FIG. 8. Prior to reacting benzoyl thioacetyl triglycine iminobiocytin with N-para-maleimidophenylbutyrate phosphatidylethanolamine to form a thioether linkage, the benzoyl protecting group is removed by heating in order to expose the free sulfhydral functionality. The reaction should be performed in an oxygen free environment to minimize oxidation of the sulfhydrals to the disulfide. Further oxidation could lead to the formation of a sulfone, sulfoxide, sulfenic acid or sulfonic acid derivative.

In an embodiment, the anchoring moiety of the molecule contains a pair of acyl hydrocarbon chains that form a lipid portion of the molecule. This portion of the molecule is non-covalently bound within the lipid domains of the lipid construct. In an embodiment the anchoring moiety is produced from is N-para-maleimidophenylbutyrate phosphatidylethanolamine. Other anchoring molecules may be used. In an embodiment, anchoring molecules can include thiocholesterol, cholesterol oleate, dicetyl phosphate; 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), and mixtures, thereof. The entire molecular structure of the fully developed lipid anchoring and hepatocyte receptor binding molecule designated LA-HRBM is shown in FIG. 8.

A fourth group of hepatocyte receptor binding molecule comprises amphipathic organic molecules having both a water-soluble moiety and a water-insoluble moiety. The water-insoluble moiety reacts with a medial or connector moiety by coordination and bioconjugation chemical reactions, while the water-insoluble moiety binds to the hepatocyte binding receptor in the liver. The molecule contains a distal component comprising either by a non-polar derivatized benzene ring structure, such as a 2,6-diisopropylbenzene derivative, or by a lipophilic heterobicyclic ring structure. The entire hepatocyte receptor binding molecule possesses fixed or transient charges, either positive or negative, or various combinations thereof. These molecules contain at least one carbonyl group located equal to or less than, but not greater than, approximately 13.5 angstroms from the terminal end of the distal moiety, and at least one carbamoyl moiety containing a secondary amine and carbonyl group. The presence of a carbamoyl moiety or moieties enhances the molecular stability of the organic molecule. A plurality of secondary amines can be present within the molecule. These secondary amines contain a pair of unshared electrons allowing for ion-dipole and dipole-dipole bonding interactions with other molecules within the construct. These amines enhance molecular stability and provide a partially created negative charge that interacts with the distal moiety to promote hepatocyte receptor binding and specificity. An example of this group of receptor binding molecules is polychromium-poly(bis)-[N-(2,6-(diisopropylphenyl)carbamoyl methyl)imino diacetic acid]. In an embodiment, chromium III is located in the medial position of the hepatocyte receptor binding molecule. The proximal moiety of the hepatocyte specific binding molecule contains hydrophobic and/or non-polar structures that allow the molecules to be intercalated into, and subsequently bound within, the lipid construct. The medial and proximal moieties also allow for the correct stereo-chemical orientation of the distal portion of the hepatocyte receptor binding molecule.

The structure and properties of the lipid construct are governed by the structure of the lipids and interaction between lipids. The structure of the lipids is governed primarily by covalent bonding. Covalent bonding is the molecular bonding force necessary to retain the structural integrity of the molecules comprising the individual constituents of the lipid construct. Through non-covalent interactions between lipids, the lipid construct is maintained in a three-dimensional conformation.

The non-covalent bond can be represented in general terms by an ion-dipole or induced ion-dipole bond, and by the hydrogen bonds associated with the various polar groups on the head of the lipid. Hydrophobic bonds and van der Waal's interactions can be generated through induced dipole associations between the lipid acyl chains. These bonding mechanisms are transient in nature and result in a bond-making and bond breaking process that occurs in a sub-femtosecond time interval. For example, van der Waal's interaction arises from a momentary change in dipole moment arising from a brief shift of orbital electrons to one side of one atom or molecule, creating a similar shift in adjacent atoms or molecules. The proton assumes a $\delta^+$ charge and the single electron a $\delta^-$ charge, thus forming a dipole. Dipole interactions occur with great frequency between the hydrocarbon acyl chains of amphipathic lipid molecules. Once individual dipoles are formed they can momentarily induce new dipole formation in neighboring atoms containing a methylenic (—$CH_2$—) functionality. A plurality of transiently induced dipole interactions are formed between acyl lipid chains throughout the lipid construct. These induced dipole interactions last for only a fraction of a femtosecond ($1 \times 10^{-15}$ sec) but exert a strong force when functioning collectively. These interactions are constantly changing and have a force approximately one-twentieth the strength of a covalent bond. They are nevertheless responsible for transient bonding between stable covalent molecules that determine the three-dimensional statistical structure of the construct and the stereo-specific molecular orientation of molecules within the lipid construct.

As a consequence of these induced-dipole interactions, the structure of the lipid construct is maintained by the exchange of lipid components between constructs. While the composition of the individual components of the construct is fixed, individual components of lipid constructs are subject to exchange reactions between constructs. These exchanges are initially governed by zero-order kinetics when a lipid component departs from a lipid construct. After the lipid component is released from the lipid construct, it may be recaptured by a neighboring lipid construct. The recapture of the released component is controlled by second-order reaction kinetics, which is affected by the concentration of the released component in aqueous media around the construct capturing the component and the concentration of the lipid construct which is capturing the released component.

Examples of extended amphipathic lipids, along with their respective identifiers, shown in Table 3 along with their chemical names, are: N-hydroxysuccinimide (NHS) biotin [1]; sulfo-NHS-biotin [2]; N-hydroxysuccinimide long chain biotin [3], sulfo-N-hydroxysuccinimide long chain biotin [4]; D-biotin [5]; biocytin [6]; sulfo-N-hydroxysuccinimide-S—S-biotin [7]; biotin-BMCC [8]; biotin-HPDP [9]; iodoacetyl-LC-biotin [10]; biotin-hydrazide [11]; biotin-LC-hydrazide [12]; biocytin hydrazide [13]; biotin cadaverine [14]; carboxybiotin [15]; photobiotin [16]; ρ-aminobenzoyl biocytin trifluoroacetate [17]; ρ-diazobenzoyl biocytin [18]; biotin DHPE [19]; biotin-X-DHPE [20]; 12-((biotinyl)amino)dodecanoic acid [21]; 12-((biotinyl)amino)dodecanoic acid succinimidyl ester [22]; S-biotinyl homocysteine [23]; biocytin-X [24]; biocytin x-hydrazide [25]; biotinethylenediamine [26]; biotin-XL [27]; biotin-X-ethylenediamine [28]; biotin-XX hydrazide [29]; biotin-XX-SE [30]; biotin-XX, SSE [31]; biotin-X-cadaverine [32]; α-(t-BOC)biocytin [33]; N-(biotinyl)-N'-(iodoacetyl)ethylenediamine [34]; DNP-X-biocytin-X-SE [35]; biotin-X-hydrazide [36]; norbiotinamine hydrochloride [37]; 3-(N-maleimidylpropionyl) biocytin [38]; ARP [39]; biotin-1-sulfoxide [40]; biotin methyl ester [41]; biotin-maleimide [42]; biotin-poly(ethyleneglycol)amine [43]; (+) biotin 4-amidobenzoic acid sodium salt [44]; Biotin 2-N-acetylamino-2-deoxy-β-D-glucopyranoside [45]; Biotin-α-D-N-acetylneuraminide [46]; Biotin-α-L-fucoside [47]; Biotin lacto-N-bioside [48]; Biotin-Lewis-A trisaccharide [49]; Biotin-Lewis-Y tetrasaccharide [50]; Biotin-α-D-mannopyranoside [51]; biotin 6-O-phospho-α-D-mannopyranoside [52]; and polychromium-poly(bis)-[N-(2,6-(diisopropylphenyl) carbamoyl methyl)imino]diacetic acid [53].

TABLE 3

| | | |
|---|---|---|
| 1 | N-hydroxysuccinimide (NHS) biotin<br>2,5-dioxopyrrolidin-1-yl 5-((3aS,6aR)-2-oxohexahydro-1H-thieno[3,4-d]imidazol-4-yl)pentanoate | 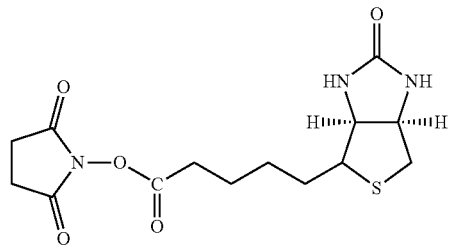 [SMILES: O=C1N[C@H]2CSC(CCCCC(=O)ON3C(=O)CCC3=O)[C@H]2N1] |
| 2 | sulfo-NHS-biotin<br>sodium 2,5-dioxo-3-(trioxidanylthio)pyrrolidin-1-yl 5-((3aS,6aR)-2-oxohexahydro-1H-thieno[3,4-d]imidazol-4-yl)pentanoate | 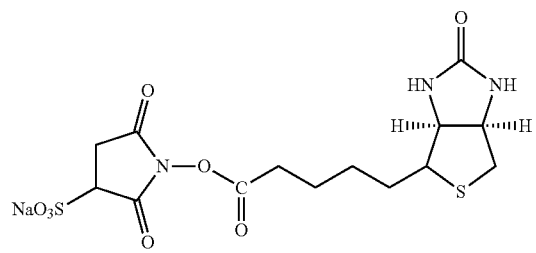 |
| 3 | N-hydroxysuccinimide long chain biotin<br>2,5-dioxopyrrolidin-1-yl 6-(5-((3aS,6aR)-2-oxohexahydro-1H-thieno[3,4-d]imidazol-4-yl)pentanamido)hexanoate | 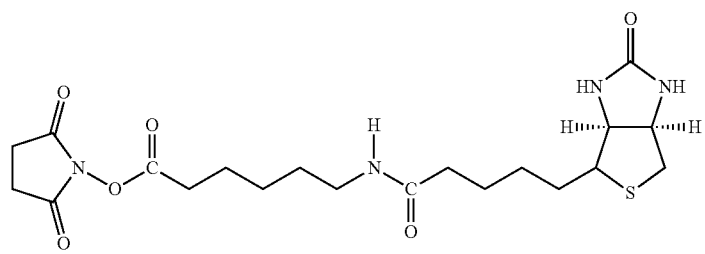 [SMILES: O=C(CCCCC1SC[C@@H]2NC(=O)N[C@H]12)NCCCCCC(=O)ON1C(=O)CCC1=O] |
| 4 | sulfo-N-hydroxysuccinimide long chain biotin<br>sodium 2,5-dioxo-3-(trioxidanylthio)pyrrolidin-1-yl 6-(5-((3aS,6aR)-2-oxohexahydro-1H-thieno[3,4-d]imidazol-4-yl)pentanamido)hexanoate | 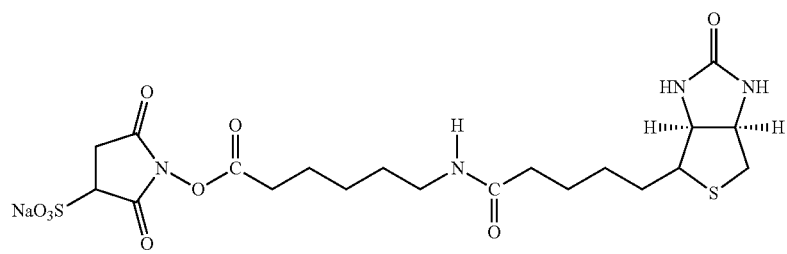 |
| 5 | D-biotin<br>5-((3aS,6aR)-2-oxohexahydro-1H-thieno[3,4-d]imidazol-4-yl)pentanoic acid | 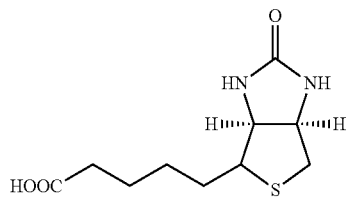 [SMILES: O=C(O)CCCCC1SC[C@@H]2NC(=O)N[C@H]12] |
| 6 | Biocytin<br>2-amino-6-(5-((3aS,6aR)-2-oxohexahydro-1H-thieno[3,4-d]imidazol-4-yl)pentanamido)hexanoic acid | 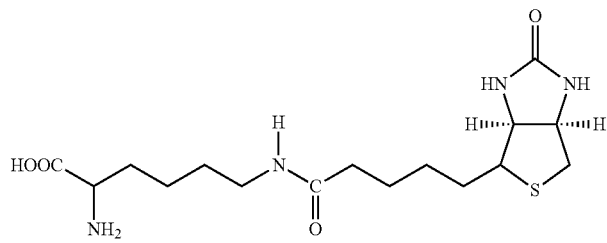 [SMILES: NC(CCCCNC(=O)CCCCC1SC[C@@H]2NC(=O)N[C@H]12)C(=O)O] |

TABLE 3-continued

| | | |
|---|---|---|
| 7 | sulfo-N-hydroxysuccinimide-S-S-biotin<br>sodium 2,5-dioxo-3-(trioxidanylthio)pyrrolidin-1-yl 3-((2-(4-((3aS,6aR)-2-oxohexahydro-1H-thieno[3,4-d]imidazol-4-yl)butylamino)ethyl)disulfanyl)propanoate | 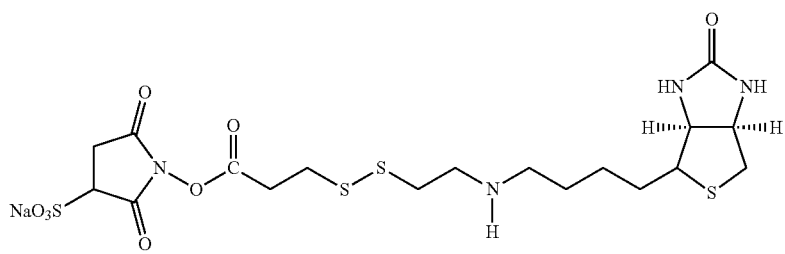 |
| 8 | biotin-BMCC<br>4-((2,5-dioxo-2,5-dihydro-1H-pyrrol-1-yl)methyl)-N-(4-(5-((3aS,6aR)-2-oxohexahydro-1H-thieno[3,4-d]imidazol-4-yl)pentanamido)butyl)cyclohexanecarboxamide | 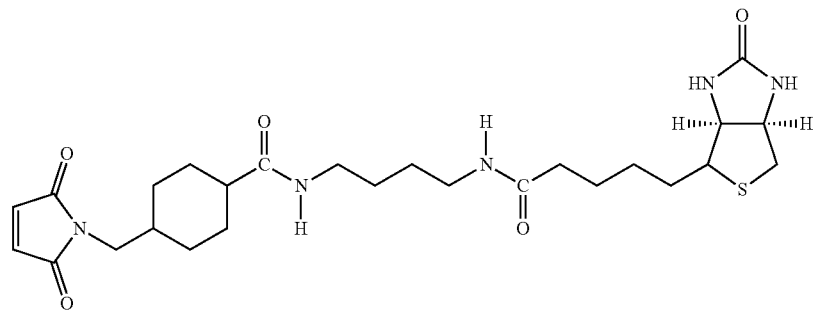 [SMILES: O=C(CCCCC1SC[C@@H]2NC(=O)N[C@H]12)NCCCCNC(=O)C1CCC(CN2C(=O)C=CC2=O)CC1] |
| 9 | biotin-HPDP<br>5-((3aS,6aR)-2-oxohexahydro-1H-thieno[3,4-d]imidazol-4-yl)-N-(6-(3-(pyridin-2-yldisulfanyl)propanamido)hexyl)pentanamide | 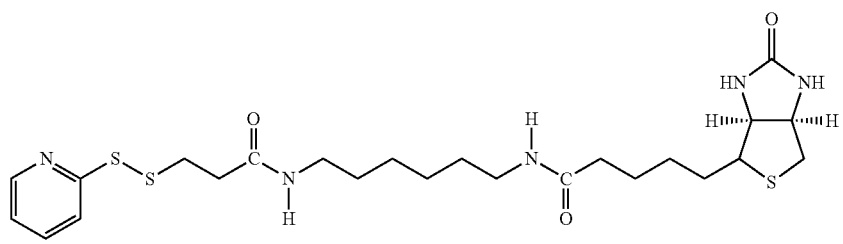 [SMILES: O=C(CCCCC1SC[C@@H]2NC(=O)N[C@H]12)NCCCCCCNC(=O)CCSSc1ccccn1] |
| 10 | iodoacetyl-LC-biotin<br>N-(6-(2-iodoacetamido)hexyl)-5-((3aS,6aR)-2-oxohexahydro-1H-thieno[3,4-d]imidazol-4-yl)pentanamide | 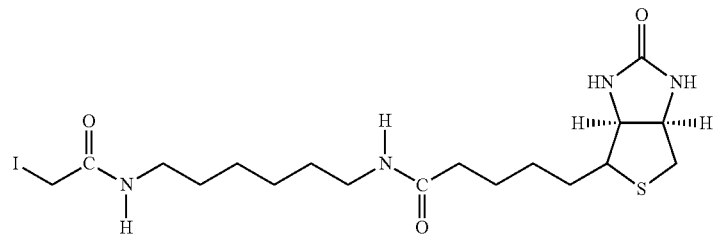 [SMILES: O=C(CI)NCCCCCCNC(=O)CCCCC1SC[C@@H]2NC(=O)N[C@H]12] |
| 11 | biotin-hydrazide<br>5-((3aS,6aR)-2-oxohexahydro-1H-thieno[3,4-d]imidazol-4-yl)pentanehydrazide | 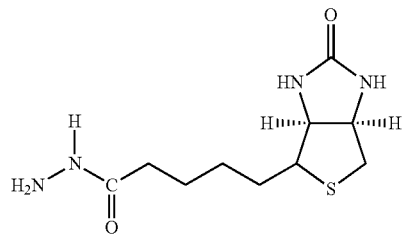 [SMILES: NNC(=O)CCCCC1SC[C@@H]2NC(=O)N[C@H]12] |
| 12 | biotin-LC-hydrazide<br>N-(6-hydrazinyl-6-oxohexyl)-5-((3aS,6aR)-2-oxohexahydro-1H-thieno[3,4-d]imidazol-4-yl)pentanamide | 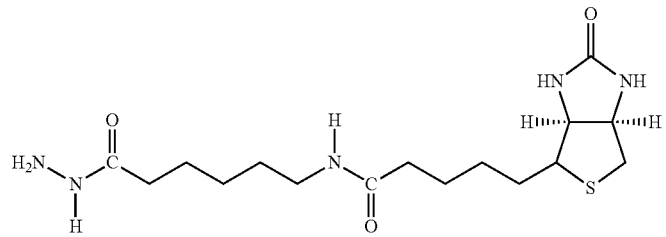 [SMILES: NNC(=O)CCCCCNC(=O)CCCCC1SC[C@@H]2NC(=O)N[C@H]12] |

TABLE 3-continued

| 13 | biocytin hydrazide<br>N-(5-amino-6-hydrazinyl-6-oxohexyl)-5-((3aS,6aR)-2-oxohexahydro-1H-thieno[3,4-d]imidazol-4-yl)pentanamide | 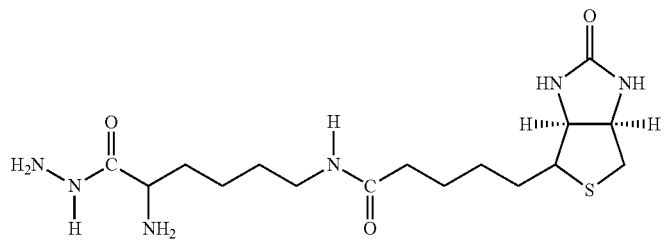 [SMILES: NNC(=O)C(N)CCCCNC(=O)CCCCC1SC[C@@H]2NC(=O)N[C@H]12] |
|---|---|---|
| 14 | biotin cadaverine<br>N-(5-aminopentyl)-5-((3aS,6aR)-2-oxohexahydro-1H-thieno[3,4-d]imidazol-4-yl)pentanamide | 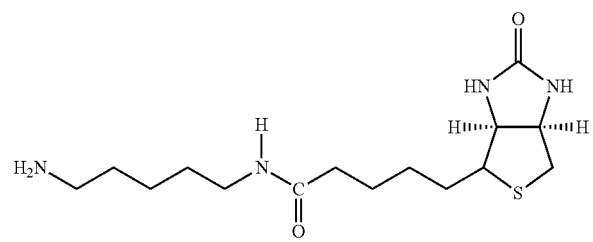 [SMILES: NCCCCCNC(=O)CCCCC1SC[C@@H]2NC(=O)N[C@H]12] |
| 15 | Carboxybiotin<br>(3aS,6aR)-4-(4-carboxybutyl)-2-oxohexahydro-1H-thieno[3,4-d]imidazole-1-carboxylic acid | 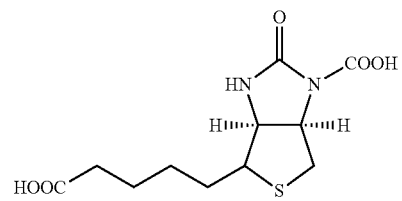 [SMILES: O=C(O)CCCCC1SC[C@H]2[C@@H]1NC(=O)N2C(=O)O] |
| 16 | Photobiotin<br>N-(3-((3-(4-azido-2-nitrophenylamino)propyl)(methyl)amino)propyl)-5-((3aS,6aR)-2-oxohexahydro-1H-thieno[3,4-d]imidazol-4-yl)pentanamide | 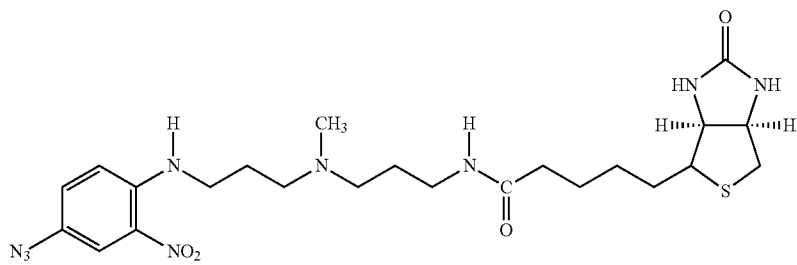 [SMILES: CN(CCCNC(=O)CCCCC1SC[C@@H]2NC(=O)N[C@H]12)CCCNc1ccc(N=[N+]=[N-])cc1[N+](=O)[O-]] |
| 17 | ρ-aminobenzoyl biocytin trifluoroacetate<br>2-(4-aminobenzamido)-6-(5-((3aS,6aR)-2-oxohexahydro-1H-thieno[3,4-d]imidazol-4-yl)pentanamido)hexanoic acid 2,2,2-trifluoroacetate | 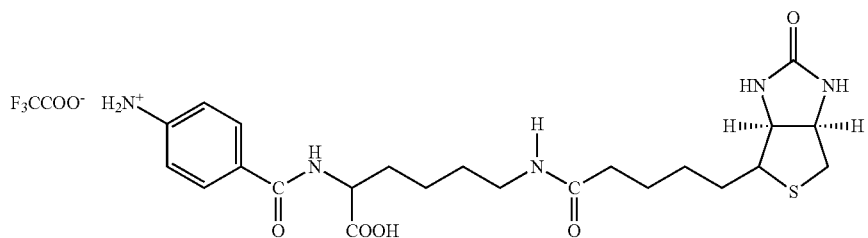 [SMILES: "F3CCOO-" ; [NH3+]c1ccc(C(=O)NC(CCCCNC(=O)CCCCC2SC[C@@H]3NC(=O)N[C@H]23)C(=O)O)cc1] |
| 18 | ρ-diazobenzoyl biocytin<br>4-(1-carboxy-5-(5-((3aS,6aR)-2-oxohexahydro-1H-thieno[3,4-d]imidazol-4-yl)pentanamido)pentylcarbamoyl)benzenediazonium chloride | 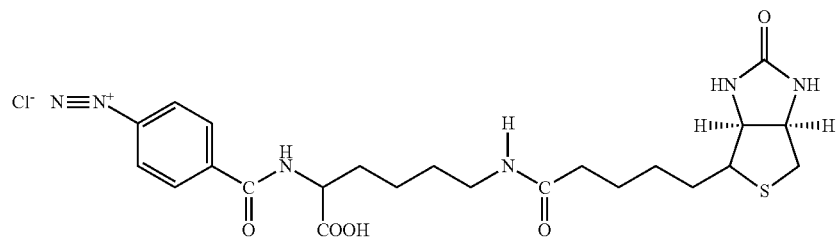 [SMILES: [Cl-] ; N#[N+]c1ccc(C(=O)NC(CCCCNC(=O)CCCCC2SC[C@@H]3NC(=O)N[C@H]23)C(=O)O)cc1] |

TABLE 3-continued

| | | |
|---|---|---|
| 19 | biotin DHPE triethylammonium 2,3-diacetoxypropyl 2-(5-((3aS,6aR)-2-oxohexahydro-1H-thieno[3,4-d]imidazol-4-yl)pentanamido)ethyl phosphate | |
| 20 | biotin-X-DHPE triethylammonium 2,3-diacetoxypropyl 2-(6-(5-((3aS,6aR)-2-oxohexahydro-1H-thieno[3,4-d]imidazol-4-yl)pentanamido)hexanamido)ethyl phosphate | |
| 21 | 12-((biotinyl)amino)dodecanoic acid 12-(5-((3aS,6aR)-2-oxohexahydro-1H-thieno[3,4-d]imidazol-4-yl)pentanamido) dodecanoic acid | |
| 22 | 12-((biotinyl)amino)dodecanoic acid succinimidyl ester 2,5-dioxopyrrolidin-1-yl 12-(5-((3aS,6aR)-2-oxohexahydro-1H-thieno[3,4-d]imidazol-4-yl)pentanamido)dodecanoate | |
| 23 | S-biotinyl homocysteine 4-mercapto-2-(5-((3aS,6aR)-2-oxohexahydro-1H-thieno[3,4-d]imidazol-4-yl)pentanamido)butanoic acid | |
| 24 | biocytin-X 2-amino-6-(6-(5-((3aS,6aR)-2-oxohexahydro-1H-thieno[3,4-d]imidazol-4-yl)pentanamido)hexanamido)hexanoic acid | |

TABLE 3-continued

| 25 | biocytin x-hydrazide<br>N-(5-amino-6-hydrazinyl-6-oxohexyl)-6-(5-((3aS,6aR)-2-oxohexahydro-1H-thieno[3,4-d]imidazol-4-yl)pentanamido)hexanamide | 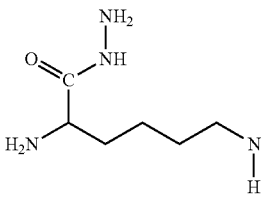 |
|---|---|---|
| 26 | Biotinethylenediamine<br>N-(2-aminoethyl)-5-((3aS,6aR)-2-oxohexahydro-1H-thieno[3,4-d]imidazol-4-yl)pentanamide | 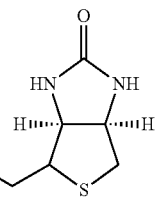 |
| 27 | biotin-X<br>6-(5-((3aS,6aR)-2-oxohexahydro-1H-thieno[3,4-d]imidazol-4-yl)pentanamido)hexanoic acid | 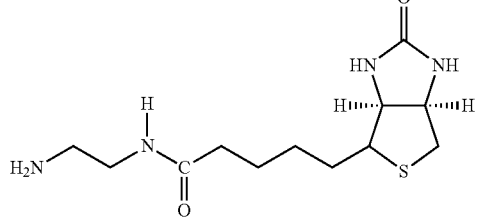 |
| 28 | biotin-X-ethylenediamine<br>N-(2-aminoethyl)-6-(5-((3aS,6aR)-2-oxohexahydro-1H-thieno[3,4-d]imidazol-4-yl)pentanamido)hexanamide | 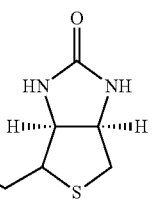 |
| 29 | biotin-XX hydrazide<br>N-(6-hydrazinyl-6-oxohexyl)-6-(5-((3aS,6aR)-2-oxohexahydro-1H-thieno[3,4-d]imidazol-4-yl)pentanamido)hexanamide | 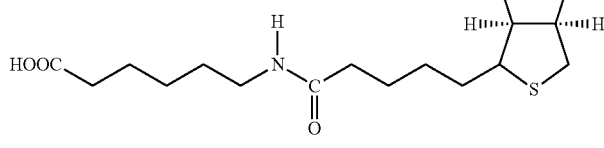 |
| 30 | biotin-XX-SE<br>2,5-dioxopyrrolidin-1-yl 6-(6-(5-((3aS,6aR)-2-oxohexahydro-1H-thieno[3,4-d]imidazol-4-yl)pentanamido)hexanamido)hexanoate | 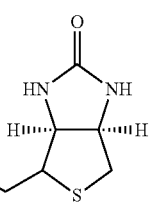 |
| 31 | biotin-XX.SSE<br>sodium 2,5-dioxo-1-(6-(6-(5-((3aS,6aR)-2-oxohexahydro-1H-thieno[3,4-d]imidazol-4-yl)pentanamido)hexanamido)hexanoyloxy)pyrrolidine-3-sulfonate | 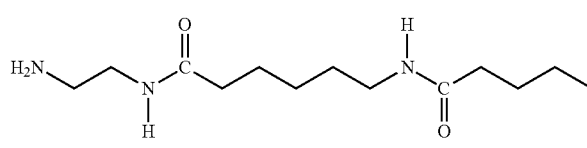 |

TABLE 3-continued

| 32 | biotin-X-cadaverine<br>5-(6-(5-((3aS,6aR)-2-oxohexahydro-1H-thieno[3,4-d]imidazol-4-yl)pentanamido)hexanamido)pentan-1-aminium 2,2,2-trifluoroacetate | 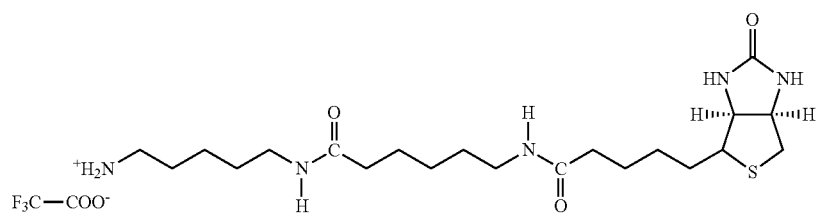 |
| --- | --- | --- |
| 33 | α-(t-BOC)biocytin<br>2-(tert-butoxycarbonylamino)-6-(5-((3aS,6aR)-2-oxohexahydro-1H-thieno[3,4-d]imidazol-4-yl)pentanamido)hexanoic acid | 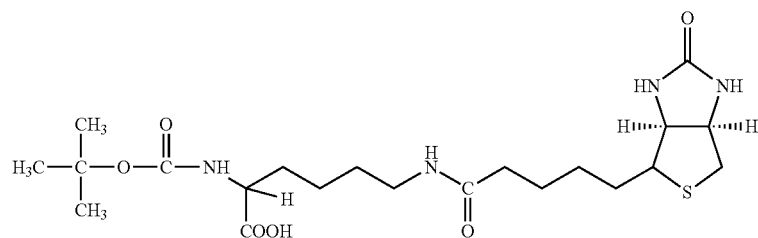 [SMILES: CC(C)(C)OC(=O)NC(CCCCNC(=O)CCCCC1SC[C@@H]2NC(=O)N[C@H]12)C(=O)O] |
| 34 | N-(biotinyl)-N'-(iodoacetyl)ethylenediamine<br>N-(2-(2-iodoacetamido)ethyl)-5-((3aS,6aR)-2-oxohexahydro-1H-thieno[3,4-d]imidazol-4-yl)pentanamide | 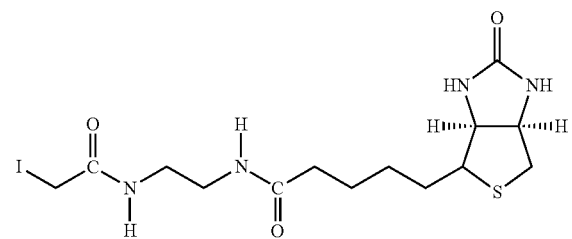 [SMILES: O=C(CI)NCCNC(=O)CCCCC1SC[C@@H]2NC(=O)N[C@H]12] |
| 35 | DNP-X-biocytin-X-SE<br>2,5-dioxopyrrolidin-1-yl 2-(6-(6-(2,4-dinitrophenylamino)hexanamido)hexanamido)-6-(6-(5-((3aS,6aR)-2-oxohexahydro-1H-thieno[3,4-d]imidazol-4-yl)pentanamido)hexanamido)hexanoate | 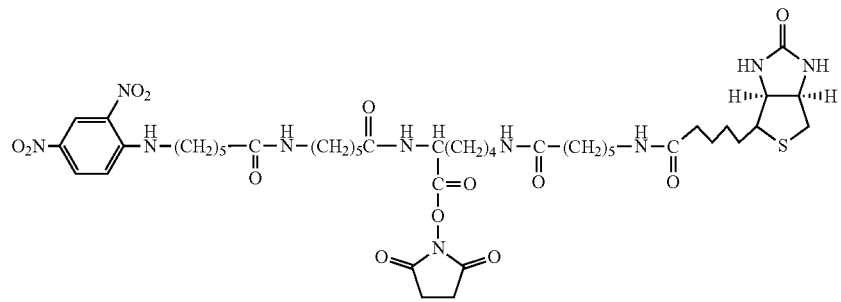 |
| 36 | biotin-X-hydrazide<br>N-(6-hydrazinyl-6-oxohexyl)-5-((3aS,6aR)-2-oxohexahydro-1H-thieno[3,4-d]imidazol-4-yl)pentanamide | 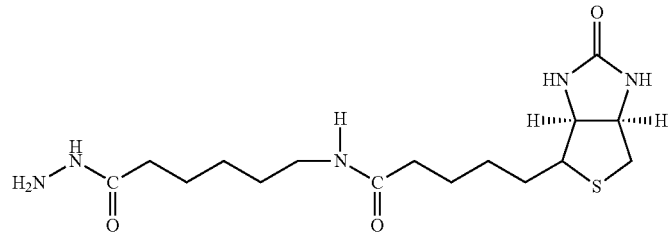 [SMILES: NNC(=O)CCCCCNC(=O)CCCCC1SC[C@@H]2NC(=O)N[C@H]12] |
| 37 | norbiotinamine hydrochloride<br>4-((3aS,6aR)-2-oxohexahydro-1H-thieno[3,4-d]imidazol-4-yl)butan-1-aminium chloride | 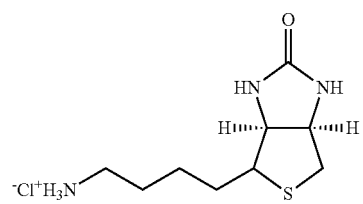 |

TABLE 3-continued

| | | |
|---|---|---|
| 38 | 3-(N-maleimidylpropionyl) biocytin<br>2-(3-(2,5-dioxo-2,5-dihydro-1H-pyrrol-1-yl)propanamido)-6-(5-((3aS,6aR)-2-oxohexahydro-1H-thieno[3,4-d]imidazol-4-yl)pentanamido)hexanoic acid | 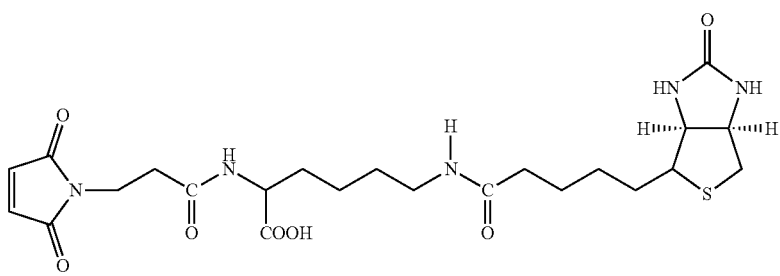 [SMILES: O=C(CCCCC1SC[C@@H]2NC(=O)N[C@H]12)NCCCCC(NC(=O)CCN1C(=O)C=CC1=O)C(=O)O] |
| 39 | ARP;<br>N'-(2-(aminooxy)acetyl)-5-((3aS,6aR)-2-oxohexahydro-1H-thieno[3,4-d]imidazol-4-yl)pentanehydrazide | 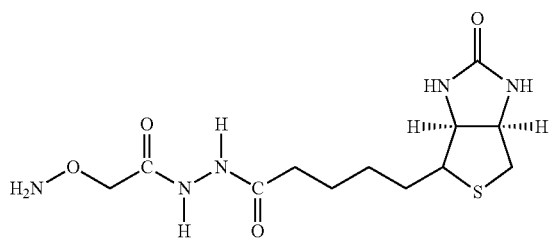 [SMILES: NOCC(=O)NNC(=O)CCCCC1SC[C@@H]2NC(=O)N[C@H]12] |
| 40 | biotin-1-sulfoxide<br>5-((3aS,6aR)-2-oxohexahydro-1H-thieno[3,4-d]imidazol-4-yl)pentanoic acid sulfoxide | 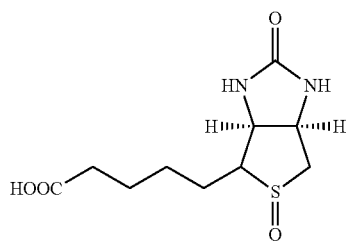 [SMILES: O=C(O)CCCCC1[C@H]2NC(=O)N[C@H]2CS1=O] |
| 41 | biotin methyl ester<br>methyl 5-((3aS,6aR)-2-oxohexahydro-1H-thieno[3,4-d]imidazol-4-yl)pentanoate | 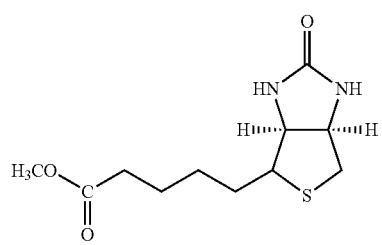 [SMILES: COC(=O)CCCCC1SC[C@@H]2NC(=O)N[C@H]12] |
| 42 | biotin-maleimide<br>6-(2,5-dioxo-2,5-dihydro-1H-pyrrol-1-yl)-N'-(5-((3aS,6aR)-2-oxohexahydro-1H-thieno[3,4-d]imidazol-4-yl)pentanoyl)hexanehydrazide | 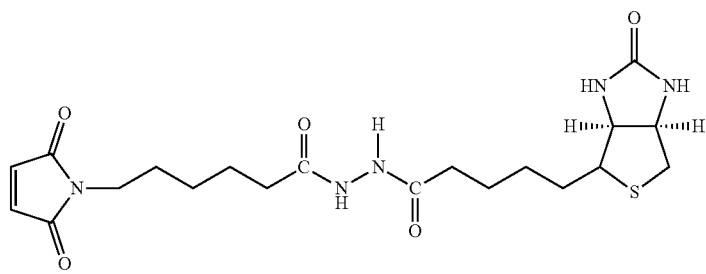 [SMILES: O=C(CCCCCN1C(=O)C=CC1=O)NNC(=O)CCCCC1SC[C@@H]2NC(=O)N[C@H]12] |
| 43 | Biotin-poly(ethyleneglycol) amine<br>aminomethyl polyethylene 5-((3aS,6aR)-2-oxohexahydro-1H-thieno[3,4-d]imidazol-4-yl)pentanoate | 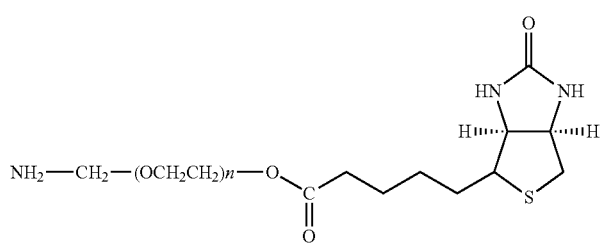 |

TABLE 3-continued

| | | |
|---|---|---|
| 44 | (+) biotin 4-amidobenzoic acid sodium salt<br>sodium 4-(5-((3aS,6aR)-2-oxohexahydro-1H-thieno[3,4-d]imidazol-4-yl)pentanamido)benzoate | 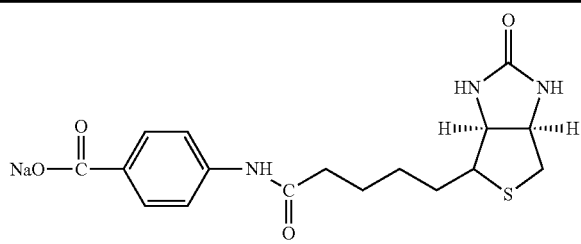 |
| 45 | Biotin 2-N-acetylamino-2-deoxy-β-D-glucopyranoside ((2R,5S)-3-acetamido-4,5-dihydroxy-6-(hydroxymethyl)-2,3,4,5,6-pentamethyltetrahydro-2H-pyran-2-yl)methyl 5-((3aS,6aR)-2-oxohexahydro-1H-thieno[3,4-d]imidazol-4-yl)pentanoate | 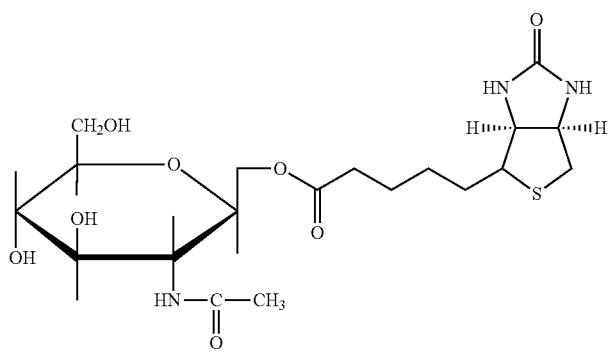 |
| 46 | Biotin-α-D-N-acetylneuraminide (2S,5R)-5-acetamido-4-hydroxy-3,3,4,5,6-pentamethyl-2-((5-((3aS,6aR)-2-oxohexahydro-1H-thieno[3,4-d]imidazol-4-yl)pentanoyloxy)methyl)-6-(1,2,3-trihydroxypropyl)tetrahydro-2H-pyran-2-carboxylic acid | 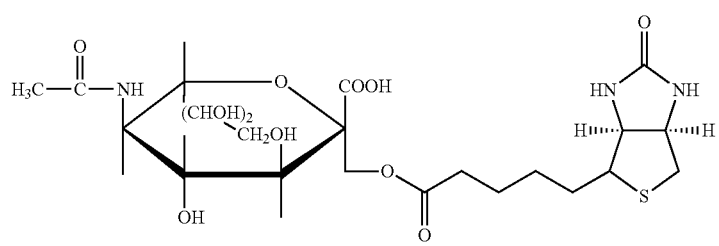 |
| 47 | Biotin-α-L-fucoside ((2R,5S)-3,4,5-trihydroxy-2,3,4,5,6,6-hexamethyltetrahydro-2H-pyran-2-yl)methyl 5-((3aS,6aR)-2-oxohexahydro-1H-thieno[3,4-d]imidazol-4-yl)pentanoate | 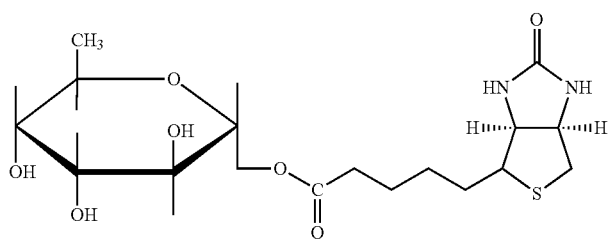 |
| 48 | Biotin lacto-N-bioside<br>See end of table for name | 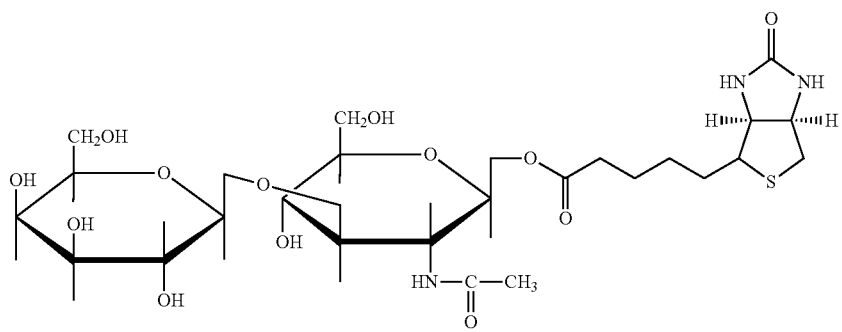 |
| 49 | Biotin-Lewis-A trisaccharide<br>See end of table for name | 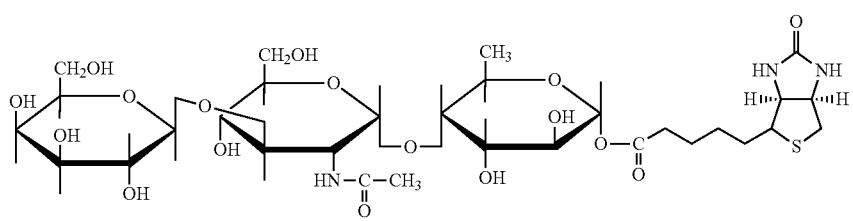 |

TABLE 3-continued

| 50 | Biotin-Lewis-Y tetrasaccharide See end of table for name | 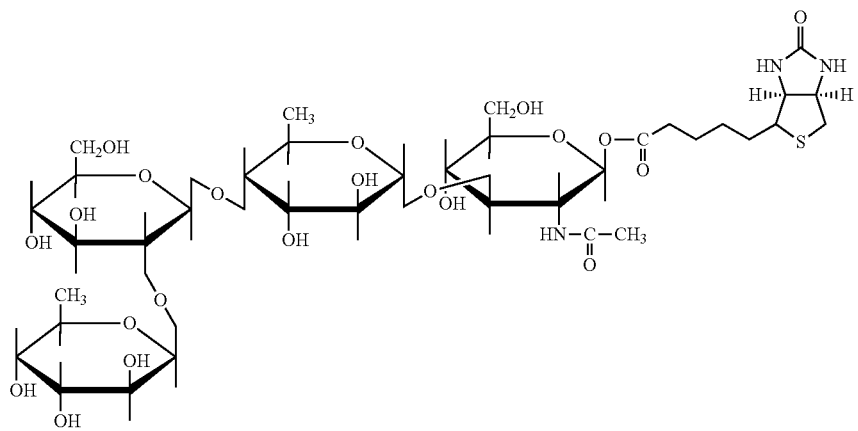 |
| --- | --- | --- |
| 51 | Biotin-α-D-mannopyranoside ((1R,4R)-2,3,4-trihydroxy-5-(hydroxymethyl)-1,2,3,4,5-pentamethylcyclohexyl)methyl 5-((3aS,6aR)-2-oxohexahydro-1H-thieno[3,4-d]imidazol-4-yl)pentanoate | 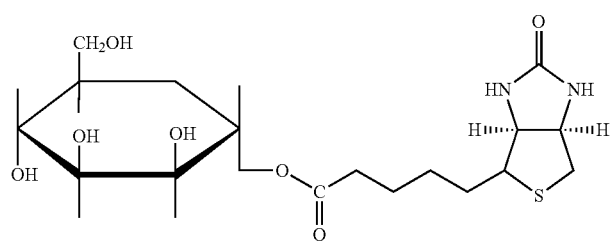 |
| 52 | biotin 6-O-phospho-α-D-mannopyranoside ((2R,5S)-3,4,5-trihydroxy-2,3,4,5,6-pentamethyl-6-(phosphonooxymethyl)tetrahydro-2H-pyran-2-yl)methyl 5-((3aS,6aR)-2-oxohexahydro-1H-thieno[3,4-d]imidazol-4-yl)pentanoate | 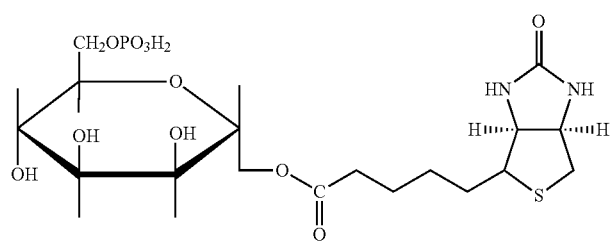 |
| 53 | polychromium-poly(bis)-[N-(2,6-(diisopropylphenyl)carbamoyl methyl)imino diacetic acid] | 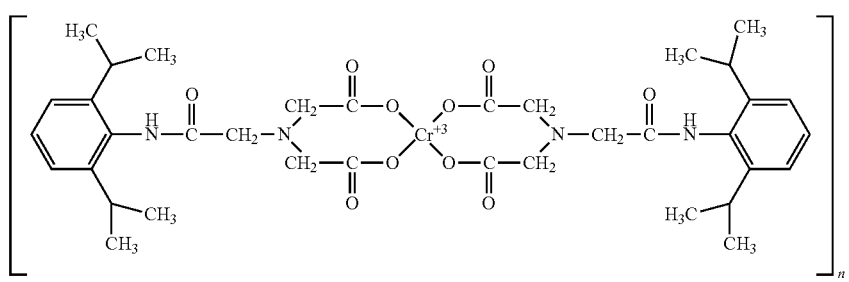 |

Names of Compounds 48-50.
48. ((2R,5S)-3-acetamido-5-hydroxy-6-(hydroxymethyl)-2,3,4,6-tetramethyl-4-(((((2S,5R)-3,4,5-trihydroxy-6-(hydroxymethyl)-2,3,4,5,6-pentamethyltetrahydro-2H-pyran-2-yl)methoxy)methyl) tetrahydro-2H-pyran-2-yl)methyl 5-((3aS,6aR)-2-oxohexahydro-1H-thieno[3,4-d]imidazol-4-yl)pentanoate ((2R,5S)-3-acetamido-5-hydroxy-6-(hydroxymethyl)-2,3,4,6-tetramethyl-4-(((((2S,5R)-3,4,5-trihydroxy-6-(hydroxymethyl)-2,3,4,5,6-pentamethyltetrahydro-2H-pyran-2-yl)methoxy)methyl) tetrahydro-2H-pyran-2-yl)methyl 5-((3aS,6aR)-2-oxohexahydro-1H-thieno[3,4-d]imidazol-4-yl)pentanoate
49. (2R,3R,5S)-5-(((((2S,3S,5S)-3-acetamido-5-hydroxy-6-(hydroxymethyl)-2,4,6-trimethyl-4-(((((2S,5R)-3,4,5-trihydroxy-6-(hydroxymethyl)-2,3,4,5,6-pentamethyltetrahydro-2H-pyran-2-yl)methoxy) methyl)tetrahydro-2H-pyran-2-yl)methoxy)methyl)-3,4-dihydroxy-2,4,5,6,6-pentamethyltetrahydro-2H-pyran-2-yl 5-((3aS,6aR)-2-oxohexahydro-1H-thieno[3,4-d]imidazol-4-yl)pentanoate
50. (2S,5S)-3-acetamido-4-(((((2R,5S)-5-(((((2R,5S)-4,5-dihydroxy-6-(hydroxymethyl)-2,3,4,5,6-pentamethyl-3-(((((2S,5S)-3,4,5-trihydroxy-2,3,4,5,6,6-hexamethyltetrahydro-2H-pyran-2-yl)methoxy)methyl)tetrahydro-2H-pyran-2-yl)methoxy) methyl)-3,4-dihydroxy-2,3,4,5,6,6-hexamethyltetrahydro-2H-pyran-2-yl)methoxy)methyl)-5-hydroxy-6-(hydroxymethyl)-2,3,4,5,6-pentamethyltetrahydro-2H-pyran-2-yl 5-((3aS,6aR)-2-oxohexahydro-1H-thieno[3,4-d]imidazol-4-yl)pentanoate Structure of iminobiotin compounds are not shown in Table 3. The iminobiotin structures are analogs of the biotin structure where the biotin group is replaced by a an iminobiotin group. An example is shown below with the analogs N-hydroxysuccinimide biotin and N-hydroxysuccinimide iminobiotin.

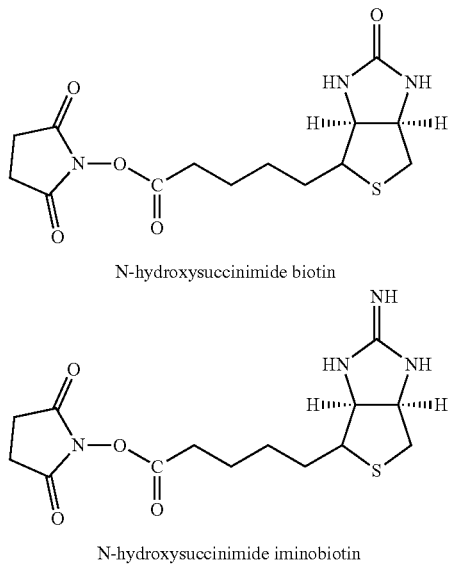

N-hydroxysuccinimide biotin

N-hydroxysuccinimide iminobiotin

Figure 9:
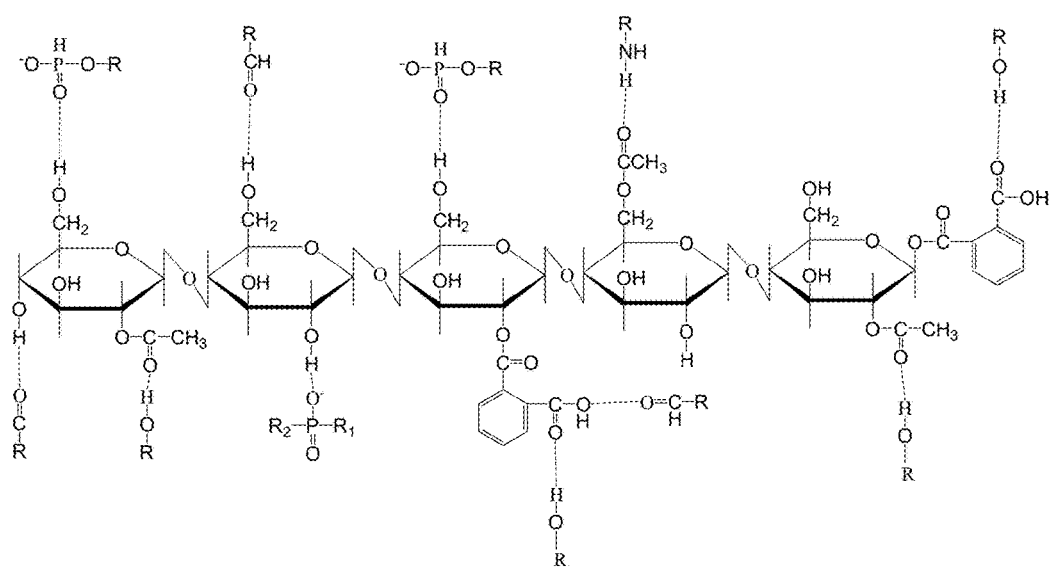
FIG. 9 is a depiction of potential sites for binding between cellulose acetate hydrogen phthalate and insulin.
Figure 10:
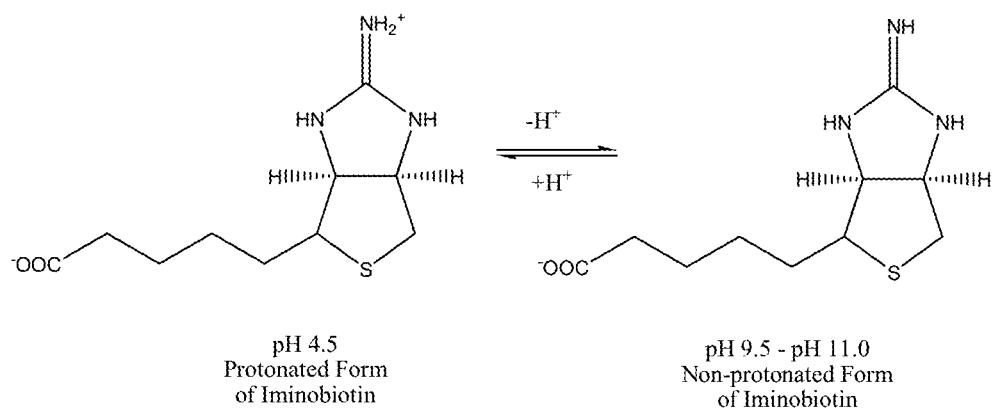
FIG. 10 is a depiction of the change in structure of iminobiotin under acidic versus basic conditions.

In an embodiment, a cellulose acetate hydrogen phthalate polymer is incorporated into the lipid construct where it can bind to hydrophilic functional groups on the insulin molecule and protect insulin from hydrolytic degradation. Cellulose acetate hydrogen phthalate comprises two glucose molecules linked beta (1→4) in a polymeric arrangement in which some of the hydrogen atoms on the hydroxyl groups of the polymer are replaced by an acetyl functionality (a methyl group bound to a carbonyl carbon) or a phthalate group (represented by a benzene ring with two carboxyl groups in the first and second positions of the benzene ring). The structural formula of cellulose acetate hydrogen phthalate polymer is shown in FIG. 9. Only one carboxyl group on the phthalate ring structure is involved in a covalent ester linkage to the cellulose acetate molecule. The other carboxyl group, which contains a carbonyl carbon and a hydroxyl functionality, participates in hydrogen bonding with neighboring negative and positive charged dipoles residing on insulin and various lipid molecules.

In an embodiment, cellulose acetate hydrogen phthalate polymer interacts with the lipids through ion-dipole bonding with 1,2-distearoyl-sn-glycero-3-phosphocholine phosphate and dicetyl phosphate molecules. The ion-dipole bonding occurs between the $\delta^+$ hydrogen on the hydroxyl groups of cellulose and the negatively charged oxygen atom on the phosphate moiety of the phospholipid molecules. The functional groups with the largest role in the ion-dipole interaction are the negatively charged oxygen atoms on the phosphate groups of the phospholipid molecules, hydrogen atoms on the hydroxyl groups and the hydrogen atoms on amide bonds of the insulin molecules. Negatively charged functional groups form sites for ion-dipole interactions and for reacting with the $\delta^+$ hydrogen atom on individual hydroxyl groups and the hydroxyl groups of the carboxyl functionalities on cellulose acetate hydrogen phthalate. Ion-dipoles can be formed between the positively charged quaternary amines on the phosphocholine functionalities and the $\delta^-$ carbonyl oxygen found on cellulose acetate hydrogen phthalate and insulin. Sugar molecules comprising branched hydrophilic structures in insulin can participate in hydrogen bonding and ion-dipole interactions.

The molecular configuration and the size of the polymer (with an approximate molecular weight of 15,000 or more) enables cellulose acetate hydrogen phthalate to coat individual phospholipid molecules of the lipid construct in the region of the hydrophilic head group. This coating protects insulin within the lipid construct from the acid milieu of the stomach. There are several ways that cellulose acetate hydrogen phthalate can be attached to the surface of molecules within the lipid construct. A preferred means of linking cellulose acetate hydrogen phthalate to the surface of the lipid construct is to attach the polymeric cellulosic species to a tail of an insulin molecule that presents a sugar that projects from the surface of the lipid construct. This protects the insulin proteinaceous tails from enzymatic hydrolysis.

An extended amphipathic lipid comprises a variety of multi-dentate binding sites for attachment to the receptor. Multi-dentate binding, as defined herein, requires a plurality of potential binding sites on the surface of insulin and its accompanying sugar moieties, as well as on the lipid construct that can interface with carbonyl, carboxyl and hydroxyl functional groups on the cellulose acetate hydrogen phthalate polymer. This enables the cellulose acetate hydrogen phthalate polymer to bind to a plurality of hydrophilic regions not only on the lipid construct but also on molecules of insulin in order to establish a shield of hydrolytic protection for the lipid construct. In this manner both insulin and the lipid construct are protected from the acid environment of the stomach following oral administration of the insulin dosage form. Even though cellulose acetate hydrogen phthalate covers or shields individual lipid molecules within and on the surface of the lipid construct while passing through the stomach, once the construct migrates to the alkaline region of the small intestine, cellulose acetate hydrogen phthalate is hydrolytically degraded. After cellulose acetate hydrogen phthalate is removed from the surface of the molecules of the lipid construct, a lipid anchoring-hepatocyte receptor binding molecule, such as 1,2-dipalmitoyl-sn-glycero-3-phosphoethanolamine-N-(Cap Biotinyl), becomes exposed and then is available to bind with the receptor. The employment of a cellulose acetate hydrogen phthalate coating on insulin and the lipid construct is needed to ensure that a greater bioavailability of insulin is achieved.

Target Molecule Complex

In an embodiment, the lipid construct comprises a target molecule complex comprising multiple linked individual units formed by complexing a bridging component with a complexing agent. The bridging component is a water soluble salt of a metal capable of forming a water-insoluble coordinated complex with a complexing agent. A suitable metal is selected from the transition and inner transition metals or neighbors of the transition metals. The transition and inner transition metals from which the metal are selected from: Sc (scandium), Y (yttrium), La (lanthanum), Ac (actinium), the actinide series; Ti (titanium), Zr (zirconium), Hf (hafnium), V (vanadium), Nb (niobium), Ta (tantalum), Cr (chromium), Mo (molybdenum), W (tungsten), Mn (manganese), Tc (technetium), Re (rhenium), Fe (iron), Co (cobalt), Ni (nickel), Ru (ruthenium), Rh (rhodium), Pd (palladium), Os (osmium), Ir (iridium), and Pt (platinum). The neighbors of the transition metals from which the metal can be selected are: Cu (copper), Ag (silver), Au (gold), Zn (zinc), Cd (cadmium), Hg (mercury), Al (aluminum), Ga (gallium), In (indium), Tl (thallium), Ge (germanium), Sn (tin), Pb (lead), Sb (antimony) and Bi (bismuth), and Po (polonium). Examples of metal compounds useful as bridging agents include chromium chloride (III) hexahydrate; chromium (III) fluoride tetrahydrate; chromium (III) bromide hexahydrate; zirconium (IV) citrate ammonium complex; zirconium (IV) chloride; zirconium (IV) fluoride hydrate; zirconium (IV) iodide; molybdenum (III) bromide; molybdenum (III) chloride; molybdenum (IV) sulfide; iron (III) hydrate; iron (III) phosphate tetrahydrate, iron (III) sulfate pentahydrate, and the like.

The complexing agent is a compound capable of forming a water insoluble coordinated complex with a bridging component. There are several families of suitable complexing agents.

A complexing agent can be selected from the family of iminodiacetic acids of the formula (1) where $R_1$ is loweralkyl, aryl, arylloweralkyl, and a heterocyclic substituent.

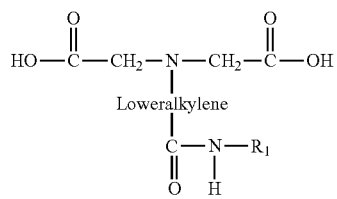
(1)

Suitable compounds of the formula (1) include:
N-(2,6-diisopropylphenylcarbamoylmethyl) iminodiacetic acid;
N-(2,6-diethylphenylcarbamoylmethyl) iminodiacetic acid;
N-(2,6-dimethylphenylcarbamoylmethyl) iminodiacetic acid;
N-(4-isopropylphenylcarbamoylmethyl) iminodiacetic acid;
N-(4-butylphenylcarbamoylmethyl) iminodiacetic acid;
N-(2,3-dimethylphenylcarbamoylmethyl) iminodiacetic acid;
N-(2,4-dimethylphenylcarbamoylmethyl) iminodiacetic acid;
N-(2,5-dimethylphenylcarbamoylmethyl) iminodiacetic acid;
N-(3,4-dimethylphenylcarbamoylmethyl) iminodiacetic acid;
N-(3,5-dimethylphenylcarbamoylmethyl) iminodiacetic acid;
N-(3-butylphenylcarbamoylmethyl) iminodiacetic acid;
N-(2-butylphenylcarbamoylmethyl) iminodiacetic acid;
N-(4-tertiary butylphenylcarbamoylmethyl) iminodiacetic acid;
N-(3-butoxyphenylcarbamoylmethyl) iminodiacetic acid;
N-(2-hexyloxyphenylcarbamoylmethyl) iminodiacetic acid;
N-(4-hexyloxyphenylcarbamoylmethyl) iminodiacetic acid;
aminopyrrol iminodiacetic acid;
N-(3-bromo-2,4,6-trimethylphenylcarbamoylmethyl) iminodiacetic acid;
benzimidazole methyl iminodiacetic acid;
N-(3-cyano-4,5-dimethyl-2-pyrrylcarbamoylmethyl) iminodiacetic acid;
N-(3-cyano-4-methyl-5-benzyl-2-pyrrylcarbamoylmethyl) iminodiacetic acid; and
N-(3-cyano-4-methyl-2-pyrrylcarbamoylmethyl) iminodiacetic acid and other derivatives of N-(3-cyano-4-methyl-2-pyrrylcarbamoylmethyl) iminodiacetic acid of formula (2),

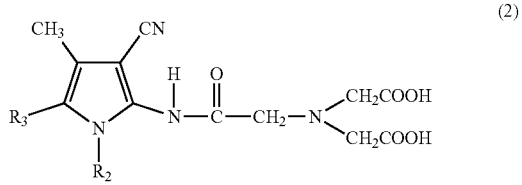
(2)

where $R_2$ and $R_3$ are the following:

| $R_2$ | $R_3$ |
|---|---|
| H | iso-$C_4H_9$ |
| H | $CH_2CH_2SCH_3$ |
| H | $CH_2C_6H_4$-p-OH |
| $CH_3$ | $CH_3$ |
| $CH_3$ | iso-$C_4H_9$ |
| $CH_3$ | $CH_2CH_2SCH_3$ |
| $CH_3$ | $C_6H_5$ |
| $CH_3$ | $CH_2C_6H_5$ |
| $CH_3$ | $CH_2C_6H_4$-p-$OCH_3$ |

A complexing agent is selected from the family of imino diacid derivatives of the general formula (3), where $R_4$, $R_5$, and $R_6$ are independent of each other and can be hydrogen, loweralkyl, aryl, arylloweralkyl, alkoxyloweralkyl, and heterocyclic.

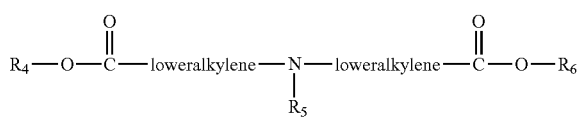
(3)

Suitable compounds of the formula (3) include: N'-(2-acetylnaphthyl) iminodiacetic acid (NAIDA); N'-(2-naphthylmethyl) iminodiacetic acid (NMIDA); iminodicarboxymethyl-2-naphthylketone phthalein complexone; 3 (3: 7a: 12a: trihydroxy-24-norchol anyl-23-iminodiacetic acid; benzimidazole methyl iminodiacetic acid; and N-(5,pregnene-3-p-ol-2-oyl carbamoylmethyl) iminodiacetic acid.

A complexing agent is selected from the family of amino acids of formula (4),

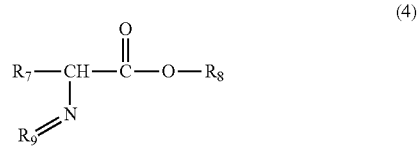
(4)

where $R_7$ is an amino acid side chain, $R_8$ is loweralkyl, aryl, arylloweralkyl, and $R_9$ is pyridoxylidene.

Suitable amino acids of the formula (4) are aliphatic amino acids, including, but not limited to: glycine, alanine, valine, leucine, isoleucine; hydroxyamino acids, including serine, and threonine; dicarboxylic amino acids and their amides, including aspartic acid, asparagine, glutamic acid, glutamine; amino acids having basic functions, including lysine, hydroxylysine, histidine, arginine; aromatic amino acids, including phenylalanine, tyrosine, tryptophan, thyroxine; and sulfur-containing amino acids, including cystine, methionine.

A complexing agent is selected from amino acid derivatives including, but not necessarily limited to (3-alanine-y-amino) butyric acid, O-diazoacetylserine (azaserine), homoserine, ornithine, citrulline, penicillamine and members of the pyridoxylidene class of compounds including, but are not limited to: pyridoxylidene glutamate; pyridoxylidene isoleucine; pyridoxylidene phenylalanine; pyridoxylidene tryptophan; pyridoxylidene-5-methyl tryptophan; pyridoxylidene-5-hydroxytryptamine; and pyridoxylidene-5-butyltryptamine.

A complexing agent is selected from the family of diamines of the general formula (6),

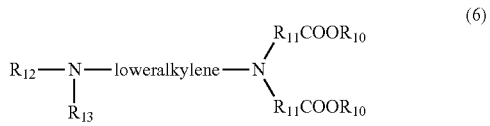

(6)

where $R_{10}$ is hydrogen, loweralkyl, or aryl; $R_{11}$ is loweralkylene or arylloweralky; $R_{12}$ and $R_{13}$ independently are hydrogen, loweralkyl, alkyl, aryl, arylloweralkyl, acylheterocyclic, toluene, sulfonyl or tosylate.

Some suitable diamines of the formula (6) include, but are not limited to, ethylenediamine-N, N diacetic acid; ethylenediamine-N,N-bis (-2-hydroxy-5-bromophenyl) acetate; N'-acetylethylenediamine-N,N diacetic acid; N'-benzoyl ethylenediamine-N,N diacetic acid; N'-(p-toluenesulfonyl) ethylenediamine-N, N diacetic acid; N'-(p-t-butylbenzoyl) ethylenediamine-N, N diacetic acid; N'-(benzenesulfonyl) ethylenediamine-N, N diacetic acid; N'-(p-chlorobenzenesulfonyl) ethylenediamine-N, N diacetic acid; N'-(p-ethylbenzenesulfonyl ethylenediamine-N,N diacetic acid; N'-acyl and N'-sulfonyl ethylenediamine-N, N diacetic acid; N'-(p-n-propylbenzenesulfonyl) ethylenediamine-N, N diacetic acid; N'-(naphthalene-2-sulfonyl) ethylenediamine-N, N diacetic acid; and N'-(2, 5-dimethylbenzenesulfonyl) ethylenediamine-N, N diacetic acid.

Other suitable complexing compounds or agents include, but are not limited to: penicillamine; p-mercaptoisobutyric acid; dihydrothioctic acid; 6-mercaptopurine; kethoxal-bis (thiosemicarbazone); Hepatobiliary Amine Complexes, 1-hydrazinophthalazine (hydralazine); sulfonyl urea; Hepatobiliary Amino Acid Schiff Base Complexes; pyridoxylidene glutamate; pyridoxylidene isoleucine; pyridoxylidene phenylalanine; pyridoxylidene tryptophan; pyridoxylidene 5-methyl tryptophan; pyridoxylidene-5-hydroxytryptamine; pyridoxylidene-5-butyltryptamine; tetracycline; 7-carboxy-p-hydroxyquinoline; phenolphthalein; eosin I bluish; eosin I yellowish; verograffin; 3-hydroxyl-4-formyl-pyridene glutamic acid; Azo substituted iminodiacetic acid; hepatobiliary dye complexes, such as rose bengal; congo red; bromosulfophthalein; bromophenol blue; toluidine blue; and indocyanine green; hepatobiliary contrast agents, such as iodipamide; and ioglycamic acid; bile salts, such as bilirubin; cholgycyliodohistamine; and thyroxine; hepatobiliary thio complexes, such as penicillamine; p-mercaptoisobutyric acid; dihydrothiocytic acid; 6-mercaptopurine; and kethoxal-bis (thiosemicarbazone); hepatobiliary amine complexes, such as 1-hydrazinophthalazine (hydralazine); and sulfonyl urea; hepatobiliary amino acid Schiff Base complexes, including pyridoxylidene-5-hydroxytryptamine; and pyridoxylidene-5-butyltryptamine; hepatobiliary protein complexes, such as protamine; ferritin; and asialo-orosomucoid; and asialo complexes, such as lactosaminated albumin; immunoglobulins, G, IgG; and hemoglobin.

The three-dimensional target molecule complex made from combining bridging agents and complexing agents is described in WO 99/59545, which is incorporated herein by reference. In an embodiment, the bridging agent is a metal salt, such as chromium chloride hexahydrate, capable of forming a coordinated complex with complexing agents, such as N-(2,6-diisopropylphenylcarbamoylmethyl) iminodiacetic acid. The bridging agent and the complexing agents are combined to form a complex composed of multiple linked units in a three-dimensional array. In a preferred embodiment, the complex is composed of multiple units of chromium (bis) [N-(2,6-(diisopropylphenyl)carbamoyl methyl)imino diacetic acid] linked together. In an embodiment, the chromium target molecule complex substance is soluble in a mixture of lipids containing 1,2-distearoyl-sn-glycero-3-phosphocholine, dicetyl phosphate and cholesterol. The complex is incorporated within a lipid construct formed from the groups of lipids previously described.

Modification of the Isoelectric Point of Insulin

The isoelectric point of a protein can affect the release and distribution of the protein in the body of a patient treated with the protein. By changing the isoelectric point of a protein, the rate of release of the protein from the site of administration may be altered and the pharmacokinetics of the protein can be changed.

One method of altering the isolectric point of insulin is to alter its molecular structure by substituting or adding various amino acids. Two examples of altering the structure of insulin to obtain different properties are glargine insulin and insulin aspart. Both of these insulins differ in amino acid composition from recombinant human regular insulin. Recombinant human regular insulin has an isoelectric point at 5.30-5.35. Glargine insulin substitutes glycine for asparagine at position A21 and two arginines are added at the C-terminus of the B chain. The isoelectric points of glycine and asparagine are 5.97 and 5.41, respectively. The substitution of glycine for asparagine has little or no effect on the isoelectric point of glargine insulin. However, the addition of two highly basic arginine amino acid residues, with isoelectric points of 10.76, significantly raises the isoelectric point of glargine insulin to pH 5.8-6.2.

Insulin aspart substitutes aspartic acid for praline at position B-28. The isoelectric points of aspartic acid and praline are 2.97 and 6.10, respectively. With this single acidic amino acid substitution, the isoelectric point of insulin aspart is shifted significantly toward a lower, more acidic, pH.

These two examples of commercially available insulins illustrate how a relatively small number of amino acid substitutions can significantly either raise or lower the isoelectric points of insulin glargine or insulin aspart with respect to recombinant human regular insulin. By altering the chemical properties of insulin, the bioavailability and pharmacodynamic profiles are also changed. When an insulin with a modified structure is administered to a diabetic patient in order to improve bioavailability, the new pharmacological responses provide new therapeutic benefits.

The isoelectric point of insulins can be modified not only by internal molecular restructuring of the primary amino acid sequences of insulin, but also by binding charged organic molecules to insulin. The charged organic molecules can be bound to the surface, or within the insulin structure. The isoelectric point of native insulin can be changed from pH 5.3 to pH 7.2 by adding between 1.0 and 1.5 mg of a mixture of highly basic proteins to 1.0 ml of an insulin solution containing 100 units or 3.65 mg of insulin/ml. Protamines are an example of a group of simple, highly basic proteins that can be can used to alter the isoelectric point of insulin. Protamines yield numerous basic amino acids on hydrolysis, possess a high nitrogen content and occur naturally, combined with nucleic acid, in the sperm of fish. For example, the protamines salmine, clupeine, iridine, sturine and scombrine are isolated from salmon, herring, trout, sturgeon and mackerel sperm, respectively. These basic proteins, either individually or as a mixture, associate with insulin and increase the isoelectric point of insulin.

Compounds that alter the surface charge of insulin include derivatives of polylysine and other highly basic amino acid polymers, such as polyornithine, polyhydroxylysine, polyarginine and polyhistidine or combinations thereof. Other polymers include poly (arg-pro-thr)$_n$ in a mole ratio of 1:1:1 with a molecular weight range of a few hundred to several thousand or poly (DL-Ala-poly-L-lys)$_n$ in a mole ratio of 6:1 with a molecular weight range of a few hundred to several thousand. Histones, basic proteins that exist in several subtypes that contain different and varying amounts of arginine, lysine and other basic amino acids that can bind ionically to carboxyl groups of insulin, and fragments of histones, are also used to provide a positive charge. Also included are polymers such as polyglucosamine, polygalactosamine and various other sugar polymers that contain a positive charge contributed by a primary amino group. Polynucleotides such as polyadenine, polycytosine or polyguanine that provide a positive charge through the ionization of their primary amino group are also used. All the above polymeric species when bound to insulin provide an increase in positive charge that is accompanied by an increase in the isoelectric point of insulin. Small amounts of these polymeric compounds, such as a few micrograms of polymer/ml of insulin, areadded to change the isoelectric point of insulin a minimal amount, generally less that one pH unit. Larger amounts, generally greater than a milligram or two, of basic organic compounds can be added per ml of insulin at 100 units/ml to progressively increase the isoelectric point of insulin to more than two pH units beyond its native isoelectric point.

Conversely, the isoelectric point of insulin can be lowered in a similar fashion by adding carboxylated polymers and polymeric amino acids such as polyaspartic acid, polyglutamic acid, proteins or fragments of proteins that contain large amounts of amino acid residues with carboxyl ($COO^-$) or sulfhydral ($S^-$) functional groups. Highly basic proteins can be changed to highly acidic proteins by reacting them with an appropriate anhydride, such as acetic anhydride, to form a negatively charged terminal acidic carboxyl group in place of a positively charged basic primary amino group. Other acidic polymers, such as sulfate-laden polymers, may be added to insulin to lower the isoelectric point of insulin. Sugar polymers such as polygalacturonic acid, polygluconic acid, polyglucuronic acid or polyglucaric acid that contain negatively charged carboxyl groups can be used to lower the isoelectric point of the protein.

Changing the isoelectric point of an insulin alters not only the ionic character of the native insulin molecule, but also the nature of the ionic envelope, known as the Hemholtz double layer, that surrounds insulin and extends into the bulk phase aqueous media around the insulin. The ionic environment surrounding insulin tends to exist in layers with a layer of counter-ions associated with the participating charged organic molecules that are bound to insulin. An electric potential exists on modified insulin molecules that are maintained in a colloidal suspension in bulk phase media because of the presence of ions on the surface of insulin. That part of the electric potential existing between the layer of fixed counter ions associated with the bound organic molecules and that of the bulk phase media is know as the electrokinetic or zeta ($\xi$) potential. The zeta potential contributes significantly to the electrical properties and stability of colloidal systems such as insulin in aqueous media.

As a result of forming a different chemical structure by the addition of material to change the isoelectric point, the stability of the protein insulin in colloidal suspension is inherently altered. Insulin experiences a shift in stability at the newly modified isoelectric point due to a lower zeta potential. Insulin is least stable when it is in the zwitterionic, or hybrid form, where the negatively charged functional groups precisely balance the positively charged functional groups and create an overall net zero charge on the protein. Even though the overall net charge is zero, there remain pockets of negative charge and pockets of positive charge throughout the protein structure. As the pH of a solution of insulin reaches its isoelectric point, its solubility decreases and insulin may precipitate from solution. During the isoelectric precipitation of insulin, the insulating and dielectric properties of the bulk phase aqueous buffer media are overcome and the ion atmosphere of the Hemholtz double layer is fractured so that dissimilar charges between colloidal particles can associate which leads to a protein colloidal suspension with increasing instability. These effects eventually result in the coagulation and subsequent precipitation of the protein at the isoelectric point. The ideal range for isoelectric precipitation is two or three pH units above or below the isoelectric point of insulin at pH 5.3. However, isoelectric points extending beyond this pH range may be formulated through the use of information by one skilled in the art.

As the pH changes from the isoelectric point, solubility increase and insulin that precipitated at the isoelectric point can be resolubilized. This occurs because as the pH is increased or decreased from the isoelectric point, there is a respective accumulation of negative charge (above the isoelectric point) or an accumulation of positive charge (below the isoelectric point) that is regulated by the pKa of the representative functional groups. Resolubilization occurs as the protein develops a greater disparity of charge thereby increasing the zeta potential of the protein which in turn improves protein stability. These effects result in the redevelopment of an ionic envelope which surrounds the protein which facilitates greater colloidal dispersion of the insulin molecules.

The isoelectric point of native insulin, which occurs at pH 5.3, can be progressively raised by adding proteins, peptide fragments, polymers or polymer fragments that bind to insulin and alter the ionic character of insulin. The overall affect of adding basic functional groups is to raise the isoelectric point of insulin and create an insulin that has a slower onset of pharmacological action by having the insulin transition between a soluble from, to an insoluble form, and then to a new soluble form. By modifying the isoelectric point of native insulin, especially in the presence of HDV insulin, the bioavailability of both insulin forms can be regulated.

Insulins in which the isoelectric point was altered by changing the amino acid sequence can be incorporated into a lipid construct. In an embodiment, glargine insulin is incorporated into a target molecule complex comprising a lipid and multiple linked individual units formed by complexing a bridging component with a complexing agent. A description of the target molecule complex and its components was previously described herein. The structure of glargine insulin is provided in FIG. 11. Glargine insulin differs from human insulin in that glargine insulin has a molecular structure that replaces asparagine with glycine at the C-terminal end of the A chain of human insulin and adds the dipeptide of arginine at the C-terminal end of the B chain of human insulin. The isoelectric point of a compound is the pH at which the overall charge of the compound is neutral. However, regions of negative and positive charges still remain within the compound. The isoelectric point of human insulin is at pH 5.3. The isoelectric point of glargine insulin is higher than human insulin because the amino acid substitutions in glargine insulin raise the isoelectric point of glargine insulin to pH 5.8-6.2. Compounds are generally less soluble in aqueous solutions at pH ranges around the isoelectric point. A compound is generally more soluble in aqueous systems where the pH of the solution is approximately 1-2 pH units higher or lower than the isoelectric point. The higher isoelectric point allows glargine insulin to remain soluble in a mildly acidic environment over a broader pH range.

A commercial form of glargine insulin, LANTUS® (insulin glargine [rDNA origin] injection), is a sterile solution of glargine insulin for use as an injectable insulin for diabetic patients for subsequent management of glucose levels in vivo. Glargine insulin is a recombinant human insulin analog that is a long-acting (up to 24-hour duration of action), parenteral blood-glucose-lowering agent. LANTUS® is produced by recombinant DNA technology utilizing a non-pathogenic laboratory strain of *Escherichia coli* (K12) as the production organism. LANTUS consists of glargine insulin dissolved in a clear aqueous fluid. Each milliliter of LANTUS (insulin glargine injection) contains 100 IU (3.6378 mg) glargine insulin, 30 mcg zinc, 2.7 mg m-cresol, 20 mg glycerol 85%, and water for injection. The pH of commercially available LANTUS insulin can be adjusted by addition of aqueous solutions of acids, bases or buffers that are physiologically compatible. LANTUS has a pH of approximately 4.

Figure 13:
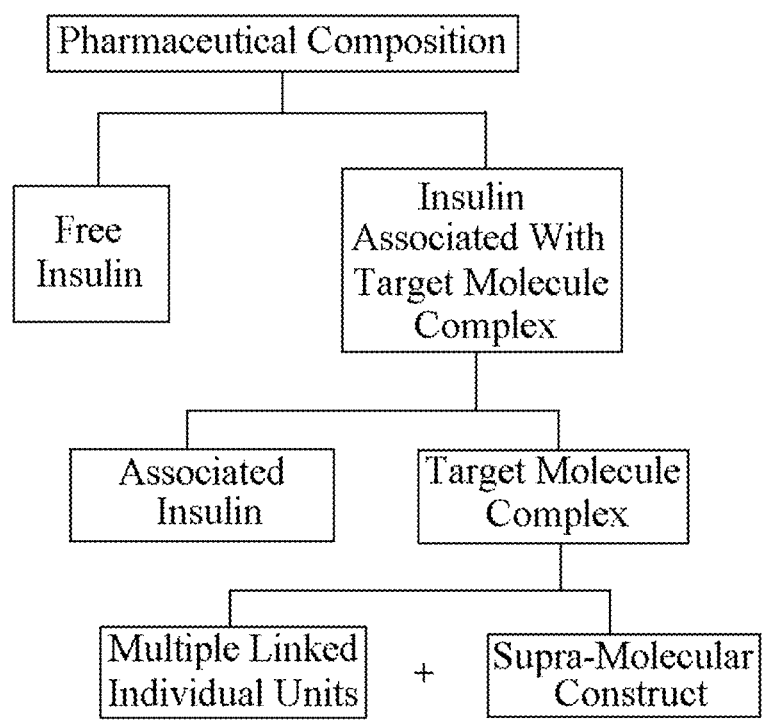
FIG. 13 is a depiction of a pharmaceutical composition that combines free insulin and insulin associated with a water insoluble target molecule complex.

A depiction of a pharmaceutical composition that combines free insulin and insulin associated with a target molecule complex is shown in FIG. 13. In an embodiment, a pharmaceutical composition may comprise two or more insulins. The target molecule complex comprises multiple linked individual units formed by complexing a bridging component with a complexing agent. The bridging component is a water soluble salt of a metal capable of forming a water-insoluble coordinated complex with a complexing agent. A suitable metal is selected from the transition and inner transition metals or neighbors of the transition metals. A description of the target molecule complex and its components was previously described herein. In an embodiment, a pharmaceutical composition comprises a mixture of free insulin and insulin associated with a water insoluble target molecule complex. Free insulin is not associated with the target molecule complex and is soluble in water. The other form of insulin in the composition is associated with a water insoluble target molecule complex.

Adjustment of the pH of an aqueous solution surrounding the lipid construct containing the target molecule complex, by the addition of acids, bases, or buffers, results in a negative charge in the lipid construct structure. The pH range at which this occurs depends upon the composition of the lipids. A preferred lipid system is a mixture of 1,2-distearoyl-sn-glycero-3-phosphocholine, cholesterol and dicetylphosphate. This mixture forms a negatively charged lipid construct structure under physiological conditions. The lipid construct exhibits hepatocyte targeting specificity, i.e. is specific for cellular hepatocytes, thereby allowing the construct to be targeted to the liver.

It has been discovered in the present invention that when the appropriate lipid components are formulated into a water insoluble target molecule complex using Sterile Water for Injection, USP (SWI) that has been terminally pH adjusted to pH 3.95±0.2, the overall electronic charge on the target molecule complex is predominately negative. Glargine insulin has a net positive charge at pH 5.2±0.5, which is below the isoelectric point of the protein. The positive charge on glargine insulin at pH 5.2±0.5 allows for interaction of the positively charged portion of glargine insulin with the negatively charge portion of the target molecule complex. This results in positively charged glargine insulin being attracted to the negatively charged target molecule complex. Portions of the charged glargine insulin become associated with charges on the lipids and the charged glargine insulin moves within the lipids, while other charged glargine insulin molecules are sequestered within the core volume of the lipid construct after partitioning through the various lipid moieties of the lipid construct.

There is an equilibrium between free glargine insulin in solution and glargine insulin associated with the water insoluble target molecule complex. Because the interactions between glargine insulin and the target molecule complex involve equilibria, over time free glargine insulin is able to further bind and partition into the lipid domains and/or the central core volume of the water insoluble target molecule complex. In an embodiment, free glargine insulin can be transformed into transitory lipid derivatives by adsorbing onto, or reacting with, individual molecules of lipid that are in equilibrium with the water insoluble target molecule complex. These derivatives associate with the lipids of the water insoluble target molecule complex and enter the core-volume of the complex, thus affecting the pharmacological activity of the product.

Insulins in which the isoelectric point was altered by binding charged organic molecules to insulin can be incorporated into a lipid construct. In an embodiment, recombinant human insulin isophane is incorporated into a target molecule complex comprising a lipid and multiple linked individual units formed by complexing a bridging component with a complexing agent.

Figure 12:
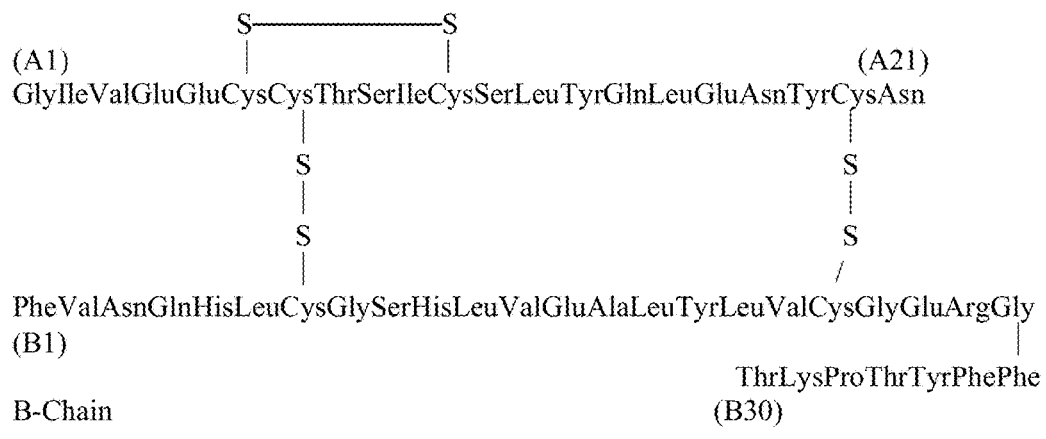
FIG. 12 is a depiction of the chemical structure of recombinant human insulin isophane and a protamine protein.

The structure of recombinant human insulin isophane and protamine are provided in FIG. 12. Recombinant human insulin isophane differs from human insulin in that recombinant human insulin has been treated with protamine such that protamine forms a coating over the insulin. The isoelectric point of recombinant human insulin isophane (pH 7.2) is higher than human insulin (pH 5.3) because the addition of protamine to recombinant human insulin isophane raises the isoelectric point of the protein. The higher isoelectric point allows recombinant human insulin isophane to remain insoluble at physiological pH. The Humulin NPH insulin product currently marketed exists as a milky suspension where recombinant human insulin isophane settles to the bottom of the vial.

In an embodiment, a pharmaceutical composition comprises a mixture of free recombinant human insulin isophane and free recombinant human regular insulin and recombinant human insulin isophane and recombinant human regular insulin that is associated with a water insoluble target molecule complex. Free recombinant human insulin isophane is the material depicted in FIG. 12. Free recombinant human insulin isophane is not associated with the target molecule complex and is insoluble at physiological pH of approximately 7.2, the isoelectric point of NPH insulin. Recombinant human regular insulin is soluble at pH 7.2.

For each of the insulins, there is an equilibrium between the free form of insulin in solution or suspension and the forms of the insulin associated with the water insoluble target molecule complex. Because the interactions between each form of insulin and the target molecule complex involve equilibria, over time the free forms of the insulins bind and partition into the lipid domains and/or the central core volume of the water insoluble target molecule complex. In an embodiment, free recombinant human insulin isophane and recombinant human regular insulin can be transformed into transitory lipid derivatives by adsorbing onto, or reacting with, individual molecules of lipid that are in equilibrium with the water insoluble target molecule complex. These derivatives associate with the lipids of the water insoluble target molecule complex and enter the core-volume of the complex, thus affecting the pharmacological activity of the product.

Description of the Invention—Method of Manufacturing the Lipid Construct

FIG. 14 demonstrates an outline for the process for manufacturing a lipid construct comprising an amphipathic lipid, an extended amphipathic lipid and insulin. The manufacture of the composition comprises three overall steps: preparing a mixture of an amphipathic lipid and an extended amphipathic lipid, preparing a lipid construct from the mixture of an amphipathic lipid and an extended amphipathic lipid, and combining insulin into the lipid construct.

Lipids are produced and loaded by the methods disclosed herein, and those methods described in U.S. Pat. Nos. 4,946,787; 4,603,044; and 5,104,661, and the references cited therein. Typically, the aqueous lipid construct formulations of the invention comprise 0.1% to 10% active agent by weight (i.e. 1-10 mg drug per ml), and 0.1% to 4% lipid by weight in an aqueous solution, optionally containing salts and buffers, in a quantity to make 100% by volume. Preferred are formulations which comprise 0.1% to 5% active agent. Most preferred is a formulation comprising 0.01% to 5% active agent by weight and up to 2% by weight of a lipid component in an amount of aqueous solution sufficient (q. s.) to make 100% by volume.

In an embodiment, the lipid construct is prepared by the following procedure. Individual lipid constituents are mixed together in an organic solvent system where the solvent had been dried over molecular sieves for approximately two hours to remove any residual water that may have accompanied the solvent. In an embodiment, the solvent system comprises a mixture chloroform and methanol in the ratio 2:1 by volume. Other organic solvents that can be easily removed from a mixture of dried lipids also can be used. Use of a single-step addition of the lipid constituents in the initial mixing procedure obviates the need for introducing any additional coupling reactions which would unnecessarily complicate the structure of the lipid construct and require additional separation procedures. The lipid components and the hepatocyte receptor binding molecule are dissolved in the solvent, then the solvent is removed under high vacuum until a dried mixture of the lipids forms. In an embodiment, the solvent is removed under vacuum using a rotoevaporator, or other methods known in the art, with slow turning at approximately 60° C. for approximately two hours. This mixture of lipids can be stored for further use, or used directly.

The lipid construct is prepared from the dried mixture of amphipathic lipids and an extended amphipathic lipid. The dried mixture of lipids are added to an appropriate amount of aqueous buffered media, then the mixture is swirled to form a homogeneous suspension. The lipid mixture is then heated with mixing at approximately 80° C. for approximately 30 minutes under a dry nitrogen atmosphere. The heated homogeneous suspension is immediately transferred to a micro-fluidizer preheated to approximately 70° C. The suspension is passed through the microfluidizer. The suspension may require additional passes through the microfluidizer to obtain a homogeneous lipid micro-suspension. In an embodiment a Model #M-110 EHI micro-fluidizer was used where the pressure on the first pass was approximately 9,000 psig. A second pass of the lipid suspension through the micro-fluidizer may be needed to produce a product that exhibits the properties of a homogeneous lipid micro-suspension. This product is defined structurally and morphologically as a three-dimensional lipid construct which contains a hepatocyte receptor binding molecule.

Insulin is loaded into the lipid constructs using one of two methods: equilibrium loading and non-equilibrium loading. Equilibrium loading of insulin begins when insulin is added to a suspension of the lipid constructs. Over time, insulin molecules move into and out of the lipid construct. The movement is governed by partitioning equilibrium, where movement into the lipid construct after the initial introduction of insulin to the suspension.

Non-equilibrium loading of insulin into the lipid constructs localizes insulin within the lipid construct. Following equilibrium loading of free insulin into the lipid construct, the bulk phase media that contains free insulin is removed. The non-equilibrium loading procedure is a vector-driven process that begins the instant the external bulk phase media is removed. The gradient potential for insulin to migrate out of the lipid constructs is eliminated when the aqueous phase containing insulin has been removed. The overall process results in a greater concentration of insulin within the final lipid construct because movement of insulin from within the construct is eliminated. The equilibrium loading of insulin is a time-dependent phenomenon whereas the non-equilibrium loading procedure is practically instantaneous. Non-equilibrium loading can be initiated by a variety of processes where the material in solution is separated from the lipid construct. Examples of such processes include, but are not limited to: filtration, centricon filtration, centrifugation, batch style affinity chromatography, streptavidin agarose affinity-gel chromatography or batch style ion-exchange chromatography. Any means that eliminates the gradient potential for insulin diffusion and leakage and causes the insulin to be retained by the lipid construct can be utilized.

When using batch-style chromatography, the affinity or ion-exchange gel is mixed rapidly with the mixture of insulin and the construct. Binding to the chromatography medium occurs rapidly and the chromatography medium is removed from the aqueous media by decanting of the aqueous phase or by using classic filtering techniques such as the use of filter paper and a Büchner funnel.

The lipid construct contains a discrete amount of loaded insulin located not only inside, but also within and on the surface of the lipid construct. The lipid construct created is a new and novel composition of matter and becomes a composition for delivering an effective amount of insulin as a result of non-equilibrium loading. The loading of insulin into this lipid construct and the subsequent removal of bulk phase insulin results in a high concentration of insulin in a lipid construct by shortening the length of time needed for removal of the external phase media. It would be difficult to achieve this level of loading insulin into the construct using time-dependent procedures, such as ion-exchange or gel-filtration chromatography, since these procedures require a constant infusion of buffer comprising high concentrations of insulin. For example, loading insulin into the construct using small scale column chromatography requires approximately twenty minutes to remove the external bulk phase media containing insulin from the construct containing insulin. Equilibrium conditions are reestablished during this time period by movement of insulin from the construct. Maintaining a high concentration of insulin in and on the lipid construct is one of the positive benefits of using non-equilibrium loading.

In an extension of the non-equilibrium loading process, cellulose acetate hydrogen phthalate is added to the lipid construct during the step of loading insulin to the lipid construct after the insulin has undergone equilibrium loading but before the non-equilibrium loading process is initiated. The nature and structure of the insulin molecule allows it to be intercalated into the lipid construct were insulin is dispersed throughout the lipid construct. Hydrophilic portions of insulin, as well as branched complex sugars and additional functional groups, extend into the bulk phase media from the surface of the lipid construct. These extended hydrophilic portions of insulin can participate in hydrogen bonding, dipole-dipole and ion-dipole interactions at the surface of the lipid construct with the hydroxyl groups, carboxyl groups and carbonyl functionalities of cellulose acetate hydrogen phthalate as illustrated in FIG. 9. Cellulose acetate hydrogen phthalate offers a unique means of combining with the molecules of the lipid construct to provide an excellent shield for masking the contents of the lipid construct from the digestive milieu of the stomach. The digestive processes in the stomach result from the hydrolytic cleavage of proteinaceous substrates by the enzyme pepsin as well as cleavage by acid hydrolysis. The acidic environment of the stomach degrades free insulin and can hydrolyze the ester bonds that hold the acyl hydrocarbon chains to the glycerol backbone in the phospholipid molecules. Hydrolytic cleavage can also occur on either side of the phosphate functionality in the phosphocholine group. The digestive system changes from the acid region of the stomach to an alkaline region of the small intestine were enzymatic action of trypsin and chymotrypsin occurs. Amino acid lysing enzymes, such as alpha amino peptidases, can degrade proteins such as insulin from the N-terminal end. The presence of cellulose acetate hydrogen phthalate in the lipid construct protects insulin from hydrolytic degradation. As the alkaline environment of the small intestine hydrolytically degrades the cellulose acetate hydrogen phthalate shield of the lipid construct the hepatocyte receptor binding molecule becomes available to direct binding of the construct to the hepatocyte binding receptor. While not wishing to be bound by any particular theory, there is a synergy of hydrolytic protection upon the addition of cellulose acetate hydrogen phthalate at the end point of non-equilibrium loading. The protection is distributed not only to insulin and individual lipid molecules, but also to the entire lipid construct. This synergy provides collective as well as individual molecular protection from enzymatic and acid hydrolysis.

In an embodiment, cellulose acetate hydrogen phthalate is covalently bound to either insulin or the lipid construct using a variety of methods. For example, one method involves coupling the hydroxyl groups on cellulose acetate hydrogen phthalate with the amine functionalities on either 1,2-diacyl-sn-glycero-3-phosphoethanolamine or the ε-amino group of the ten L-lysines in the insulin molecule utilizing the Mannich reaction.

In an embodiment, cellulose acetate hydrogen phthalate is loaded into the lipid construct during equilibrium loading of insulin into the construct. The hydroxyl and carbonyl functionalities of the cellulose acetate hydrogen phthalate hydrogen bond with lipid molecules in a lipid construct. Hydrogen bonds between cellulose acetate hydrogen phthalate and the construct are formed concurrently as insulin is loaded under equilibrium conditions into the lipid construct creating a shield around insulin and around the construct.

HDV-Insulin is recovered and recycled from aqueous media by binding it to streptavidin-agarose iminobiotin. Streptavidin covalently bound to cyanogen bromide activated agarose provides a means to separate an iminobiotin-based lipid construct from insulin in the aqueous media at the end of non-equilibrium loading of insulin into the construct. In an embodiment, an iminobiotin derivative forms the hepatocyte receptor binding portion of the phospholipid moiety within the lipid construct. The water-soluble portion of the lipid anchoring molecule extends approximately 30 angstroms from the lipid surface to facilitate binding of the hepatocyte receptor binding portion of the phospholipid moiety with a hepatocyte receptor and to aid in the attachment of the lipid construct to streptavidin.

Streptavidin reversibly binds to iminobiotin at pH values of 9.5 and greater, where the uncharged guandino functional group of iminobiotin strongly binds to one of the four binding sites on streptavidin located approximately nine angstroms below the surface of the protein. A lipid construct containing iminobiotin is removed from buffered media by raising the pH of an aqueous mixture of the construct to pH 9.5 by the addition of a 20 mM sodium carbonate-sodium bicarbonate buffer. At this pH, the bulk phase media contains free insulin which is reclaimed and separated from the lipid construct using a variety of procedures including to, but not limited to filtration, centrifugation or chromatography.

The mixture at pH 9.5 is then mixed with streptavidin-agarose cross-linked beads, where the construct is adsorbed onto the streptavidin. The beads, which are approximately 120 microns in diameter, are separated from the solution by filtration. The lipid construct is released from the streptavidin-agarose affinity-gel by reducing the pH from pH 9.5 to pH 4.5 by the addition of a 20 mM sodium acetate-acetic acid buffer at pH 4.5. At pH 4.5 the guandino group of iminobiotin becomes protonated and positively charged, as shown in FIG. 10. The lipid construct is released and separated from the streptavidin-agarose bead by filtration. The streptavidin-agarose bead are reclaimed for additional usage. Thus both free insulin and streptavidin-agarose are conserved and can be re-used.

In an embodiment, a composition that provides for the extended release of insulin is produced when iminobiotin or iminobiocytin lipid constructs are loaded with insulin using streptavidin-agarose beads. When the pH of the forementioned construct is adjusted from pH 9.5 to pH 4.5 insulin will precipitate within the lipid construct at approximately pH 5.9. The isoelectric point of insulin is at pH 5.9 and represents the pH at which insulin has its lowest water-solubility. Over a pH range from pH 5.9 to pH 6.7 insulin remains essentially insoluble and exhibits properties that are commonly attributed to particulate matter. The insolubilized insulin within a lipid construct creates a novel insulin formulation that provides for the time-release of insulin molecules when administered by subcutaneous injection or through oral dosing. Solubilization of insulin is initiated as the pH of the lipid construct approaches pH 7.4.

The lipid construct is freeze-dried or kept in a non-aqueous environment prior to dosing. In an aqueous dosage form of insulin, the pH of the insulin solution is maintained at approximately pH 6.5 in order to maintain insulin in the insoluble form. When insulin is exposed to an external pH gradient in vivo insulin is solubilized and move from the lipid construct, thereby supplying insulin to other virus-harboring tissues. Insulin remaining with the lipid construct maintains the capability of being directed to the hepatocyte binding receptor on the hepatocytes in the liver. Therefore two forms of insulin are produced from this particular lipid construct. In an in vivo setting, free and lipid associated insulin are generated in a time-dependent manner. It is anticipated that the solubilization of insulin that is lipid associated, as previously described, can be manufactured to release of insulin over a designated time-release period. This could lead to less frequent dosing schedules for patients afflicted with diabetes.

In a preferred embodiment, insulin molecules move into the lipid construct and become sequestered within the lipid domains of the loaded lipid construct. A vector-driven process is employed to move insulin molecules in one direction during the final phase of the insulin loading procedure when the chemical equilibrium is disrupted. During the final phase of insulin loading, the buffer or aqueous media is rapidly removed so that the insulin molecules associated with the lipid construct are deprived of an external media into which to migrate. Removal of the external media effectively quenches the equilibrium between insulin associated with the lipid construct and insulin solubilized in the external media. This process is termed non-equilibrium loading, as described elsewhere herein.

In an embodiment, a lipid construct is loaded with insulin using equilibrium methods, an insulin concentration of 273,000 units of insulin per microgram of protein is selected to initiate the loading procedure. Equilibrium loading continues until the lipid construct is saturated with insulin.

The end process of non-equilibrium loading of insulin into the lipid construct requires using a procedure that separates the solid lipid construct from the buffered media containing free insulin. In an embodiment, a filtration procedure with a very fine micro-pore synthetic membrane is used to separate the lipid construct from the external media. In another embodiment, a centricon device equipped with an appropriate filter with a 100,000 molecular weight cut off membrane, such as NanoSep filter is used to remove the lipid construct from the buffered media containing free insulin. The concentration of insulin in the lipid construct is maintained because associated insulin is no longer in equilibrium with the free insulin molecules located in the bulk phase media that had been removed from the construct. Free insulin which was in solution is available to load other lipid constructs. Thus, the vector-driven process of concentrating insulin within the lipid construct is achieved in one-step in essentially a time-independent procedure.

After the lipid construct is isolated from the bulk phase media, it can range in size from approximately 0.0200 microns to 0.4000 microns in diameter. Lipid constructs comprise different particle sizes that generally follow a Gaussian distribution. The appropriate size of the lipid construct needed to achieve the intended pharmacological efficacy can be selected from lipid constructs that comprise particle sizes in a Gaussian distribution by the hepatocyte binding receptor.

The lipid construct comprising insulin, lipids and the hepatocyte receptor binding molecule is prepared by using a micro-fluidization process that provides a high shear force which degrades larger lipid constructs into smaller constructs. The amphipathic lipid constituents of the lipid construct are 1,2-distearoyl-sn-glycero-3-phosphocholine, cholesterol, dicetyl phosphate, 1,2-dipalmitoyl-sn-glycero-3-phosphoethanolamine-N-(Cap Biotinyl), 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), triethylammonium 2,3-diacetoxypropyl 2-(5-((3aS,6aR)-2-oxohexahydro-1H-thieno[3,4-d]imidazol-4-yl) pentanamido)ethyl phosphate and appropriate derivatives thereof whose representative structures are depicted in Table 1.

In an embodiment, a construct comprises a target molecule complex comprising multiple linked individual units formed by complexing a bridging component with a complexing agent. Typically the target molecule complex is formed by combining the selected metal compound, e. g. chromium chloride (III) hexahydrate, with an aqueous buffered solution of the complexing agent. In an embodiment, an aqueous buffered solution of the complexing agent is prepared by dissolving the complexing agent, e.g., N-(2,6-diisopropylphenylcarbamoyl methyl)iminodiacetic acid, in an aqueous buffered solution, e.g., 10 mM sodium acetate buffer at a final pH of 3.2-3.3. The metal compound is added in excess in an amount sufficient to complex with an isolatable portion of the complexing agent, and the reaction is conducted at a temperature of 20° C. to 33° C. for 24 to 96 hours, or until the resultant complex precipitates out of aqueous buffered solution. The precipitated complexing agent, which demonstrates polymeric properties, is then isolated for future use. This complex is added to the mixture of amphipathic lipid molecules and an extended amphipathic lipid prior to preparing a lipid construct.

Methods of manufacturing a composition of an insulin in which the isoelectric point was altered by changing the amino acid sequence can be incorporated into a water insoluble target molecule complex are given below. In an embodiment, glargine insulin is incorporated into a water insoluble target molecule complex. FIG. 15 demonstrates an outline for a process for manufacturing a mixture of free glargine insulin and glargine insulin associated with a water insoluble target molecule complex. In an embodiment, the manufacture of the composition involves three overall steps: preparing a target molecule complex, incorporating the target molecule complex into a lipid construct, and combining the target molecule complex with glargine insulin to form a pharmaceutical composition.

The target molecule complex comprises multiple individual units linked together in a polymeric array. Each unit comprises a bridging component and a complexing agent. In an embodiment, the target molecule complex is formed by combining the selected metal compound, e. g. chromium chloride (III) hexahydrate, with an aqueous buffered solution of the complexing agent. In an embodiment, an aqueous buffered solution of the complexing agent is prepared by dissolving a complexing agent, e.g., N-(2,6-diisopropylphenylcarbamoylmethyl) iminodiacetic acid, in an aqueous buffered solution, e.g., 10 mM sodium acetate buffer at a final pH of 3.2-3.3. A metal compound is added in excess in an amount sufficient to complex with an isolatable portion of the complexing agent, and the reaction is conducted at a temperature of approximately 20° C. to 33° C. for approximately 24 to 96 hours, or until the resultant complex precipitates out of the aqueous buffered solution. The precipitated complex is then isolated for future use.

The precipitated complex is then mixed with the selected lipids or the lipids of the lipid construct and dissolved in an organic solvent. In an embodiment, the organic solvent is chloroform:methanol (2:1 v/v). The lipids are in a concentration sufficient to dissolve and incorporate either all or a portion of the metal complex therein. The mixture of the complex and the selected lipids that form the lipid construct are maintained at a temperature of approximately 60° C. when a high transition temperature lipid, such as 1,2-distearoyl-sn-glycero-3-phosphocholine, is employed. Lower temperatures may be used depending upon the transition temperature of the lipids selected for incorporation into the lipid construct. A time period from 30 minutes to 2 hours under vacuum is generally required to dry the lipids and remove any residual organic solvent from the lipid matrix in order to form the target molecule complex intermediate.

Lipids are produced and loaded by the methods disclosed herein, and those methods described in U.S. Pat. Nos. 4,946,787; 4,603,044; and 5,104,661, and the references cited therein. Typically, the aqueous lipid construct formulations of the invention will comprise 0.1% to 10% active agent by weight (i.e. 1-100 mg drug per ml), and 0.1% to 4% lipid by weight in an aqueous solution, optionally containing salts and buffers, in a quantity to make 100% by volume. Preferred are formulations which comprise 0.01% to 5% active agent. Most preferred is a formulation comprising 0.01% to 5% active agent by weight and up to 2% by weight of a lipid component in an amount of aqueous solution sufficient (q. s.) to make 100% by volume.

In an embodiment, glargine insulin was loaded into the target molecule complex after the pH of a suspension of the target molecule complex and Water for Injection, USP was adjusted from approximately pH 4.89±0.2 to 5.27±0.5. The pH of a solution of glargine insulin was adjusted from pH 3.88±0.2 to approximately pH 4.78±0.5, then the water insoluble target molecular complex was added. The resulting composition was a mixture of free glargine insulin and glargine insulin associated with a water insoluble target molecule complex. A portion of glargine insulin became associated with the lipid construct matrix or entrapped in the core volume of the lipid construct. This pharmaceutical composition is also referred to as HDV-glargine. In an embodiment, an aliquot of the target molecule complex is introduced into a vial of Glargine Insulin containing 100 International units of insulin/ml to provide a hepatocyte specific delivery system containing both free glargine insulin and glargine insulin associated with the target molecule complex.

A pharmaceutical composition that combines free glargine insulin and glargine insulin associated with a water insoluble target molecule complex was prepared by the following procedure. The pH of a sample of Sterile Water for Injection, USP, was adjusted to pH 3.95±0.2. An aliquot of HDV suspension was taken and its pH was adjusted in a series of steps until the final pH was 5.2±0.5. An aliquot of the Sterile Water for Injection, USP, at pH 3.95±0.2 was mixed with the suspension of the target molecule complex. The pH of the resulting suspension was 4.89±0.2. The pH of this suspension was then adjusted to pH 5.27±0.5. The pH of an aliquot of glargine insulin was adjusted from pH 3.88±0.2 to pH 4.78±0.5. This solution was then added to the suspension of the target molecule complex at pH 5.20±0.5. The resulting pharmaceutical composition is a mixture of free glargine insulin and glargine insulin associated with a water insoluble target molecule complex. This pharmaceutical composition is also referred to as HDV-glargine.

Methods of manufacturing a composition of an insulin in which the isoelectric point was altered by binding charged organic molecules to insulin can be incorporated into a water insoluble target molecule complex are given below. In an embodiment, recombinant human insulin isophane is incorporated into a water insoluble target molecule complex. FIG. 16 demonstrates an outline for a process for manufacturing a mixture of free recombinant human insulin isophane, free recombinant human regular insulin and a mixture of recombinant human insulin isophane and recombinant human regular insulin that are associated with a water insoluble target molecule complex. In an embodiment, the manufacture of the composition involves three overall steps: preparing a target molecule complex, incorporating the target molecule complex into a lipid construct that contains free and associated recombinant human regular insulin, and combining the target molecule complex with free and associated recombinant human insulin isophane to form a pharmaceutical composition.

The target molecule complex comprises multiple individual units linked together in a polymeric array. Each unit comprises a bridging component and a complexing agent. In an embodiment, the target molecule complex is formed by combining the selected metal compound, e. g. chromium chloride (III) hexahydrate, with an aqueous buffered solution of the complexing agent. In an embodiment, an aqueous buffered solution of the complexing agent is prepared by dissolving a complexing agent, e.g., N-(2,6-diisopropylphenylcarbamoylmethyl) iminodiacetic acid, in an aqueous buffered solution, e.g., 10 mM sodium acetate buffer at a final pH of 3.2-3.3. A metal compound is added in excess in an amount sufficient to complex with an isolatable portion of the complexing agent, and the reaction is conducted at a temperature of approximately 20° C. to 33° C. for approximately 24 to 96 hours, or until the resultant complex precipitates out of the aqueous buffered solution. The precipitated complex is then isolated for future use.

The precipitated complex is then mixed with the selected lipids or the lipids of the lipid construct and dissolved in an organic solvent. In an embodiment, the organic solvent is chloroform:methanol (2:1 v/v). The lipids are in a concentration sufficient to dissolve and incorporate either all or a portion of the metal complex therein. The mixture of the complex and the selected lipids that form the lipid construct are maintained at a temperature of approximately 60° C. when a high transition temperature lipid, such as 1,2-distearoyl-sn-glycero-3-phosphocholine, is employed. Lower temperatures may be used depending upon the transition temperature of the lipids selected for incorporation into the lipid construct. A time period from 30 minutes to 2 hours under vacuum is generally required to dry the lipids and remove any residual organic solvent from the lipid matrix in order to form the target molecule complex intermediate.

Lipids can be produced and loaded by the methods disclosed herein, and those methods described in U.S. Pat. Nos. 4,946,787; 4,603,044; and 5,104,661, and the references cited therein. Typically, the aqueous lipid construct formulations of the invention will comprise 0.1% to 10% active agent by weight (i.e. 1-100 mg drug per ml), and 0.1% to 4% lipid by weight in an aqueous solution, optionally containing salts and buffers, in a quantity to make 100% by volume. Preferred are formulations which comprise 0.01% to 5% active agent. Most preferred is a formulation comprising 0.01% to 5% active agent by weight and up to 2% by weight of a lipid component in an amount of aqueous solution sufficient (q. s.) to make 100% by volume.

In an embodiment, Humulin NPH insulin was added to a previously formed mixture of recombinant human regular insulin and a lipid construct. The resulting composition was a mixture of free recombinant human regular insulin and free recombinant human insulin isophane. Likewise a portion of recombinant human regular insulin and recombinant human insulin isophane is associated with the lipid construct matrix or entrapped in the core volume of the lipid construct. This pharmaceutical composition is also referred to as HDV-NPH insulin. In an embodiment, an aliquot of the target molecule complex is introduced into a vial of recombinant human insulin isophane to provide a hepatocyte specific delivery system containing both free recombinant human insulin isophane and recombinant human insulin isophane associated with the target molecule complex. In an embodiment, recombinant human insulin isophane can be combined with other forms of insulin such as the rapid acting Humalog insulin and Novolog insulin, short acting Regular® insulin, intermediate acting Lente insulin and long acting Ultralente insulin and Lantus insulin, or premixed combinations of insulin. An aliquot of recombinant human insulin isophane can be added to a mixture of the target molecule complex combined with an insulin that is not recombinant human insulin isophane.

Description of the Invention—Method of Use

Patients with Type I or Type II diabetes are administered an effective amount of a hepatocyte targeted lipid construct comprising an amphipathic lipid, an extended amphipathic lipid and insulin. When this composition is administered subcutaneously, a portion of the composition enters the circulatory system where the composition is transported to the liver and other areas where the extended amphipathic lipid binds the lipid construct to receptors of hepatocytes. A portion of the administered composition is exposed to an external gradient in vivo where insulin can be solubilized and then move from the lipid construct thereby supplying insulin to the muscle and adipose tissue. Insulin that remains with the lipid construct maintains the capability of being directed to the hepatocyte binding receptor on the hepatocytes in the liver. Therefore two forms of insulin are produced from this particular lipid construct. In an in vivo setting, free and lipid associated insulin are generated in a time-dependent manner.

The lipid construct structure of the invention provides a useful agent for pharmaceutical application for administering insulin to a host. Accordingly, the structures of the invention are useful as pharmaceutical compositions in combination with pharmaceutically acceptable carriers. Administration of the structures described herein can be via any of the accepted modes of administration for insulin that are desired to be administered. These methods include oral, parenteral, nasal and other systemic or aerosol forms.

Oral administration of a pharmaceutical composition comprising insulin associated with a target molecule complex is followed by intestinal absorption of insulin associated with the target molecule complex into the circulatory system of the body where it is also exposed to the physiological pH of the blood. The lipid construct is targeted for delivery to the liver. In an embodiment, the lipid construct is shielded by the presence of cellulose acetate hydrogen phthalate within the construct. In the case of oral administration, the shielded lipid construct transverses the oral cavity, migrates through the stomach and moves into the small intestine where the alkaline pH of the small intestine degrades the cellulose acetate hydrogen phthalate shield. The de-shielded lipid construct is absorbed into the circulatory system. This enables the lipid construct to be delivered to the sinusoids of the liver. A receptor binding molecule, such as 1,2-dipalmitoyl-sn-glycero-3-phosphoethanolamine-N-(Cap Biotinyl) or other forementioned hepatocyte specific molecules, provides a means for lipid construct to bind to the receptor and then be engulfed or endocytosed by the hepatocytes. Insulin is then released from the lipid construct where, upon gaining access to the cellular environment, it performs its designated function with regard to acting as an agent to control diabetes.

The amount of insulin administered will be dependent on the subject being treated, the type and severity of the affliction, the manner of administration and the judgment of the prescribing physician. Although effective dosage ranges for specific biologically active substances of interest are dependent upon a variety of factors, and are generally known to one of ordinary skill in the art, some dosage guidelines can be generally defined. For most forms of administration, the lipid component will be suspended in an aqueous solution and generally not exceed 4.0% (w/v) of the total formulation. The drug component of the formulation will most likely be less than 20% (w/v) of the formulation and generally greater than 0.01% (w/v).

Methods of administering a composition of an insulin in which the isoelectric point was altered by changing the amino acid sequence is incorporated into a water insoluble target molecule complex are given below. In an embodiment, patients with Type I or Type II diabetes are administered an effective amount of a hepatocyte targeted composition comprising a mixture of free glargine insulin and glargine insulin associated with a water insoluble target molecule complex. In an embodiment, glargine insulin can be combined with other forms of insulin, such as insulin lispro, insulin aspart, regular insulin, insulin zinc, human insulin zinc extended, isophane insulin, human buffered regular insulin, insulin glulisine, recombinant human regular insulin, recombinant human insulin isophane or premixed combinations of any of the aforementioned insulins, a derivative thereof, and a combination of any of the aforementioned insulins. In an embodiment, the composition can be administered by a subcutaneous or oral route.

The lipid construct structure of the invention provides a useful agent for pharmaceutical application for administering insulin to a host. Accordingly, the structures of the invention are useful as pharmaceutical compositions in combination with pharmaceutically acceptable carriers. Administration of the structures described herein can be via any of the accepted modes of administration for insulin that are desired to be administered. These methods include oral, parenteral, nasal and other systemic or aerosol forms.

After a composition is administered to a patient by subcutaneous injection, the in situ physiological environment in the injection area, the morphology and chemical structures of free glargine insulin and the glargine insulin associated with the water insoluble target molecule complex begin to change. As the pH of the environment around the free glargine insulin and the glargine insulin associated with the water insoluble target molecule complex increases after being diluted with physiological media, the pH reaches the isoelectric point of glargine insulin, where flocculation, aggregation and precipitation reactions occur for both free glargine insulin and glargine insulin associated with the target molecule complex. The rates at which these processes occur differ between free glargine insulin and glargine insulin associated with the target molecule complex. The free glargine insulin is directly exposed to changes in pH and dilution. Exposure of glargine insulin associated with the target molecule complex to small changes in pH and dilution at physiological pH is delayed due to the time required for diffusion of physiological fluids or media through the lipid bilayer in the water insoluble target molecule complex. The delay in the release of insulin from the lipid construct as well as the delay of the release of lipid construct with associated insulin within the precipitated free glargine matrix is an essential feature of the invention since it affects and augments the biological and pharmacological response in vivo.

Oral administration of a pharmaceutical composition that combines free glargine insulin and glargine insulin associated with a target molecule complex is followed by intestinal absorption of glargine insulin associated with the target molecule complex into the circulatory system of the body where it is also exposed to the physiological pH of the blood. All or a portion of the lipid construct is delivered to the liver.

As the physiological dilution is increased in situ in the subcutaneous space or upon entering into the circulatory system, the free glargine insulin and glargine insulin associated with the target molecule complex encounter a normal physiological pH environment of pH 7.4. As a result, free glargine insulin changes from a soluble form at injection, to a insoluble form at a pH near its isoelectric point of pH 5.8-6.2, and then to a soluble form at physiological pH. In the soluble form, glargine insulin migrates through the body to sites where it is capable of eliciting a pharmacological response. Glargine insulin associated with the water insoluble target molecule complex becomes solubilized and released from the complex at a different rate that is slower than that of free glargine insulin. This is because glargine insulin associated with the water insoluble target molecule complex has to traverse the core volume and lipid domains of the water insoluble target molecule complex before it contacts the bulk phase media.

The amount of glargine insulin administered will be dependent on the subject being treated, the type and severity of the affliction, the manner of administration and the judgment of the prescribing physician. Although effective dosage ranges for specific biologically active substances of interest are dependent upon a variety of factors, and are generally known to one of ordinary skill in the art, some dosage guidelines can be generally defined. For most forms of administration, the lipid component will be suspended in an aqueous solution and generally not exceed 4.0% (w/v) of the total formulation. The drug component of the formulation will most likely be less than 20% (w/v) of the formulation and generally greater than 0.01% (w/v).

Methods of administering a composition of an insulin in which the isoelectric point was altered by binding charged organic molecules to insulin is incorporated into a water insoluble target molecule complex are given below. In an embodiment, patients with Type I or Type II diabetes are administered an effective amount of a hepatocyte targeted composition comprising a mixture of free recombinant human insulin isophane plus free recombinant human regular insulin along with recombinant human insulin isophane and recombinant human regular insulin which are both are associated with a water insoluble target molecule complex. In an embodiment, recombinant human insulin isophane can be combined with other forms of insulin, such as of insulin lispro, insulin aspart, regular insulin, insulin glargine, insulin zinc, human insulin zinc extended, isophane insulin, human buffered regular insulin, insulin glulisine, recombinant human regular insulin, recombinant human insulin isophane or premixed combinations of any of the aforementioned insulins, a derivative thereof, and a combination of any of the aforementioned insulins.

The lipid construct structures of the invention provides a useful agent for pharmaceutical application for administering insulin to a host. Accordingly, the structures of the invention are useful as pharmaceutical compositions in combination with pharmaceutically acceptable carriers. Administration of the structures described herein can be via any of the accepted modes of administration for insulin that are desired to be administered. These methods include oral, parenteral, nasal and other systemic or aerosol forms.

After a composition is administered to a patient by subcutaneous injection, the in situ physiological environment in the injection area, the morphology and chemical structures of free recombinant human insulin isophane and the recombinant human insulin isophane associated with the water insoluble target molecule complex begins to change. As the pH of the environment around the free recombinant human insulin isophane and the recombinant human insulin isophane associated with the water insoluble target molecule complex becomes diluted with physiological media, some solubilization occurs for both insulins. As a result of solubilization and equilibrium conditions recombinant human insulin isophane can become associated with the target molecule complex. The rates at which these equilibrium processes occur differ between free recombinant human insulin isophane and recombinant human insulin isophane associated with the target molecule complex. The free recombinant human insulin isophane is directly exposed to small changes in pH and physiological dilution. Exposure of recombinant human insulin isophane associated with the target molecule complex to small changes in pH and dilution at physiological pH is delayed due to the time required for diffusion of physiological fluids or media through the lipid bilayer in the water insoluble target molecule complex. The delay in the release of insulin from the lipid construct as well as the delay of the release of the lipid construct as it exists within the precipitated free recombinant human insulin isophane matrix is an essential discovery of the invention since it affects and augments the biological and pharmacological response in vivo.

Oral administration of a pharmaceutical composition that combines free recombinant human insulin isophane and recombinant human insulin isophane associated with a target molecule complex is followed by intestinal absorption of recombinant human insulin isophane associated with the target molecule complex into the circulatory system of the body where it is also exposed to the physiological pH of the blood. All or a portion of the lipid construct is delivered to the liver.

As the physiological dilution is increased in situ in the subcutaneous space or upon entering into the circulatory system, free recombinant human insulin isophane and recombinant human insulin isophane associated with the target molecule complex encounter a normal physiological pH environment of pH 7.4. As a result of dilution free recombinant human insulin isophane changes from an insoluble form at injection, to a soluble form at physiological pH. In the soluble form, recombinant human insulin isophane migrates through the body to sites where it is capable of eliciting a pharmacological response. Recombinant human insulin isophane associated with the water insoluble target molecule complex becomes solubilized and released from the complex at a different rate that is slower than that of free recombinant human insulin isophane. This is because recombinant human insulin isophane associated with the water insoluble target molecule complex has to traverse the core volume and lipid domains of the water insoluble target molecule complex before it contacts the bulk phase media.

The lipid construct structure of the invention provides a useful agent for pharmaceutical application for administering recombinant human insulin isophane to a host. Accordingly, the structures of the invention are useful as pharmaceutical compositions in combination with pharmaceutically acceptable carriers. Administration of the structures described herein can be via any of the accepted modes of administration for recombinant human insulin isophane that are desired to be administered. These methods include oral, parenteral, nasal and other systemic or aerosol forms.

The amount of recombinant human insulin isophane and recombinant human regular insulin administered will be dependent on the subject being treated, the type and severity of the affliction, the manner of administration and the judgment of the prescribing physician. Although effective dosage ranges for specific biologically active substances of interest are dependent upon a variety of factors, and are generally known to one of ordinary skill in the art, some dosage guidelines can be generally defined. For most forms of administration, the lipid component will be suspended in an aqueous solution and generally not exceed 4.0% (w/v) of the total formulation. The drug component of the formulation will most likely be less than 20% (w/v) of the formulation and generally greater than 0.01% (w/v).

The amount of insulin administered will be dependent on the subject being treated, the type and severity of the affliction, the manner of administration and the judgment of the prescribing physician. Although effective dosage ranges for specific biologically active substances of interest are dependent upon a variety of factors, and are generally known to one of ordinary skill in the art, some dosage guidelines can be generally defined. For most forms of administration, the lipid component will be suspended in an aqueous solution and generally not exceed 4.0% (w/v) of the total formulation. The drug component of the formulation will most likely be less than 20% (w/v) of the formulation and generally greater than 0.01% (w/v).

Dosage forms or compositions containing active ingredient in the range of 0.005% to 5% with the balance made up from non-toxic carriers may be prepared.

The exact composition of these formulations may vary widely depending on the particular properties of the drug in question. However, they will generally comprise from 0.01% to 5%, and preferably from 0.05% to 1% active ingredient for highly potent drugs, and from 2%-4% for moderately active drugs.

The percentage of active ingredient contained in such parenteral compositions is highly dependent on the specific nature thereof, as well as the activity of the active ingredient and the needs of the subject. However, percentages of active ingredient of 0.01% to 5% in solution are employable, and will be higher if the composition is a solid which will be subsequently diluted to the above percentages. Preferably the composition will comprise 0.2%-2.0% of the active agent in solution.

The formulations of the pharmaceutical compositions described herein may be prepared by any method known or hereafter developed in the art of pharmacology. In general, such preparatory methods include the step of bringing the active ingredient into association with a carrier or one or more other ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, parenteral, pulmonary, intranasal, buccal, or another route of administration.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. However, delivery of the active agent as set forth in the invention may be as low as $1/10$, $1/100$ or $1/1,000$ or smaller than the dose normally administered because of the targeted nature of the insulin therapeutic agent.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate.

Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, kaolin or cellulose acetate hydrogen phthalate.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a lipid construct preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 microns, and preferably from about 1 to about 6 microns. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 microns and at least 95% of the particles by number have a diameter less than 7 microns. More preferably, at least 95% of the particles by weight have a diameter greater than 1 nanometer and at least 90% of the particles by number have a diameter less than 6 microns. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 microns.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 microns. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 75% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 microns, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1%-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a lipid construct preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically dosages of the active ingredient in the composition of the invention which may be administered to an animal, preferably a human, range in amount from 1 micrograms to about 100 g per kilogram of body weight of the animal. While the precise dosage administered will vary depending upon any number of factors, including but not limited to, the type of animal and type of disease state being treated, the age of the animal and the route of administration. Preferably, the dosage of the active ingredient will vary from about 1 mg to about 10 g per kilogram of body weight of the animal. More preferably, the dosage will vary from about 10 mg to about 1 g per kilogram of body weight of the animal.

The composition may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled physician and will depend upon any number of factors, such as, but not limited to, the type and severity of the disease being treated, the type and age of the animal, etc.

The invention also includes a kit comprising the composition of the invention and an instructional material which describes administering the composition to a tissue of a mammal. In another embodiment, this kit comprises a (preferably sterile) solvent suitable for dissolving or suspending the composition of the invention prior to administering the composition to the mammal.

As used herein, an "instructional material" includes a publication, a recording, a diagram, or any other medium of expression which can be used to communicate the usefulness of the protein of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the components of the invention or be shipped together with a container which contains the components of the invention. Alternatively, the instructional material may be shipped separately from the container with the intention that the instructional material and the composition be used cooperatively by the recipient.

The pharmaceutical compositions useful for practicing the invention may be administered to deliver a dose equivalent to standard doses of insulin.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, companion animals and other mammals.

Pharmaceutical compositions that are useful in the methods of the invention may be prepared, packaged, or sold in formulations suitable for oral or injectable routes of administration.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

The materials and methods used in the experiments presented in this Experimental Example are now described.

Experimental Example 1. Pharmaceutical Composition 1

A lipid construct comprises a mixture of the lipids 1,2-distearoyl-sn-glycero-3-phosphocholine, cholesterol, dicetyl phosphate, 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycerol)] (sodium salt), the receptor binding molecule 1,2-dipalmitoyl-sn-glycero-3-phosphoethanolamine-N-(Cap Biotinyl) and insulin.

Experimental Example 2. Pharmaceutical Composition 2

A lipid construct comprises a mixture of the lipids 1,2-distearoyl-sn-glycero-3-phosphocholine, cholesterol, dicetyl phosphate, 1,2-distearoyl-sn-glycero-3-phosphoethanolamine, 1,2-dipalmitoyl-sn-glycero-3-phosphoethanolamine-N-(succinyl), 1,2-dipalmitoyl-sn-glycero-3-[phospho-rac-(1-glycero)] (sodium salt), insulin, the receptor binding molecule 1,2-dipalmitoyl-sn-glycero-3-phosphoethanolamine-N-(Cap Biotinyl), and/or polychromium-poly(bis)-[N-(2,6-(diisopropylphenyl) carbamoylmethyl) imino]diacetic acid]. The lipid anchoring-hepatocyte receptor binding molecule 1,2-dipalmitoyl-sn-glycero-3-phosphoethanolamine-N-(Cap Biotinyl) and polychromium-poly(bis)-[N-(2,6-(diisopropylphenyl)carbamoyl methyl) imino diacetic acid] had been added to the lipid construct at a level of 1.68%±0.5% by weight and 1.2%±0.5% by weight, respectively.

Experimental Example 3. Pharmaceutical Composition 3

A lipid construct comprises a mixture of the amphipathic lipids 1,2-distearoyl-sn-glycero-3-phosphocholine (12.09 g), cholesterol (1.60 g), dicetyl phosphate (3.10 g), polychromium-poly(bis)-[N-(2,6-(diisopropylphenyl) carbamoylmethyl)imino] diacetic acid] (0.20 g) and insulin. The mixture was added to a aqueous medium and the total mass was 1200 g.

Experimental Example 4. Preparation of a Lipid Construct Containing Insulin

The lipid construct was formed by preparing a mixture of amphipathic lipid molecules and an extended amphipathic lipid, preparing a lipid construct from the mixture of amphipathic lipid molecules and an extended amphipathic lipid, and combining insulin into the lipid construct.

A mixture of amphipathic lipid molecules and an extended amphipathic lipid was produced using the following procedure. A mixture of the lipid components [total mass of 8.5316 g] of the lipid construct was prepared by combining aliquots of the lipids 1,2-distearoyl-sn-glycero-3-phosphocholine (5.6881 g), cholesterol crystalline (0.7980 g), dicetyl phosphate (1.5444 g), 1,2-dipalmitoyl-sn-glycero-3-phosphoethanolamine-N-(Cap Biotinyl) (0.1436 g), 1,2-distearoyl-sn-glycero-3-phosphoethanolamine (0.1144 g), 1,2-dipalmitoyl-sn-glycero-3-phosphoethanolamine-N-(succinyl) (0.1245 g) and 1,2-dipalmitoyl-sn-glycero-3-[phospho-rac-(1-glycerol)] (sodium salt) (0.1186 g).

A 100 ml solution of chloroform:methanol (2:1 v:v) was dehydrated over 5.0 grams of molecular sieves. The mixture of the lipid components of lipid construct was placed in a 3 liter flask and 45 mls of the chloroform/methanol solution was added to the lipid mixture. The solution was placed in flask on a rotoevaporator with a water bath at 60° C.±2° C. and turned slowly. The chloroform/methanol solution was removed under vacuum on a rotary evaporator using an aspirator for approximately 45 minutes, followed by a vacuum pump for approximately two hours to remove residual solvent, and the solid mixture of the lipids formed. The dried mixture of lipids can be stored in a freezer at approximately −20° C.-0° C. for an indefinite time period.

The lipid construct was prepared from the mixture of amphipathic lipid molecules and an extended amphipathic lipid using the following procedure. The lipid mixture was mixed with approximately 600 ml of 28.4 mM sodium phosphate (monobasic-dibasic) buffer at pH 7.0. The lipid mixture was swirled, then placed in a heated water bath at 80° C.±4° C. for 30 minutes while slowly turning to hydrate the lipids.

A M-110 EHI microfluidizer was preheated to 70° C.±10° C. using SWI with a pH between 6.5-7.5. The suspension of the hydrated target complex was transferred to the microfluidizer and microfluidized at approximately 9000 psig using one pass of the suspension of the hydrated target molecule complex through the fluidizer. After passing through the microfluidizer, an unfiltered sample (2.0-5.0 ml) of the fluidized suspension was collected for particle size analysis using unimodal distribution data from a Coulter N-4 plus particle size analyzer. Prior to all particle size determinations, the sample was diluted with 0.2 micron filtered SWI that has been pH adjusted to between 6.5-7.5. The particle size was required to range from 0.020-0.40 microns. If the particle size was not within this range, the suspension was passed through the microfluidizer again at approximately 9000 psig, and the particle size was analyzed again until the particle size requirements are reached. The microfluidized target molecule complex was collected in a sterile container.

The microfluidized target molecule complex was maintained at 60° C.±2° C. while filtered twice through a sterile 0.8 micron+0.2 micron gang filter attached to a 5.0 ml syringe. An aliquot of the filtered suspension was analyzed to determine the particle size range of particles in the suspension. The particle size range of the final 0.2 micron filtered sample should be in the range from 0.0200-0.2000 microns as determined from the unimodal distribution printout from the particle size analyzer.

Insulin is loaded into the construct by reverse loading of the construct using the methods described in U.S. Pat. No. 5,104,661, which is incorporated herein by reference.

Experimental Example 5. Method of Use

The efficacy of hepatic directed vesicle (HDV) insulin on hepatic glycogen was evaluated in a rat model. A total of 60 Male Sprague-Dawley rats (8 weeks of age; 250 g) were divided into five treatment groups as described below.

For the first day of the study, all rats were fasted for 24 hours with ab libitum water. On the second day, the rats were injected intraperitoneally with a mixture of alloxan and streptozotocin (AS). The mixture of alloxan and streptozotocin was prepared in pH 7 0.01 M phosphate buffer by weighing 5 mg per mL of each material so that the final concentration is 5 mg alloxan per mL and 5 mg streptozotocin per mL. The AS mixture was administered 0.5 mL of the mixture of alloxan and streptozotocin via intraperitoneal injection at 20 mg/kg body weight (10 mg/kg alloxan and 10 mg/kg streptozotocin). AS will cause a massive release of insulin resulting in a profound and transient hypoglycemia a few hours after injecting AS. A 10% glucose in water solution was injected subcutaneously as needed to prevent hypoglycemia and keep the rats adequately hydrated during the second day. A normal chow diet and water were available ad libitum.

On the third day, a baseline tail-vein blood glucose sample is taken at 0 Minutes, followed immediately by a subcutaneous injection of one of the following solutions at 0.32 U insulin/rat, corresponding to the group to which the rat was assigned.

(1) HDV-insulin with a Cr-disofenin [polychromium-poly(bis)-[N-(2,6-(diisopropylphenyl) carbamoyl methyl) imino diacetic acid]] hepatocyte target molecule (HTM) (Positive) control. There was no extended amphipathic lipid present. The amount of amphipathic lipids present provided a dose of about 14.5 micrograms of amphipathic lipids per kilogram of rat.

(2) Regular insulin (negative) control;

(3) HDV-insulin test material 1, where the extended amphipathic lipid was Biotin-X DHPE [triethylammonium 2,3-diacetoxypropyl 2-(6-(5-((3aS,6aR)-2-oxohexahydro-1H-thieno[3,4-d]imidazol-4-yl) pentanamido)hexanamido) ethyl phosphate]. The amount of amphipathic lipids present provided a dose of about 14.5 micrograms of amphipathic lipids per kilogram of rat. The amount of extended amphipathic lipid present provided a dose of about 191 nanograms of extended amphipathic lipid per kilogram of rat.

(4) HDV-insulin test material 2, where the extended amphipathic lipid was Biotin DHPE [triethylammonium 2,3-diacetoxypropyl 2-(5-((3aS,6aR)-2-oxohexahydro-1H-thieno[3,4-d]imidazol-4-yl) pentanamido)ethyl phosphate]. The amount of amphipathic lipids present provided a dose of about 7.25 micrograms of amphipathic lipids per kilogram of rat. The amount of extended amphipathic lipid present provided a dose of about 95.5 nanograms of extended amphipathic lipid per kilogram of rat.

(5) HDV-insulin test material 3, where the extended amphipathic lipid was Biotin DHPE [triethylammonium 2,3-diacetoxypropyl 2-(5-((3aS,6aR)-2-oxohexahydro-1H-thieno[3,4-d]imidazol-4-yl) pentanamido)ethyl phosphate]. The amount of amphipathic lipids present provided a dose of about 14.5 micrograms of amphipathic lipids per kilogram of rat. The amount of extended amphipathic lipid present provided a dose of about 191 nanograms of extended amphipathic lipid per kilogram of rat.

For treatment groups 1 and 3-5, the amphipathic lipids were a mixture of 1,2-distearoyl-sn-glycero-3-phosphocholine, cholesterol, and dicetyl phosphate.

At "0" minutes, each rat was also gavaged with 375 mg glucose in 3.75 ml water (10% glucose).

Half of the animals of each group were anesthetized and euthanized using ketamine (150 mg/kg)/xylazine (15 mg/kg) at one hour minutes and the remaining rats at 2 hours via I.P. Previous studies with Cr-disofenin HTM have shown the statistically significant effect over 2 hours. The entire liver was removed and stored in liquid nitrogen at −80° C. until analyzed for hepatic glycogen.

Hepatic glycogen was determined by the following procedure which is described by Ong K C and Kho H E, Life Sciences 67 (2000) 1695-1705. Weighed amounts (0.3-0.5 g) of frozen liver tissue were homogenized in 10 volumes of ice-cold 30% KOH and then boiled at 100° C. for 30 minutes. Glycogen was precipitated with ethanol, pelleted, washed, and resolubilized in distilled water. Glycogen content was determined by treating the aqueous solution with anthrone reagent (1 g anthrone dissolved in 500 ml conc. $H_2SO_4$). The absorbance of the solution at 625 nm was measured in a spectrometer and the amount of glycogen present was calculated.

Figure 17:
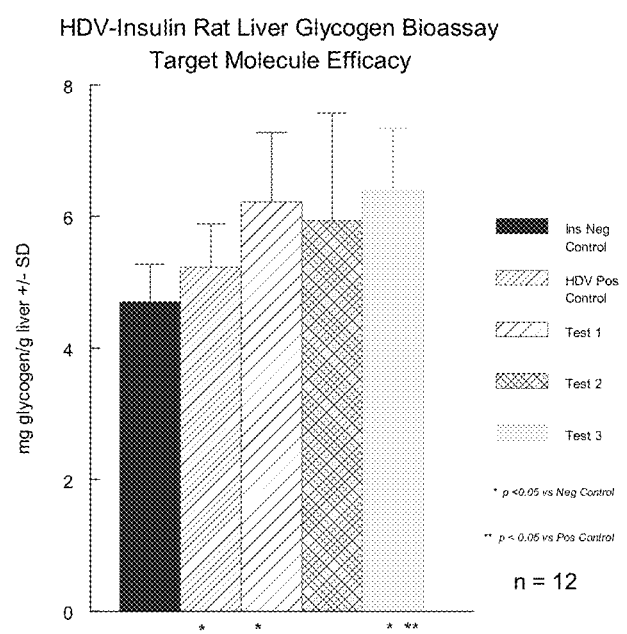
FIG. 17 indicates the concentration of glycogen present in the liver of rats treated with various hepatocyte targeted compositions.
Figure 18:
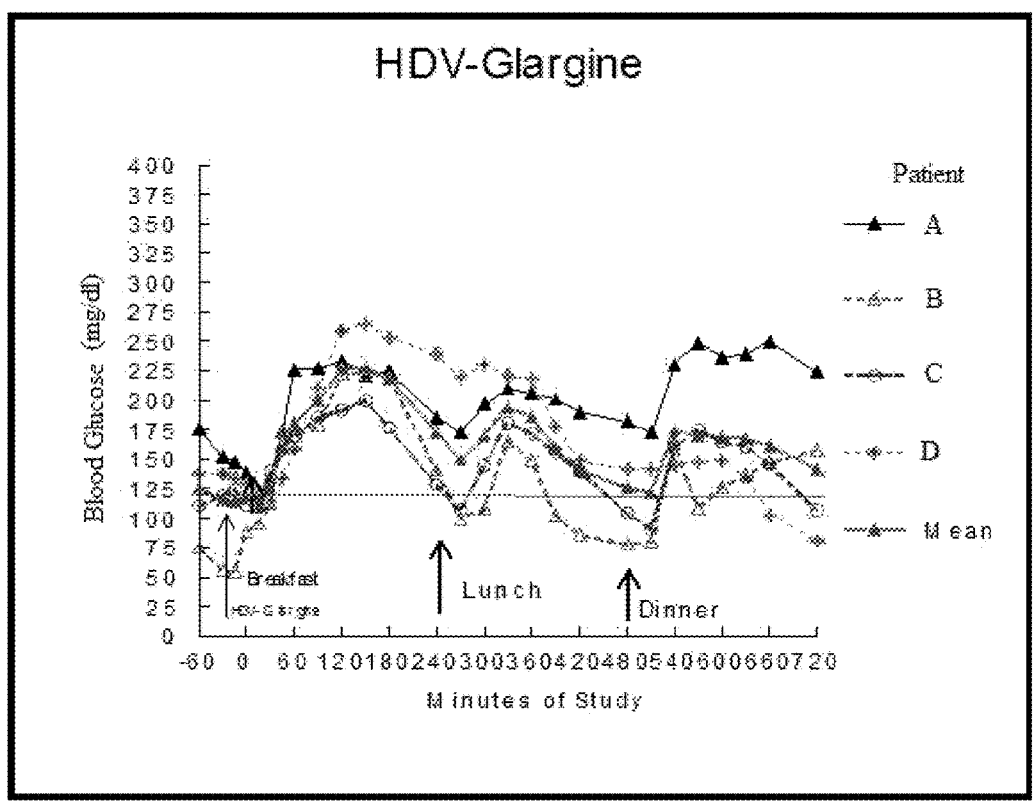
FIG. 18 is a graph of the concentrations of glucose in blood of individual patients treated once before breakfast with HDV-glargine insulin.
Figure 19:
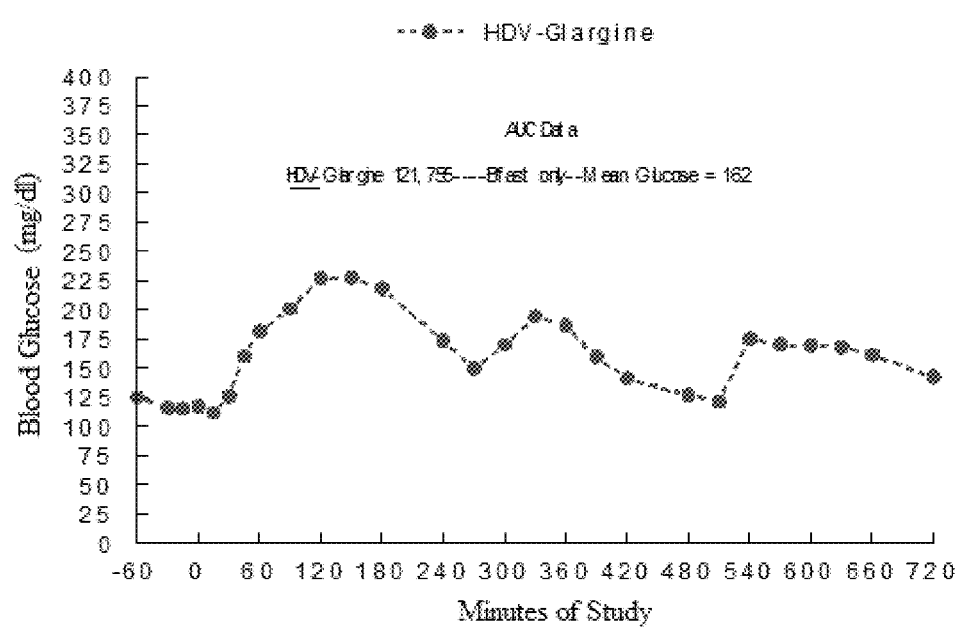
FIG. 19 is a graph of the effect of a single dose of HDV-glargine insulin on average blood glucose concentrations in patients consuming three meals during the day.
Figure 20:
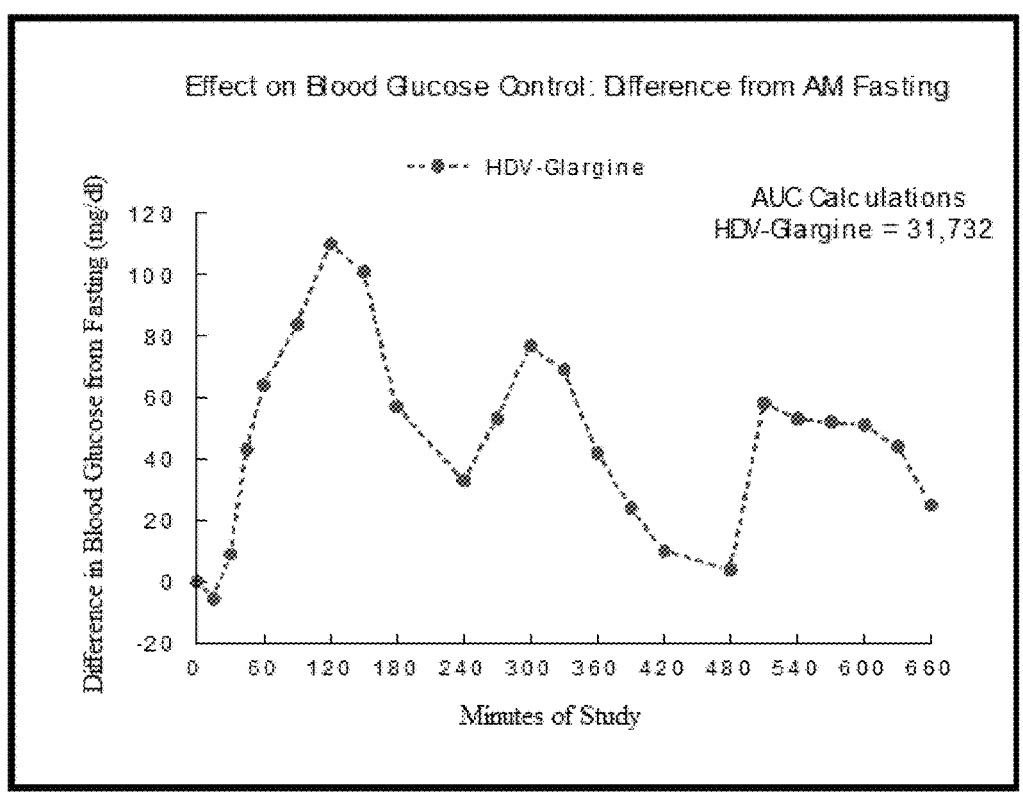
FIG. 20 is a graph of the effect of HDV-glargine insulin on blood glucose concentrations over time relative to blood glucose concentrations during fasting.
Figure 21:
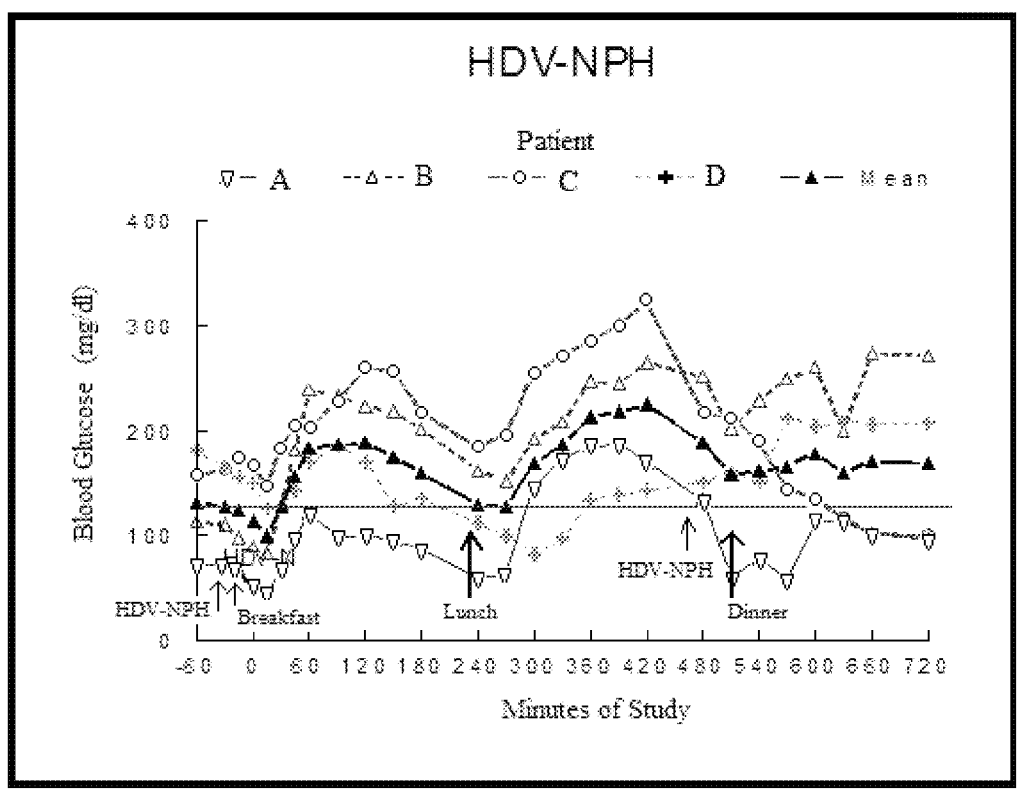
FIG. 21 is a graph of the concentrations of glucose in blood of individual patients treated once before breakfast with HDV-Humulin NPH insulin.
Figure 22:
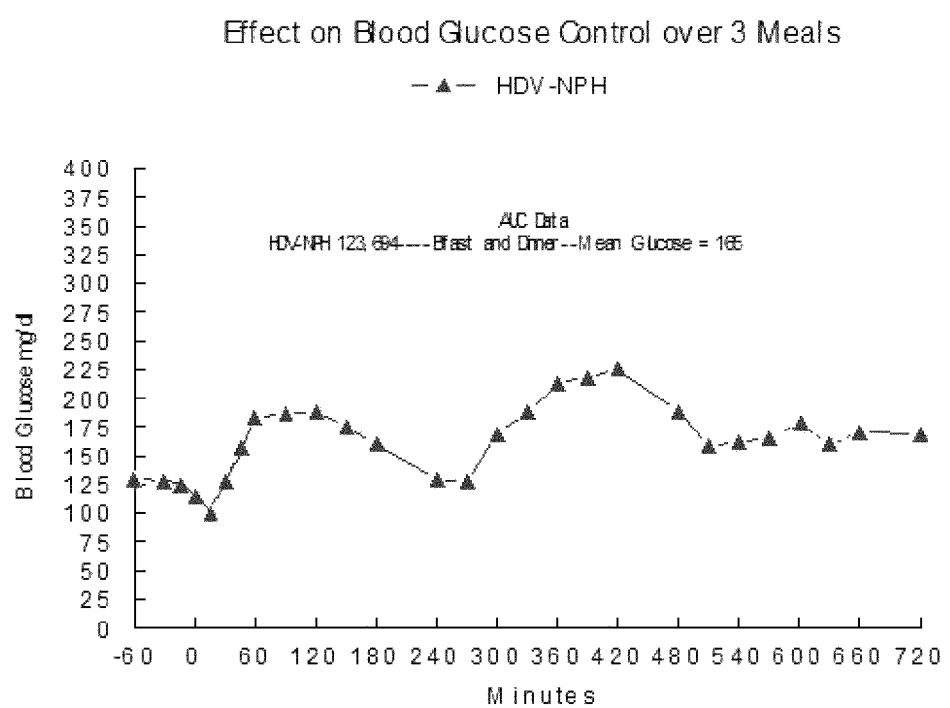
FIG. 22 is a graph of the effect of a single dose of HDV-Humulin NPH insulin on average blood glucose concentrations in patients consuming three meals during the day.
Figure 23:
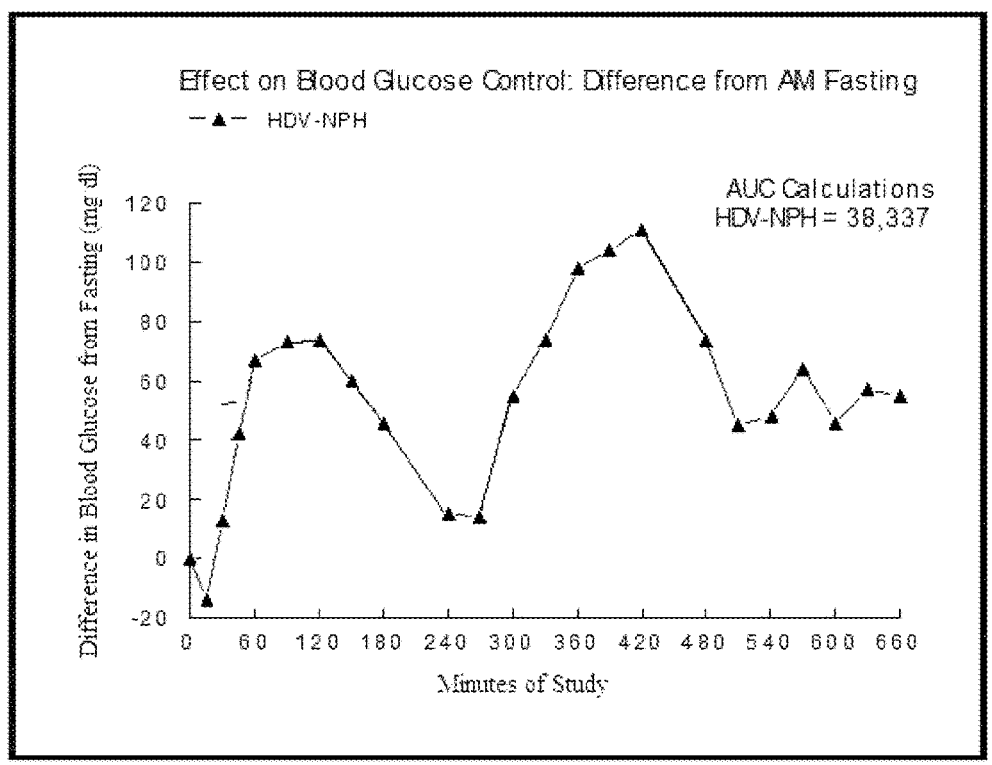
FIG. 23 is a graph of the effect of HDV-Humulin NPH insulin on blood glucose concentrations over time relative to blood glucose concentrations during fasting.

The results are shown in FIG. 17, which compares the concentration of glycogen present in the liver for the five treatment groups. The values are the average of the one and two hour values, which were similar to each other. Regular insulin, which has been shown to be ineffective as a stimulant for hepatic glucose and glycogen storage, was used as a negative control. HDV-Insulin with the Cr-disofenin HTM was the positive control and it had a significantly higher glycogen content ($p<0.05$) than did the regular insulin negative control. Thus the expected statistical and biologically significant differences between the negative and positive controls post dosing were observed.

Test materials 1 and 3, which had the extended amphipathic lipids biotin DHPE [triethylammonium 2,3-diacetoxypropyl 2-(5-((3aS,6aR)-2-oxohexahydro-1H-thieno[3,4-d]imidazol-4-yl) pentanamido)ethyl phosphate] and biotin-X DHPE [triethylammonium 2,3-diacetoxypropyl 2-(6-(5-((3aS,6aR)-2-oxohexahydro-1H-thieno[3,4-d]imidazol-4-yl) pentanamido)hexanamido) ethyl phosphate] had statistically higher ($p=0.05$) glycogen levels than did the regular insulin. Test material 2, which also had biotin-X DHPE, but with lipid concentrations one-half of those in test material 3, had glycogen levels that were higher, but the within group variability was great enough to give a $p=0.08$.

Experimental Example 6. Pharmaceutical Composition of HDV-Glargine Insulin

A hepatocyte targeted composition comprises a mixture of free glargine insulin and glargine insulin associated with a water insoluble target molecule complex. The complex comprises multiple linked individual units and a lipid construct matrix, comprising a mixture of 1,2-distearoyl-sn-glycero-3-phosphocholine, cholesterol, dicetyl phosphate. The bridging agent polychromium poly(bis) [N-(2,6-diisopropylphenylcarbamoylmethyl) iminodiacetic acid] is present within the complex.

Experimental Example 7. Preparation of HDV-Glargine Insulin

An intermediate mixture of the components of a target molecule complex was produced by the following procedure. A mixture of the components [total mass of 2.830 g] of a target molecule complex was prepared by adding aliquots of the lipids 1,2-distearoyl-sn-glycero-3-phosphocholine (2.015 g), crystalline cholesterol (0.266 g), and dicetyl phosphate (0.515 g) to the bridging agent, polychromium poly(bis) [N-(2,6-diisopropylphenylcarbamoylmethyl) iminodiacetic acid] (0.034 g). A solution of chloroform (50 ml) and methanol (25 ml) had been dehydrated over molecular sieves. The mixture of the components of the target molecule complex was added to the chloroform/methanol solution, which was then placed in a water bath at 60° C.±2° C. to form a solution. The chloroform/methanol solution was removed under vacuum on a rotary evaporator using an aspirator, followed by a vacuum pump, and the solid intermediate mixture formed.

A target molecule complex was produced by the following process. The pH of 530 ml of Sterile Water for Injection, USP (SWI) was adjusted to between pH 6.5-7.5 by the addition of a 105 µl of 0.1 N NaOH solution. Sufficient water was added to make 200 g of product. The pH adjusted SWI was added to the intermediate mixture (2.830 g) and the intermediate mixture was hydrated by placing the mixture in a water bath at 80° C.±2° C. while rotating the mixture for approximately 30 minutes±15 minutes, or until the mixture was a uniform appearing suspension. During the previous process, the pH of the suspension decreased. The pH of the suspension was then adjusted to pH 5.44±0.5 pH units by the addition of approximately 1.0 ml 0.1 N NaOH.

The suspension of the hydrated target complex was transferred to a model M-110 EHI microfluidizer that was preheated to 70° C.±10° C. with 28 mM sodium phosphate buffer at pH 7.0. The suspension was microfluidized at 9,000 psig using one pass of the suspension of the hydrated target molecule complex through the fluidizer. After passing through the microfluidizer, an unfiltered sample (2.0-5.0 ml) of the fluidized suspension was collected for particle size analysis using unimodal distribution data from a Coulter N-4 plus particle size analyzer. Prior to all particle size determinations, the sample was diluted with 0.2 micron filtered SWI that has been pH adjusted to between 6.5-7.5. The particle size was required to range from 0.020-0.40 microns. If the particle size was not within this range, the suspension was passed through the microfluidizer again, and the particle size was analyzed again until the particle size requirements was reached. The microfluidized target molecule complex was collected in a sterile container.

The suspension of the microfluidized target molecule complex was maintained at 60° C.±2° C. while filtered twice through a sterile 0.8 micron+0.2 micron gang filter attached to a 5.0 ml syringe. An aliquot of the filtered suspension was analyzed to determine the particle size range of particles in the suspension. The particle size of the final 0.2 micron filtered sample was in the range from 0.0200-0.2000 microns, as determined from the unimodal distribution printout from the particle size analyzer. The pH of the filtered suspension of the target molecule complex was 3.74±0.2 pH units before pH adjustment. Samples were stored in a refrigerator between 2°-8° C. until further use.

The pharmaceutical composition comprising a mixture of free glargine insulin and glargine insulin associated with a water insoluble target molecule complex, also referred to as HDV-glargine insulin, was produced was produced by the following process. The pH of a 5.0 ml aliquot of the twice filtered suspension of the target molecule complex was adjusted from an initial pH of pH 3.74±0.2 to pH 5.2±pH 0.5 by the sequential addition of sterile 0.1 NaOH according to the following procedure:

pH 3.74+10 µl 0.1 N NaOH→pH 3.96
pH 3.96+20 µl 0.1 N NaOH→pH 4.52
pH 4.52+10 µl 0.1 N NaOH→pH 4.69
pH 4.69+10 µl 0.1 N NaOH→pH 5.01
pH 5.01+10 µl 0.1 N NaOH→pH 5.20

A 1.6 ml aliquot of the target molecule complex suspension at pH 5.20±0.5 was combined with 18.4 ml of SWI, which had been adjusted to pH 3.95±0.2. The pH of the resulting suspension was adjusted from pH 4.89 to pH 5.27±0.5 by the addition of 10 µl±1.0 µl of 0.1 N NaOH.

The pH of 5.0 ml aliquot of Lantus® Glargine—U-100 Insulin was increased from pH 3.88±0.2 to pH 4.78±0.5 by the addition of 60 µl±2 µl of sterile 0.1 N NaOH with mixing. A 2.5 ml±0.1 ml aliquot of the target molecule complex suspension at pH 5.27±0.5 was added to 5.0 ml±0.1 ml of the solution of Glargine insulin at pH 4.78±0.5 to produce the pharmaceutical composition containing a mixture of free glargine insulin and glargine insulin associated with the water insoluble target molecule complex. The product contained 66.1 IU of glargine insulin/ml suspension. In an embodiment, the mixture of free glargine insulin and glargine insulin associated with the complex can be produced in a vial of glargine insulin in situ in order to manufacture individual dosage forms.

Example 8. Method of Use of HDV-Glargine Insulin for the Control of Blood Glucose in Type I Diabetes Mellitus Patients HDV-glargine insulin was administered to patients to determine the ability of HDV-glargine insulin to control post prandial blood glucose levels. Seven Type I diabetes mellitus patients were selected. The patients were carefully screened and selected according to criteria listed in the study protocol. The patients were treated with basal glargine insulin and a short-acting insulin at meal times prior to entering the HDV-glargine insulin treatment period. Patients were monitored (via diary cards and site contact) for four days prior to administering HDV-glargine insulin to assure that they were in acceptable control of their blood glucose levels. Morning fasting glucose levels were established to be in the range of 100-150 mg/dl.

During the study, the dose of HDV-glargine insulin for each patient was 1.2× their usual daily dose of basal glargine insulin to compensate for the amount of short-acting insulin that they would not receive on the test days. Blood samples were taken according to a set schedule over 13 hours. HDV was added to glargine insulin using the method previously described to produce a suspension with a final concentration of 66.1 IU glargine/ml and 0.37 mg HDV/ml. The patients were injected with HDV-glargine insulin one hour prior to the morning breakfast. At each of the three daily meals, breakfast, lunch and dinner, a 60 gram carbohydrate meal was prescribed by a dietitian.

The results of the experiments presented in this Experimental Example are now described. HDV-glargine insulin was well tolerated by the patients and no adverse reactions were observed at the injection sites. Hypoglycemic reactions were not observed in patients receiving this treatment. The blood glucose values of patients treated with HDV-glargine insulin are graphically presented in FIG. 18. FIG. 18 shows that blood glucose concentrations increased, as anticipated, following meals and glucose concentrations decreased over time until the next meal was eaten. This pattern was observed for all four patients. FIG. 19 shows the effect of a single dose of HDV-glargine insulin on average blood glucose concentrations in patients consuming three meals during the day. As with the individual patients, blood glucose concentrations increased following meals and glucose concentrations decreased over time until the next meal was eaten. Average blood glucose concentrations were above the baseline value at all time points. The curve suggests that the efficacy of HDV-glargine insulin improved throughout the day because there was less variation between the high and low concentrations after the lunch and dinner meals than the breakfast meal. The effect of HDV-glargine insulin on blood glucose concentrations over time relative to blood glucose concentrations during fasting are shown in FIG. 20. Blood glucose concentrations increased following meals then decreased over time towards the glucose concentration during fasting until the next meal was eaten. Blood glucose concentrations were above fasting concentrations throughout the study. Treatment of patients with HDV-glargine insulin resulted in some degree of post-prandial blood glucose level control, indicating that HDV was able to carry sufficient quantities of glargine-insulin to the liver at mealtimes to provide this control. Blood glucose levels were typical of Type I patients that usually receive basal insulin therapy plus short-acting insulins at meal times.

Experimental Example 9. Pharmaceutical Composition of HDV-Humulin NPH Insulin #1

A hepatocyte targeted composition comprises a mixture of free recombinant human insulin isophane and recombinant human insulin isophane associated with a water insoluble target molecule complex. The complex comprises multiple linked individual units and a lipid construct matrix comprising a mixture of 1,2-distearoyl-sn-glycero-3-phosphocholine, cholesterol, dicetyl phosphate. The bridging agent polychromium poly(bis)[N-(2,6-diisopropylphenylcarbamoylmethyl) iminodiacetic acid] is present within the complex.

Experimental Example 10. Pharmaceutical Composition of HDV-Humulin NPH Insulin #2

A hepatocyte targeted composition comprises a mixture of free recombinant human insulin isophane, free recombinant human regular insulin, and recombinant human insulin isophane and recombinant human regular insulin associated with a water insoluble target molecule complex. The complex comprises multiple linked individual units and a lipid construct matrix comprising a mixture of 1,2-distearoyl-sn-glycero-3-phosphocholine, cholesterol, dicetyl phosphate. The bridging agent polychromium poly(bis)[N-(2,6-diisopropylphenylcarbamoylmethyl) iminodiacetic acid] is present within the complex.

Experimental Example 11. Preparation of HDV-Humulin NPH Insulin

An intermediate mixture of the components of a target molecule complex was produced by the following procedure. A mixture of the components [total mass of 2.830 g] of a target molecule complex was prepared by adding aliquots of the lipids 1,2-distearoyl-sn-glycero-3-phosphocholine (2.015 g), crystalline cholesterol (0.266 g), and dicetyl phosphate (0.515 g) to the bridging agent, polychromium poly(bis)[N-(2,6-diisopropylphenylcarbamoylmethyl) iminodiacetic acid] (0.034 g). A solution of chloroform (50 ml) and methanol (25 ml) had been dehydrated over molecular sieves. The mixture of the components of the target molecule complex was added to 25.0 mls the chloroform/methanol solution, which was then placed in a water bath at 60° C.±0.2 C to form a solution. The chloroform/methanol solution was removed under vacuum on a rotary evaporator using an aspirator, followed by a vacuum pump, and the solid intermediate mixture formed.

A target molecule complex was produced by the following process. Approximately 200 ml of 28 mM sodium phosphate buffer at pH 7.0 was added to the intermediate mixture to form a aqueous suspension. The aqueous suspension was hydrated in a water bath at 80° C.±2° C. while rotating the mixture for approximately 30 minutes±15 minutes or until the mixture was a uniform appearing suspension.

The suspension of the hydrated target complex was transferred to a model M-110 EHI microfluidizer that was preheated to 70° C.±10° C. with 28 mM sodium phosphate buffer at pH 7.0. The suspension was microfluidized at 9,000 psig using one pass of the suspension of the hydrated target molecule complex through the fluidizer. After passing through the microfluidizer, an unfiltered sample (2.0-5.0 ml) of the fluidized suspension was collected for particle size analysis using unimodal distribution data from a Coulter N-4 plus particle size analyzer. Prior to all particle size determinations, the sample was diluted with 28 mM sodium phosphate buffer pH 7.0. If the particle size was not within the range of 0.020-0.40 microns, the suspension was passed through the microfluidizer again, and the particle size was analyzed again. This is repeated until the particle size is within the range of 0.020-0.40 microns. The suspension of the microfluidized target molecule complex was collected in a sterile container.

The suspension of the microfluidized target molecule complex was maintained at 60° C.±2° C. while filtered through a sterile 0.8 micron+0.2 micron gang filter attached to a 5.0 ml syringe. An aliquot of the filtered suspension was analyzed to determine the particle size range of particles in the suspension. The particle size of the final 0.2 micron filtered sample was in the range from 0.0200-0.2000 microns, as determined from the unimodal distribution printout from the particle size analyzer. The pH of the filtered suspension of the target molecule complex was 7.0±0.5 pH units. Samples were stored in a refrigerator between 2°-8° C. until further use.

The filtered HDV-lipid suspension contained 14.15 mg of HDV lipid/ml. A 0.8 ml aliquot of this suspension was added to a 10.0 ml vial of Humulin R insulin and allowed to incubate for several days at 2°-8° C. Then 5.0 ml of the 10.0 ml Humulin R insulin HDV suspension was removed with a sterile syringe. To the remaining 5.0 ml of Humulin R insulin in the vial, 5.0 ml of Humulin NPH insulin was added to form the final HDV product. The final HDV composition contained 93.6 units of combined HDV Humulin R and HDV Humulin NPH insulin/ml of suspension and 0.52 mg of HDV lipid/ml. This composition, which can be produced in situ to manufacture individual dosage forms, comprised a mixture of free Humulin R insulin, free Humulin NPH insulin and both Humulin R insulin and Humulin NPH insulin associated with a lipid construct.

Example 12. Method of Use of Combined HDV Humulin R Insulin and HDV-Humulin NPH Insulin for the Control of Blood Glucose in Type I Diabetes Mellitus Patients HDV-Humulin NPH insulin was administered to patients to determine the ability of HDV-Humulin NPH insulin to control post prandial blood glucose levels. Seven Type I diabetes mellitus patients were selected. The patients were carefully screened and selected according to criteria listed in the study protocol. The patients were treated with basal Humulin NPH insulin and a short-acting insulin at meal times prior to entering the HDV-Humulin NPH insulin treatment period. Patients were monitored (via diary cards and site contact) for four days prior to administering HDV-Humulin NPH insulin to assure that they were in acceptable control of their blood glucose levels. Morning fasting glucose levels were established to be in the range of 100-150 mg/dl.

During the study, the dose of HDV-Humulin NPH insulin for each patient was 1.2× their usual daily dose of basal Humulin NPH insulin to compensate for the amount of short-acting insulin that they would not receive on the test days. Blood samples were taken according to a set schedule over 13 hours. HDV was added to Humulin NPH insulin using the method previously described to produce a suspension with a final concentration of 93.6 units of combined HDV Humulin R insulin and HDV Humulin NPH insulin/ml. The final suspension contained 0.52 mg of HDV lipid/ml. The patients were injected with the combined HDV-insulins one hour prior to the morning breakfast. At each of the three daily meals, breakfast, lunch and dinner, a 60 gram carbohydrate meal was prescribed by a dietitian.

The results of the experiments presented in this Experimental Example are now described. HDV-Humulin NPH insulin was well tolerated by the patients and no adverse reactions were observed at the injection sites. Hypoglycemic reactions were not observed in patients receiving this treatment. The blood glucose values of patients treated with HDV-Humulin NPH insulin are graphically presented in FIG. 21. FIG. 21 shows that blood glucose concentrations increased, as anticipated, following meals and glucose concentrations decreased over time until the next meal was eaten. This pattern was observed for all four patients. FIG. 22 shows the effect of a single dose of HDV-Humulin NPH insulin on average blood glucose concentrations in patients consuming three meals during the day. As with the individual patients, blood glucose concentrations increased following meals and glucose concentrations decreased over time until the next meal was eaten. Average blood glucose concentrations were above the baseline value at all time points. The curve suggests that the efficacy of HDV-Humulin NPH insulin improved throughout the day because there was less variation between the high and low concentrations after the lunch and dinner meals than the breakfast meal. The effect of HDV-Humulin NPH insulin on blood glucose concentrations over time relative to blood glucose concentrations during fasting are shown in FIG. 23. Blood glucose concentrations increased following meals then decreased over time towards the glucose concentration during fasting until the next meal was eaten. Blood glucose concentrations were above fasting concentrations throughout the study. Treatment of patients with HDV-Humulin NPH insulin resulted in some degree of post-prandial blood glucose level control, indicating that HDV was able to carry sufficient quantities of Humulin NPH insulin to the liver at mealtimes to provide this control. Blood glucose levels were typical of Type I patients that usually receive basal insulin therapy plus short-acting insulins at meal times.

While the invention has been disclosed with reference to specific embodiments, it is apparent that other embodiments and variations of the invention may be devised by others skilled in the art without departing from the true spirit and scope of the invention. The appended claims are intended to be construed to include all such embodiments and equivalent variations.

What is claimed is:

1. A method of increasing the bioavailability of at least one insulin in a patient, the method comprising:

a. combining at least one insulin with a lipid-based particle to form a construct comprising the at least one insulin, wherein the lipid-based particle is defined by a bipolar lipid membrane comprising lipids comprising cholesterol, dicetyl phosphate, and an amphipathic lipid, and wherein the bipolar lipid membrane further comprises a hepatocyte receptor binding molecule, wherein the amphipathic lipid is at least one selected from the group consisting of 1,2-distearoyl-sn-glycero-3-phosphocholine, 1,2-dipalmitoyl-sn-glycerol[3-phospho-rac-(1-glycero)], 1,2-distearoyl-sn-glycero-3-phosphoethanolamine, 1,2-dipalmitoyl-sn-glycero-3-phosphoethanolamine-N-(succinyl), 1,2-dimyristoyl-sn-glycero-3-phosphate, 1,2-dimyristoyl-sn-glycero-3-phosphocholine, 1,2-distearoyl-sn-glycero-3-phosphate, 1,2-dipalmitoyl-sn-glycero-3-phosphate, and 1,2-dipalmitoyl-sn-glycero-3-phosphocholine;

wherein the hepatocyte receptor binding molecule is the only hepatocyte receptor binder in the composition and is a biotin-containing compound selected from the group consisting of biotin DHPE (2,3-diacetoxypropyl 2-(5-((3aS,6aR)-2-oxohexahydro-1H-thieno[3,4-d]imidazol-4-yl)pentanamido)ethyl phosphate), biotin-X-DHPE (2,3-diacetoxypropyl 2-(6-(5-((3aS,6aR)-2-oxohexahydro-1H-thieno[3,4-d]imidazol-4-yl)pentanamido)hexanamido) ethyl phosphate), and any combinations thereof;

wherein the biotin-containing compound extends outward from the lipid-based particle and binds to a biotin-binding hepatocyte receptor; and, wherein the size of the lipid-based particle ranges from 0.0200 to 0.40 μm; and b. administering the construct containing the at least one insulin to the patient.

2. The method of claim 1, wherein the construct further comprises at least one charged organic molecule selected from the group consisting of protamines, polylysine, poly (arg-pro-thr)$_n$, poly (DL-Ala-poly-L-lys)$_n$, histones, sugar polymers comprising a primary amino group, polynucleotides with primary amino groups, proteins comprising amino acid residues with sulfhydral ($S^-$) functional groups, and acidic polymers.

3. The method of claim 1, wherein the at least one insulin is at least one selected from the group consisting of insulin lispro, insulin aspart, regular insulin, insulin glargine, insulin zinc, human insulin zinc extended, isophane insulin, human buffered regular insulin, insulin glulisine, recombinant human regular insulin, and recombinant human insulin isophane.

4. The method of claim 1, wherein the construct further comprises cellulose acetate phthalate.

5. The method of claim 1, wherein the at least one insulin is chemically modified, thus having an isoelectric point that is distinct from the isoelectric point of the chemically unmodified insulin.

6. A method of forming a time-release composition that provides increased biodistribution of insulin in a warm-bloodied subject, the method comprising:

a. contacting (i) a bulk phase medium comprising an insulin-containing construct and (ii) streptavidin agarose affinity-gel, in a system of pH equal to or greater than about 9.5, wherein the construct comprises insulin and a lipid-based particle defined by a bipolar lipid membrane comprising lipids comprising cholesterol, dicetyl phosphate, and an amphipathic lipid, wherein the amphipathic lipid is at least one selected from the group consisting of 1,2-distearoyl-sn-glycero-3-phosphocholine, 1,2-dipalmitoyl-sn-glycerol[3-phospho-rac-(1-glycero)], 1,2-distearoyl-sn-glycero-3-phosphoethanolamine, 1,2-dipalmitoyl-sn-glycero-3-phosphoethanolamine-N-(succinyl), 1,2-dimyristoyl-sn-glycero-3-phosphate, 1,2-dimyristoyl-sn-glycero-3-phosphocholine, 1,2-distearoyl-sn-glycero-3-phosphate, 1,2-dipalmitoyl-sn-glycero-3-phosphate, and 1,2-dipalmitoyl-sn-glycero-3-phosphocholine, wherein at least one of the lipids comprises iminobiotin or an iminobiotin derivative, wherein the at least one lipid comprising iminobiotin or an iminobiotin derivative extends outward from the lipid-based particle, wherein the size of the lipid-based particle ranges from 0.0200 to 0.40 μm, whereby the insulin-containing construct binds to the affinity-gel;

b. separating the construct-bound affinity-gel from the bulk phase medium; and c. subjecting the construct-bound affinity-gel to a system of pH of around 4.5, whereby the insulin-containing construct is released from the affinity-gel, wherein the released construct contains insoluble insulin.

7. The method of claim 6, wherein the construct further comprises at least one charged organic molecule selected from the group consisting of protamines, polylysine, poly (arg-pro-thr)$_n$, poly (DL-Ala-poly-L-lys)$_n$, histones, sugar polymers comprising a primary amino group, polynucleotides with primary amino groups, proteins comprising amino acid residues with sulfhydral ($S^-$) functional groups, and acidic polymers.

8. The method of claim 6, wherein the at least one insulin is at least one selected from the group consisting of insulin lispro, insulin aspart, regular insulin, insulin glargine, insulin zinc, human insulin zinc extended, isophane insulin, human buffered regular insulin, insulin glulisine, recombinant human regular insulin, and recombinant human insulin isophane.

9. The method of claim 6, wherein the construct further comprises cellulose acetate phthalate.

10. The method of claim 6, wherein the at least one insulin is chemically modified, thus having an isoelectric point that is distinct from the isoelectric point of the chemically unmodified insulin.

11. The method of claim 6, wherein administration of the released construct to the warm-bodied subject results in redissolution of the at least one insulin within the construct.

* * * * *

SEQUENCE LISTING

<160> NUMBER OF SEQ ID NOS: 5

<210> SEQ ID NO 1
<211> LENGTH: 21
<212> TYPE: PRT
<213> ORGANISM: Artificial Sequence
<220> FEATURE:
<223> OTHER INFORMATION: Recombinantly synthesized Human Glargine
      Insulin Analog A-chain

<400> SEQUENCE: 1

Gly Ile Val Glu Glu Cys Cys Thr Ser Ile Cys Ser Leu Tyr Gln Leu
1               5                   10                  15

Glu Asn Tyr Cys Gly
            20

<210> SEQ ID NO 2
<211> LENGTH: 32
<212> TYPE: PRT
<213> ORGANISM: Artificial Sequence
<220> FEATURE:
<223> OTHER INFORMATION: Recombinantly synthesized Human Glargine
      Insulin Analog B-chain

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 3
<211> LENGTH: 33
<212> TYPE: PRT
<213> ORGANISM: Artificial Sequence
<220> FEATURE:
<223> OTHER INFORMATION: Artificial Protamine sequence

<400> SEQUENCE: 3

Met Pro Arg Arg Arg Arg Ser Ser Ser Arg Pro Val Arg Arg Arg
1               5                   10                  15

Arg Pro Arg Val Ser Arg Arg Arg Arg Arg Gly Gly Arg Arg Arg
            20                  25                  30

Arg

<210> SEQ ID NO 4
<211> LENGTH: 21
<212> TYPE: PRT
<213> ORGANISM: Artificial Sequence
<220> FEATURE:
<223> OTHER INFORMATION: Human Insulin A-chain

<400> SEQUENCE: 4

Gly Ile Val Glu Glu Cys Cys Thr Ser Ile Cys Ser Leu Tyr Gln Leu
1               5                   10                  15

Glu Asn Tyr Cys Asn
            20

<210> SEQ ID NO 5
<211> LENGTH: 30
<212> TYPE: PRT
<213> ORGANISM: Artificial Sequence
<220> FEATURE:
<223> OTHER INFORMATION: Human Insulin B-Chain

<400> SEQUENCE: 5

-continued

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```